US011191818B2

(12) United States Patent
Ewenstein et al.

(10) Patent No.: US 11,191,818 B2
(45) Date of Patent: Dec. 7, 2021

(54) USE OF ADAMTS13 FOR TREATING, AMELIORATING AND/OR PREVENTING VASO-OCCLUSIVE CRISIS IN SICKLE CELL DISEASE, ACUTE LUNG INJURY AND/OR ACUTE RESPIRATORY DISTRESS SYNDROME

(71) Applicant: TAKEDA PHARMACEUTICAL COMPANY LIMITED, Osaka (JP)

(72) Inventors: Bruce Ewenstein, Brookline, MA (US); Brahm Goldstein, Cambridge, MA (US); Bernhard Majer, Vienna (AT); Paolo Rossato, Vienna (AT); Friedrich Scheiflinger, Vienna (AT); Marietta Turecek, Mauerbach (AT)

(73) Assignee: TAKEDA PHARMACEUTICAL COMPANY LIMITED, Osaka (JP)

(*) Notice: Subject to any disclaimer, the term of this patent is extended or adjusted under 35 U.S.C. 154(b) by 0 days.

(21) Appl. No.: 16/322,837

(22) PCT Filed: Aug. 4, 2017

(86) PCT No.: PCT/US2017/045573
§ 371 (c)(1),
(2) Date: Feb. 1, 2019

(87) PCT Pub. No.: WO2018/027169
PCT Pub. Date: Feb. 8, 2018

(65) Prior Publication Data
US 2019/0336588 A1 Nov. 7, 2019

Related U.S. Application Data

(60) Provisional application No. 62/371,030, filed on Aug. 4, 2016.

(51) Int. Cl.
*A61K 38/48* (2006.01)
*A61P 7/02* (2006.01)
*A61P 11/00* (2006.01)

(52) U.S. Cl.
CPC ............ *A61K 38/4886* (2013.01); *A61P 7/02* (2018.01); *A61P 11/00* (2018.01)

(58) Field of Classification Search
None
See application file for complete search history.

(56) References Cited

U.S. PATENT DOCUMENTS

| 8,623,352 B2 | 1/2014 | Matthiessen et al. |
| 8,945,895 B2 | 2/2015 | Hasslacher et al. |
| 2005/0266528 A1 | 12/2005 | Laemmie et al. |
| 2007/0015703 A1* | 1/2007 | Wagner ............... A61P 7/02 424/94.63 |
| 2009/0317375 A1* | 12/2009 | Wagner ............... A61K 38/4886 424/94.67 |
| 2011/0086413 A1 | 4/2011 | Grillberger et al. |
| 2011/0229455 A1* | 9/2011 | Matthiessen ........... A61K 47/02 424/94.67 |
| 2014/0271611 A1 | 9/2014 | Schiviz et al. |

FOREIGN PATENT DOCUMENTS

| WO | 2012006594 | 1/2012 |
| WO | 2014151968 | 9/2014 |

OTHER PUBLICATIONS

Zhou et al. "Haemoglobin blocks von Willebrand factor proteolysis by ADAMTS-13: A mechanism associated with sickle cell disease," Thromb Haemost 101: 1070-1077 (2009) (Year: 2009).*
Zhou et al., "Role of Extracellular Hemoglobin in Thrombosis and Vascular Occlusion in Patients with Sickle Cell Anemia," Anemia 2011: 1-5 (2011) (Year: 2011).*
Duits et al., "Enhanced Levels of Soluble VCAM-1 in Sickle Cell Patients and Their Specific Increment during Vasoocclusive Crisis," Clinical Immunology and Immunopathology 81: 96-98 (1996) (Year: 1996).*
Schiviz et al., "A new mouse model mimicking thrombotic thrombocytopenic purpura: correction of symptoms by recombinant human ADAMTS13," blood 21: 6128-6135 (2012) (Year: 2012).*
Mousa et al., "Management of Painful Vaso-Occlusive Crisis of Sickle-Cell Anemia: Consensus Opinion," Clinical and Applied Thrombosis/Hemostasis 16: 365-376 (2010) (Year: 2010).*
Pickens B. et al., "Platelet-delivered ADAMTS13 inhibits arterial thrombisis and prevents thrombotic thrombocytopenic purpura in murine models," Blood, vol. 125, No. 21, May 21, 2015, pp. 3326-3334.
Crescente M. et al., "ADAMTS13 exerts a thrombolytic effect in microcirculation," Thrombosis and Haemostasis, vol. 108, No. 3, Jan. 1, 2012, pp. 527-532.

(Continued)

*Primary Examiner* — Julie Ha
*Assistant Examiner* — Kristina M Hellman
(74) *Attorney, Agent, or Firm* — Troutman Pepper Hamilton Sanders LLP

(57) ABSTRACT

The disclosure provides compositions and methods for treating, ameliorating, and/or preventing a vaso-occlusive crisis (VOC) in a subject suffering from sickle cell disease (SCD). The disclosure also provides compositions and methods for treating, ameliorating, and/or preventing lung injury in a subject suffering from or at risk of suffering from acute lung injury (ALI) and/or acute respiratory distress syndrome (ARDS). The disclosure provides A Disintegrin And Metalloproteinase with Thrombospondin type 1 motif, member-13 (ADAMTS13) or a composition comprising ADAMTS13 for treating, ameliorating, and/or preventing the VOC, or for treating, ameliorating, and/or preventing lung injury in a subject suffering from or at risk of suffering from ALI and/or ARDS.

45 Claims, 6 Drawing Sheets

(56) References Cited

OTHER PUBLICATIONS

Chauhan A.K. et al., "Systemic antithrombotic effects of ADAMTS13," The Journal of Experimental Medicine, Rockefeller University Press, US, vol. 203, No. 3, Mar. 13, 2006, pp. 767-776.
Schnog J.J.B. et al., "ADAMTS13 activity in sickle cell disease," American Journal of Hematology, vol. 81, No. 7, Jul. 1, 2006., pp. 492-498.
Plaimauer B. et al., "Recombinant ADAMTS13 normalizes von Willebrand factor-cleaving activity in plasma of acquired TTP patients by overriding inhibitory antibodies: rADAMTS13 overrides inhibitors in TTP plasma," Journal of Thrombosis and Haemostasis, vol. 9, No. 5, May 1, 2011, pp. 936-944.
Tersteeg C. et al., "Potential for Recombinant ADAMTS 13 as an Effective Therapy for Acquired Thrombotic Thrombocytopenic PurpuraSignificance," Arteriosclerosis, Thrombosis, and Vascular Biology, vol. 35, No. 11, Sep. 3, 2015, pp. 2336-2342.
Kopic A. et al., "Preclinical assessment of a new recombinant ADAMTS-13 drug product (BAX930) for the treatment of thrombotic thrombocytopenic purpura," Journal of Thrombosis and Haemostasis, vol. 14, No. 7, Jul. 1, 2016, pp. 1410-1419.
Skully M. et al., "FIB04-Recombinant human ADAMTS13: first-in-human study evaluating pharmakokinetic, safety and tolerability in hTTP patients," Journal of Thrombosis and Haemostasis, vol. 14, No. S1, May 28, 2016, p. 39.
Ehrlich H.J. et al., "Development of novel treatment options for patients with hamophilia," Hamostaseologie, vol. 33, No. 1, Jan. 1, 2013, pp. S36-S38.
Zhao B. et al., "The Role of von Willebrand Factor and ADAMTS13 in the No-Reflow Phenomenon after Primary Percutaneous Coronary Intervention," Texas Heart Institute Journal, vol. 38, No. 5, Jan. 1, 2011, pp. 516-522.
L'Acqua C. et al., "New perspectives on the thrombotic complications of haemolysis," British Journal of Haematology, vol. 168, No. 2, Oct. 13, 2014, pp. 175-185.
Chang J.C. et al., "Thrombocytopenia in critically ill patients due to vascular microthrombotic disease: pathogensis base don two activation theory of the endothelium," Vascul. Dis. Ther., vol. 2, No. 5, Jun. 30, 2017, pp. 1-7.
International Search Report dated Mar. 1, 2018 in connection with PCT/US17/045573.
Written Opinion dated Mar. 1, 2018 in connection with PCT/US17/045573.
Özpolat et al., "Effects of N-Acetylcysteine in Patients with Sickle Cell Disease," Blood; 124 (21): 4173; Dec. 2014. Found online: https://doi.org/10.1182/blood.V124.21.4173.4173.
Bastarche et al., "Development of Animal Models for the Acute Respiratory Distress Syndrome" Dis. Model. Meeh., (2009), vol. 2, No. 5-8, pp. 218-223.
De Franceschi et al., "Thrombosis and Sickle Cell Disease" Semin. Thromb. Hemost., (2011), pp. 226-236.
Fix, J., "Strategies for Delivery of Peptides Utilizing Absorption-Enhancing Agents" Pharm. Sci., (1996), vol. 85, pp. 1282-1285.
Hebbel et al., "Systems Biology Consideration of the Vasculopathy of Sickle Cell Anemia: The Need for Multi-Modality Chemo-Prophylaxis" Cardiovasc. Hematol. Disord. Drug Targets, (2009), vol. 9, pp. 271-292.
Johnson et al., Acute Lung Injury: Epidemiology, Pathogenesis, and Treatment J. Aerosol Med. Pulmon. Drug Deliv., (2010), vol. 23, pp. 243-252.
Kalish et al., "Dietary ω-3 fatty acids protect against vasculopathy in a transgenic mouse model of sickle cell disease" Haematologica, (2015), vol. 100, pp. 870-880.
Kokame et al., "FRETS-VWF73, a first fluorogenic substrate for ADAMTS13 assay" Br J. Haematol., (2005), vol. 129, No. 1, pp. 93-100.
Matute-Bello et al., "Animal Models of Acute Lung Injury" Am. J. Physiol. Lung Cell Mol. Physiol., (2008), vol. 295, No. 3, pp. L379-L399.
Oliyai et al., "Prodrugs of Peptides and Proteins for Improved Formulation and Delivery" Ann. Rev. Pharmacol. Toxicol., (1993), vol. 32, pp. 521-544.
Plaimauer et al., "Cloning, expression, and functional characterization of the vonWillebrand factor-cleaving protease (ADAMTS13)" Blood, (2002), vol. 15; 100, No. 10, pp. 3626-3632.
Sabaa et al., "Endothelin receptor antagonism prevents hypoxia-induced mortality and morbidity in a mouse model of sickle-cell disease" JCI, (2008), vol. 118, p. 1924.
Sparkenbaugh et al., "Interplay between coagulation and vascular inflammation in sickle cell disease" Br. J. Haematol., (2013), vol. 162, pp. 3-14.
Treadwell et al., "Adult Sickle Cell Quality-of-Life Measurement Information System (ASCQ-Me)" Clin. J. Pain, (2016), vol. 30, No. 10, pp. 902-915.
Tzouvelekis et al., "Serum biomarkers in Acute Respiratory Distress Syndrome an ailing prognosticator" Respiratory Research, (2005), vol. 6, p. 62.
Walkey et al., "Acute respiratory distress syndrome: epidemiology and management approaches" Clinical Epidemiology, (2012), vol. 4, pp. 159-169.
Plaimauer B; Scheiflinger F.,:Expression and Characterization of Recombinant Human ADAMTS—Semin Hematol., (2004), vol. 41, No. 1, pp. 24-33.
Melzack et al., "The McGill Pain Questionnaire: Major Properties and Scoring Methods" Pain, (1975), vol. I, No. 3, pp. 277-299.
Eurasian Office Action issued in Eurasian Application No. 201990373, dated May 12, 2020.

* cited by examiner

USE OF ADAMTS13 FOR TREATING, AMELIORATING AND/OR PREVENTING VASO-OCCLUSIVE CRISIS IN SICKLE CELL DISEASE, ACUTE LUNG INJURY AND/OR ACUTE RESPIRATORY DISTRESS SYNDROME

CROSS REFERENCE TO RELATED APPLICATIONS

This patent application is a 371 National Stage of PCT/US17/45573, filed Aug. 4, 2017, which claims priority pursuant to 35 U.S.C. § 119(e) to U.S. Provisional Patent Application No. 62/371,030, filed Aug. 4, 2016, which are hereby incorporated by reference in their entirety.

FIELD OF THE INVENTION

The disclosure relates to a method for treating sickle cell disease with A Disintegrin And Metalloproteinase with Thrombospondin type 1 motif, member-13 (ADAMTS13). More particularly, the disclosure relates to a method for treating, ameliorating, and/or preventing vaso-occlusive crisis (VOC) in a subject with sickle cell disease (SCD) by administering ADAMTS13. The disclosure includes uses of ADAMTS13 and/or compositions comprising ADAMTS13 for the preparation of medicaments for the treatment, amelioration, and/or prevention of VOC in SCD. The disclosure also relates to a method for treating, ameliorating, or preventing lung injury in a subject suffering from or at risk of suffering from acute lung injury (ALI) and/or acute respiratory distress syndrome (ARDS) with ADAMTS13, and uses of ADAMTS13 and/or compositions comprising ADAMTS13 for the preparation of medicaments for the treatment, amelioration, and/or prevention of ALI and/or ARDS.

BACKGROUND OF THE INVENTION

Sickle cell disease (SCD) is a worldwide distributed hereditary red blood cell disorder, which results from a point mutation ($\beta^S$, 6V) in the β-globin chain leading to the production of a defective form of hemoglobin, hemoglobin S (HbS). Studies of the kinetics of HbS polymerization following deoxygenation have shown it to be a high order exponential function of hemoglobin concentration, thus highlighting a crucial role for cellular HbS concentration in sickling. Pathophysiological studies have shown that the dense, dehydrated red blood cells play a central role in acute and chronic clinical manifestations of SCD, in which intravascular sickling in capillaries, small vessels, and large vessels leads to vaso-occlusion and impaired blood flow with ischemic cell damage in a variety of organs and tissues.

In SCD patients, increased levels of von Willebrand factor (VWF) and of ultra-large VWF multimers have been observed and are associated with acute vaso-occlusive events. The levels of ultra-large VWF multimers are dependent on the activity of the metalloprotease A Disintegrin And Metalloproteinase with Thrombospondin type 1 motif, member-13 (ADAMTS13) that cleaves the hyperadhesive ultra-large VWF multimers under conditions of high fluid shear stress, playing an important role in maintaining a proper balance of hemostatic activity and thrombotic risk. ADAMTS13 cleaves VWF between residues $\text{Tyr}^{1605}$ and $\text{Met}^{1606}$, which corresponds to residues 842-843 after cleavage of the preprosequence. It is this ADAMTS13-mediated cleavage of VWF that is largely responsible for modulation of VWF multimeric size and hemostatic activity. VWF released through stimulation or circulating in blood is important in forming platelet thrombi because it plays a role with collagen on platelet adhesion and agglutination in subendothelial tissue, including damaged vascular walls. VWF release is accompanied and partly triggered by activation of the vascular endothelium. Thus, biomarkers of vascular inflammation provide additional information on the risk of vaso-occlusive events.

Extracellular hemoglobin (ECHb) is increased in SCD patients and inhibits ADAMTS13-mediated VWF proteolysis by binding to the A2 domain of VWF particularly to the ADAMTS13 cleavage site. Thrombospondin-1 (TSP1), which is also increased in patients with SCD, binds to the A2 domain of ultra-large VWF multimers and also prevents VWF degradation by ADAMTS13 by competitively inhibiting ADAMTS13 activity.

SCD is a congenital, life-long illness. People with SCD inherit two abnormal hemoglobin $\beta^S$ genes, one from each parent. When a person has two hemoglobin S genes, Hemoglobin SS (Hb SS), the disease is called sickle cell anemia. This is the most common and often most severe kind of SCD. Hemoglobin SC disease and hemoglobin Sβ thalassemia are two other common forms of SCD. In all forms of SCD, at least one of the two abnormal genes causes a person's body to make hemoglobin S or sickle hemoglobin, in their red blood cells. Hemoglobin is a protein in red blood cells that carries oxygen throughout the body. Sickle hemoglobin differs from normal hemoglobin in its propensity to form polymers under conditions of low oxygen tension, which form stiff rods within the red blood cell, changing it into a crescent, or sickle shape. Sickle-shaped cells are not flexible, which can cause a blockage that slows or stops the flow of blood and essentially obstructs the microcirculation. When this happens, oxygen cannot reach nearby tissues. The lack of tissue oxygen can cause attacks of sudden, severe pain, called vaso-occlusive crisis (VOC), pain crisis, or sickle cell crisis, which results in ischemic injury to the organ supplied and resultant pain. Pain crises constitute the most distinguishing clinical feature of VOC of SCD and are the leading cause of emergency department visits and hospitalizations for affected patients.

VOC is initiated and sustained by interactions among sickle cells, including sickle cell reticulocytes, endothelial cells, leukocytes, and plasma constituents, including VWF. Vaso-occlusion is responsible for a wide variety of clinical complications of SCD, including pain syndromes, stroke, leg ulcers, spontaneous abortion and renal insufficiency. The pain of VOC is often incompletely treated. Current treatment of VOC includes, among other things, the use of fluids, oxygen, and analgesia, while the incidence of VOC may be reduced with chronic red blood cell (RBC) transfusion as well as hydroxyurea. Despite advances in pain management, however, physicians are often reluctant to give patients adequate dosages of narcotic analgesics because of concerns about addiction, tolerance and side effects. In addition to acute VOC, other acute and chronic complications of SCD include renal disease, splenic infarction, increased risk of bacterial infection, acute and chronic anemia, chest syndrome, stroke and ocular disease.

Acute pain in patients with SCD is caused by ischemic tissue injury resulting from the occlusion of microvascular beds by sickled erythrocytes during an acute crisis. For example, the severe bone pain that is characteristic of VOC is believed to be caused by increased intra-medullary pressure, especially within the juxta-articular areas of long bones, secondary to an acute inflammatory response to vascular necrosis of the bone marrow by sickled erythrocytes. The pain may also occur because of involvement of the periosteum or periarticular soft tissue of the joints. The effect of unpredictable recurrences of acute crises on chronic pain creates a unique pain syndrome.

The severity of SCD varies widely from person to person. Advances in the diagnosis and care of SCD have extended the life expectancies of persons with SCD. In high-income countries like the United States, the life expectancy of a person with SCD is now about 40-60 years, whereas it was only 14 years about 40 years ago. At the present time, however, hematopoietic stem cell transplantation (HSCT) is the only cure for SCD. Unfortunately, most people with SCD are either too old for a transplant or do not have a relative who is a good enough genetic match for them to act as a donor for a successful transplant. Thus, there is a need in the art for improved treatments of SCD, including the treatment of vaso-occlusive events of SCD that can reduce symptoms, prevent complications, and improve length and quality of life.

SUMMARY OF THE INVENTION

The disclosure includes a method for treating, ameliorating, and/or preventing a vaso-occlusive crisis (VOC) in a subject suffering from sickle cell disease (SCD), wherein the method comprises administering to the subject in need thereof a therapeutically effective amount of a composition comprising ADAMTS13.

The disclosure includes a method for treating, ameliorating, and/or preventing a lung injury in a subject suffering from acute lung injury (ALI) and/or acute respiratory distress syndrome (ARDS), wherein the method comprises administering to the subject in need thereof a therapeutically effective amount of a composition comprising ADAMTS13.

The disclosure includes uses of ADAMTS13 and/or compositions comprising ADAMTS13 for the preparation of medicaments. Other related aspects are also provided in the disclosure.

The disclosure provides a method for treating, ameliorating, and/or preventing a VOC in a subject suffering from SCD, the method comprising administering to the subject in need thereof a therapeutically effective amount of a composition comprising ADAMTS13. In some embodiments, the subject is treated after symptoms of a VOC are present. In some embodiments, the subject is treated before symptoms of a VOC crisis are present. In some embodiments, treating reduces at least one of inflammation, vasoconstriction, or platelet aggregation, or a combination of any thereof. In some embodiments, treating results in at least one of improved survival, improved lung function, or reduced organ damage, reduced pulmonary vascular leakage, or a combination of any thereof. In some embodiments, treating reduces and/or prevents at least one of impaired blood flow (e.g., ischemia), blood coagulation, vascular inflammation, thrombosis, ischemic cell damage, or organ damage, or a combination of any thereof. In some embodiments, treating reduces and/or prevents pain or severity of the pain. In some embodiments, treating reduces the frequency of occurrence of VOC and/or duration of VOC episodes. In certain embodiments, administration of ADAMTS13 results in reduced expression, level, and/or activation of at least one of VCAM-1, ICAM-1, P-NF-kB/NF-kB ratio, ET-1, TXAS, and HO-1 in an organ. In some embodiments, the comparison is to a control subject. In some embodiments, the comparison is to measurements taken prior to treatment.

In certain embodiments, organs include, but are not limited to, lung, liver, pancreas, skin, retina, prostate, ovary, lymph node, adrenal gland, kidney, heart, gallbladder or GI track. In some embodiments, organ tissue includes, but is not limited to the lungs, liver, spleen, and/or kidneys. In certain embodiments, the organ is a lung. In certain embodiments, the organ is a kidney.

In certain embodiments, administration of ADAMTS13 results in an increase of at least one of Hct, Hb, MCV, and MCH levels in the blood and/or a reduction in at least one of CHCM, HDW, LDH, and neutrophil numbers in the blood as compared to control.

In some aspects of the disclosure, the therapeutically effective amount of ADAMTS13 for treating, ameliorating, or preventing a VOC in a subject suffering from SCD is from about 20 to about 6,000 international units per kilogram body weight. In some aspects, the therapeutically effective amount is from about 40 to about 4,000 international units per kilogram body weight. In some aspects, the therapeutically effective amount is from about 100 to about 3,000 international units per kilogram body weight. In some aspects, the therapeutically effective amount is from about 50 to about 500 international units per kilogram body weight.

In particular aspects, the dosage or therapeutically effective amount for treating, ameliorating, or preventing a VOC in a subject suffering from SCD is from about 10 to about 500 international units per kilogram body weight. In some aspects, the dosage or therapeutically effective amount is from about 50 to about 450 international units per kilogram body weight. In some aspects, the therapeutically effective amount is from about 40 to about 150 international units per kilogram body weight. In some aspects, the therapeutically effective amount is from about 100 to about 500 international units per kilogram body weight. In some aspects, the dosage or therapeutically effective amount is from about 100 to about 400 international units per kilogram body weight. In some aspects, the therapeutically effective amount is from about 100 to about 300 international units per kilogram body weight. In some aspects, the therapeutically effective amount is from about 300 to about 500 international units per kilogram body weight. In some aspects, the dosage or therapeutically effective amount is from about 200 to about 300 international units per kilogram body weight. In some aspects, the dosage or therapeutically effective amount is about 100, about 150, about 200, about 250, about 300, about 350, about 400, about 450, or about 500 international units per kilogram body weight.

In further aspects, the dosage or therapeutically effective amount for treating, ameliorating, or preventing a VOC in a subject suffering from SCD is from about 50 to about 1,000 international units per kilogram body weight. In some aspects, the dosage or therapeutically effective amount is from about 100 to about 900 international units per kilogram body weight. In some aspects, the dosage or therapeutically effective amount is from about 200 to about 800 international units per kilogram body weight. In some aspects, the dosage or therapeutically effective amount is from about 300 to about 700 international units per kilogram body weight. In some aspects, the dosage or therapeutically effective amount is from about 400 to about 600 international units per kilogram body weight. In some aspects, the dosage or therapeutically effective amount is about 500 international units per kilogram body weight.

In some embodiments, the composition comprising ADAMTS13, for treating, ameliorating, or preventing a VOC in a subject suffering from SCD, is administered in a single bolus injection, monthly, every two weeks, weekly, twice a week, daily, every 12 hours, every eight hours, every six hours, every four hours, or every two hours. In some embodiments, the composition comprising ADAMTS13 is administered intravenously or subcutaneously. In some embodiments, the composition comprising ADAMTS13 is administered intravenously. In some embodiments, the composition comprising ADAMTS13 is administered subcutaneously.

In some aspects of the disclosure, the therapeutically effective amount of the composition comprising ADAMTS13 is administered to the subject within 48 hours after the onset of the VOC. In some aspects, the therapeutically effective amount of the composition comprising ADAMTS13 is administered to the subject within 24 hours after the onset of the VOC. In some aspects, the therapeutically effective amount of the composition comprising ADAMTS13 is administered to the subject within 12 hours after the onset of the VOC. In some aspects, the therapeutically effective amount of the composition comprising ADAMTS13 is administered to the subject within 6 hours after the onset of the VOC.

In some aspects of the disclosure, the therapeutically effective amount of the composition comprising ADAMTS13 for preventing the VOC is sufficient to maintain an effective level of ADAMTS13 activity in the subject. In some aspects, the therapeutically effective amount of the composition comprising ADAMTS13 for preventing the VOC is administered monthly, biweekly, weekly, or twice a week to prevent a VOC. In some embodiments the administering is subcutaneous. In some aspects, the administering is intravenous.

The disclosure includes the use of a composition comprising ADAMTS13 for treating or preventing a VOC in a subject suffering from SCD. In some embodiments, the disclosure includes a composition comprising ADAMTS13 for use as a medicament for the treatment or prevention of a VOC in a subject suffering from SCD.

In certain embodiments, the methods of treating or preventing VOC comprises (i) administering ADAMTS13 and (ii) evaluating whether a parameter or symptom has changed, wherein the parameter is selected from the group consisting of inflammation, vasoconstriction, platelet aggregation, lung function, organ (e.g., lung or kidney) damage, pulmonary vascular leakage, blood flow, blood coagulation, vascular inflammation, thrombosis, ischemic cell damage, presence of pain, severity of pain, frequency of occurrence of VOC, duration of VOC episodes, VCAM-1, ICAM-1, P-NF-kB/NF-kB ratio, ET-1, TXAS, HO-1, Hct, Hb, MCV, HDW, reticulocyte numbers, and neutrophil numbers.

The disclosure also provides a method for treating, ameliorating, and/or preventing lung injury in a subject suffering from or at risk of suffering from ALI and/or ARDS, the method comprising administering to the subject in need thereof a therapeutically effective amount of a composition comprising ADAMTS13. In some aspects, the subject suffers from a condition or a combination of the conditions selected from the group consisting of inflammatory pulmonary edema, inflammatory pulmonary infiltrates, impaired oxygenation, and hypoxemia. In some aspects, treating results in at least one of improved survival, improved lung function, or reduced organ damage, reduced pulmonary vascular leakage, or a combination of any thereof. In some aspects, treating reduces at least one of inflammation, vasoconstriction, or platelet aggregation, or a combination of any thereof. In some aspects, treating reduces and/or prevents at least one of impaired blood flow (e.g., ischemia), blood coagulation, vascular inflammation, thrombosis, ischemic cell damage, or organ damage, or a combination of any thereof. In some aspects, treating reduces and/or prevents pain or severity of the pain. In some embodiments, treating reduces the frequency of occurrence or ALI and/or ARDS and/or duration of ALI and/or ARDS episodes. In certain embodiments, administration of ADAMTS13 results in reduced expression, level, and/or activation of at least one of VCAM-1, ICAM-1, P-NF-kB/NF-kB ratio, ET-1, TXAS, and HO-1 in an organ. In some embodiments, the comparison is to a control subject. In some embodiments, the comparison is to measurements taken prior to treatment.

In certain embodiments, organs include, but are not limited to, lung, liver, pancreas, skin, retina, prostate, ovary, lymph node, adrenal gland, kidney, heart, gallbladder or GI track. In some embodiments, organ tissue includes, but is not limited to the lungs, liver, spleen, and/or kidneys. In certain embodiments, the organ is a lung. In certain embodiments, the organ is a kidney.

In certain embodiments, administration of ADAMTS13 results in a reduction in neutrophil numbers in the blood as compared to control.

In some aspects of the disclosure, the therapeutically effective amount of ADAMTS13 for treating, ameliorating, or preventing lung injury in a subject suffering from or at risk of suffering from ALI and/or ARDS is from about 20 to about 6,000 international units per kilogram body weight. In some aspects, the therapeutically effective amount is from about 40 to about 4,000 international units per kilogram body weight. In some aspects, the therapeutically effective amount is from about 100 to about 3,000 international units per kilogram body weight. In some aspects, the therapeutically effective amount is from about 50 to about 500 international units per kilogram body weight.

In particular aspects, the dosage or therapeutically effective amount for treating, ameliorating, or preventing lung injury in a subject suffering from or at risk of suffering from ALI and/or ARDS is from about 10 to about 500 international units per kilogram body weight. In some aspects, the dosage or therapeutically effective amount is from about 50 to about 450 international units per kilogram body weight. In some aspects, the therapeutically effective amount is from about 40 to about 150 international units per kilogram body weight. In some aspects, the therapeutically effective amount is from about 100 to about 500 international units per kilogram body weight. In some aspects, the dosage or therapeutically effective amount is from about 100 to about 400 international units per kilogram body weight. In some aspects, the therapeutically effective amount is from about 100 to about 300 international units per kilogram body weight. In some aspects, the therapeutically effective amount is from about 300 to about 500 international units per kilogram body weight. In some aspects, the dosage or therapeutically effective amount is from about 200 to about 300 international units per kilogram body weight. In some aspects, the dosage or therapeutically effective amount is about 100, about 150, about 200, about 250, about 300, about 350, about 400, about 450, or about 500 international units per kilogram body weight.

In further aspects, the dosage or therapeutically effective amount for treating, ameliorating, or preventing lung injury in a subject suffering from or at risk of suffering from ALI and/or ARDS is from about 50 to about 1,000 international units per kilogram body weight. In some aspects, the dosage or therapeutically effective amount is from about 100 to about 900 international units per kilogram body weight. In some aspects, the dosage or therapeutically effective amount is from about 200 to about 800 international units per kilogram body weight. In some aspects, the dosage or therapeutically effective amount is from about 300 to about 700 international units per kilogram body weight. In some aspects, the dosage or therapeutically effective amount is from about 400 to about 600 international units per kilogram body weight. In some aspects, the dosage or therapeutically effective amount is about 500 international units per kilogram body weight.

In some embodiments, the therapeutically effective amount of the composition comprising ADAMTS13, for treating, ameliorating, and/or preventing lung injury in a subject suffering from or at risk of suffering from ALI and/or ARDS, is administered to the subject within 48 hours after the detection of inflammatory pulmonary edema, inflammatory pulmonary infiltrates, impaired oxygenation, or hypoxemia. In some embodiments, the therapeutically effective amount of the composition comprising ADAMTS13 is administered to the subject within 24 hours after the detection of inflammatory pulmonary edema, inflammatory pulmonary infiltrates, impaired oxygenation, or hypoxemia. In some embodiments, the therapeutically effective amount of the composition comprising ADAMTS13 is administered to the subject within 12 hours after the detection of inflammatory pulmonary edema, inflammatory pulmonary infiltrates, impaired oxygenation, or hypoxemia. In some embodiments, the therapeutically effective amount of the composition comprising ADAMTS13 is administered to the subject within 6 hours after the detection of inflammatory pulmonary edema, inflammatory pulmonary infiltrates, impaired oxygenation, or hypoxemia.

In some embodiments, the composition comprising ADAMTS13 is administered in a single bolus injection, monthly, every two weeks, weekly, twice a week, daily, every 12 hours, every eight hours, every six hours, every four hours, or every two hours. In some embodiments, the composition comprising ADAMTS13 is administered intravenously or subcutaneously. In some embodiments, the composition comprising ADAMTS13 is administered intravenously. In some embodiments, the composition comprising ADAMTS13 is administered subcutaneously.

In various aspects of the disclosure, ADAMTS13 is recombinant ADAMTS13. In some aspects, ADAMTS13 is plasma derived.

In various aspects of the disclosure, the subject is a mammal. In some aspects the subject is a human.

In some aspects, the composition is in a stable aqueous solution ready for administration.

In some aspects, the therapeutically effective amount of the composition comprising ADAMTS13 for treating, ameliorating, and/or preventing lung injury is sufficient to maintain an effective circulating level of ADAMTS13 activity in the subject.

The disclosure includes the use of a composition comprising ADAMTS13 for treating, ameliorating and/or preventing lung injury in a subject suffering from or at risk of suffering from ALI and/or ARDS. In some aspects, the subject is suffering from ALI. In some aspects, the subject is suffering from ARDS.

The disclosure also includes a composition comprising ADAMTS13 for use as a medicament for the treatment, amelioration, or prevention of a lung injury in a subject suffering from or at risk of suffering from ALI and/or ARDS.

In certain embodiments, the methods of treating or preventing ALI/ARDS comprises (i) administering ADAMTS13 and (ii) evaluating whether a parameter or symptom has changed, wherein the parameter is selected from the group consisting of inflammation, vasoconstriction, platelet aggregation, lung function, organ (e.g., lung or kidney) damage, pulmonary vascular leakage, blood flow, blood coagulation, vascular inflammation, thrombosis, ischemic cell damage, frequency of occurrence of ALI/ARDS, duration of ALI/ARDS episodes, VCAM-1, ICAM-1, P-NF-kB/NF-kB ratio, ET-1, TXAS, HO-1, Hct, Hb, MCV, HDW, reticulocyte numbers, and neutrophil numbers.

The foregoing summary is not intended to define every aspect of the invention, and additional aspects are described in other sections, such as the following detailed description. The entire document is intended to be related as a unified disclosure, and it should be understood that all combinations of features described herein are contemplated, even if the combination of features are not found together in the same sentence, or paragraph, or section of this document. Other features and advantages of the invention will become apparent from the following detailed description. It should be understood, however, that the detailed description and the specific examples, while indicating specific embodiments of the invention, are given by way of illustration only, because various changes and modifications within the spirit and scope of the invention will become apparent to those skilled in the art from this detailed description.

DESCRIPTION OF THE FIGURES

FIG. 2A shows that SCD (SS) mice had a significantly greater number of leukocytes and significantly more protein content in bronchioalveolar lavage compared to controls, indicating vascular leakage. Treatment with rADAMTS13 (BAX930/SHP655) markedly reduced this effect, indicating a reduction of systemic inflammation and of abnormalities in pulmonary vascular dysfunction. FIG. 2B shows that rADAMTS13 (BAX930/SHP655) prevented the hypoxia-induced activation of NF-kB in lungs of AA and SCD mice, indicating that ADAMTS13 decreases the pulmonary inflammation process triggered by hypoxia. FIG. 2C shows that rADAMTS13 (BAX930/SHP655) prevented activation of various markers of vascular activation and inflammatory vasculopathy in the lungs of SCD mice after exposure to hypoxic conditions.

FIG. 3A shows that rADAMTS13 (BAX930/SHP655) prevented the hypoxia-induced activation of NF-kB in kidneys of AA and SCD mice, as well as of SCD mice under normoxic conditions, indicating that ADAMTS13 decreases the inflammation process triggered by hypoxia in the kidneys as well as the lungs. FIG. 3B shows that rADAMTS13 (BAX930/SHP655) prevented activation of various markers of vascular activation and inflammatory vasculopathy in the kidneys of SCD mice after exposure to hypoxic conditions.

DETAILED DESCRIPTION OF THE INVENTION

Figure 1:
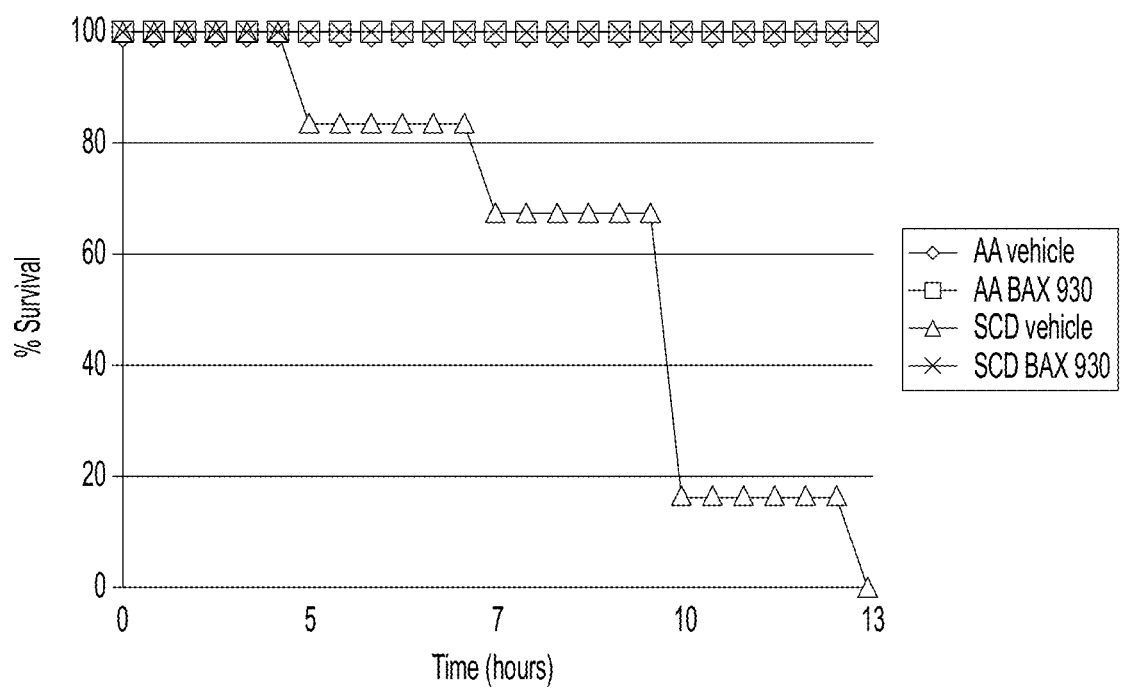
FIG. 1 is a graph showing that ADAMTS13 protects sickle cell mice (SCD) from death related to a severe acute VOC. Mice (n=6) were treated with rADAMTS13 (BAX930/SHP655 (2,940 FRETS-U/kg (~3,200 IU/kg))) and exposed to 7% oxygen for 10 h followed by 3 h recovery at 21% oxygen. Survival curves for rADAMTS13-treated SCD mice, vehicle-treated AA (healthy) mice, and ADAMTS13-treated AA mice, were significantly different (p<0.001) from those of vehicle-treated SCD mice. After 13 hours, no animals survived in the group of vehicle-treated SCD mice, whereas 100% of the animals in all of the other three groups survived.

The disclosure provides, in various aspects, ADAMTS13 for preventing, ameliorating, and/or treating a VOC in SCD.

Before any embodiments of the disclosure are explained in detail, it is to be understood that the invention is not limited in its application to the details of construction and the arrangement of components set forth in the following description or illustrated in the figures and examples. The section headings used herein are for organizational purposes only and are not to be construed as limiting the subject matter described. All references cited in this application are expressly incorporated by reference herein for all purposes.

The disclosure embraces other embodiments and is practiced or carried out in various ways. Also, it is to be understood that the phraseology and terminology used herein is for the purpose of description and should not be regarded as limiting. The terms "including," "comprising," or "having" and variations thereof are meant to encompass the items listed thereafter and equivalents thereof as well as additional items.

The following abbreviations are used throughout.
AA mice Transgenic mice homozygous for Hemoglobin A (HbA)
ADAMTS A Disintegrin And Metalloproteinase with Thrombospondin
ADAMTS13 A Disintegrin And Metalloproteinase with Thrombospondin type 1 motif, member-13
ALI Acute lung injury
ARDS Acute respiratory distress syndrome
BAL Bronchoalveolar lavage
DNA Deoxyribonucleic acid
ET-1 Endothelin 1
FRETS U FRETS units
GAPDH Glyceraldehyde 3-phosphate dehydrogenase
HbA Hemoglobin A
HbS Sickle hemoglobin
HO-1 Heme-oxygenase 1
H/R Hypoxia/Reoxygenation
ICAM-1 Intercellular Adhesion Molecule 1
IU International Units
kDa KiloDalton
LDH Lactate dehydrogenase
NF-kB Nuclear Factor-kappa B
P-NF-kB Phospho-Nuclear Factor-kappa B
rADAMTS13 recombinant ADAMTS13
RBC Red blood cell
RNA Ribonucleic acid
SCD Sickle Cell Disease
SS mice Transgenic mice homozygous for HbS
TXAS Thromboxane synthase
VCAM-1 Vascular Cell Adhesion Molecule-1
VOC Vaso-occlusive crisis
VWF von Willebrand factor It is noted here that, as used in this specification and the appended claims, the singular forms "a," "an," and "the" include plural reference unless the context clearly dictates otherwise. With respect to aspects of the disclosure described as a genus, all individual species are considered separate aspects of the disclosure. If aspects of the disclosure are described as "comprising" a feature, embodiments also are contemplated "consisting of" or "consisting essentially of" the feature.

As used herein, the following terms have the meanings ascribed to them unless specified otherwise.

The term "sickle cell disease (SCD)," as used herein, describes a group of inherited red blood cell disorders that exists in multiple forms. Some forms of SCD are Hemoglobin SS, Hemoglobin SC, Hemoglobin S$\beta^0$ thalassemia, Hemoglobin S$\beta^+$ thalassemia, Hemoglobin SD, and Hemoglobin SE. Although Hemoglobin SC disease and hemoglobin S$\beta$ thalassemia are two common forms of SCD, the disclosure relates to and includes all forms of SCD.

The term "vaso-occlusive crisis (VOC)," as used herein, is an attack of sudden severe pain, which can occur without warning. VOC, also known as pain crisis or sickle cell crisis, is a common painful complication of SCD in adolescents and adults. VOC is initiated and sustained by interactions among sickle cells, endothelial cells and plasma constituents. Vaso-occlusion is responsible for a wide variety of clinical complications of SCD, including pain syndromes, stroke, leg ulcers, spontaneous abortion, and/or renal insufficiency.

The terms "acute lung injury" (ALI) and "acute respiratory distress syndrome" (ARDS) describe clinical syndromes of acute respiratory failure with substantial morbidity and mortality (Johnson et al., *J. Aerosol Med. Pulmon. Drug Deliv.* 23:243-52, 2010). Both ALI and the more severe ARDS represent a spectrum of lung disease characterized by the sudden onset of inflammatory pulmonary edema secondary to myriad local or systemic insults, including bilateral, inflammatory pulmonary infiltrates and impaired oxygenation or hypoxemia (Walkey et al., *Clinical Epidemiology* 4:159-69, 2012). Although ALI and ARDS are two clinical syndromes of lung injury or disease, the disclosure relates to and includes the use of ADAMTS13 in treating, preventing, or ameliorating, not only ALI and ARDS, but all forms of lung injury and lung disease, especially lung disease associated with impaired oxygenation.

"A disintegrin and metalloproteinase with a thrombospondin type 1 motif, member 13 (ADAMTS13)" is also known as von Willebrand factor-cleaving protease (VWFCP). The term "ADAMTS13" or "ADAMTS13 protein," as used herein, includes ADAMTS13 analogs, variants, derivatives (including chemically-modified derivatives) and fragments thereof. In some aspects, the analogs, variants, derivatives, and fragments thereof have increased biological activity compared to ADAMTS13. In various aspects, ADAMTS13 is recombinant ADAMTS13 (rADAMTS13) or is blood-derived ADAMTS13, including plasma- and serum-derived ADAMTS13.

As used herein, an "analog" refers to a polypeptide, e.g., ADAMTS13, substantially similar in structure and having the same biological activity, albeit in certain instances to a differing degree, to a naturally-occurring molecule. Analogs differ in the composition of their amino acid sequences compared to the naturally-occurring polypeptide from which the analog is derived, based on one or more mutations involving (i) deletion of one or more amino acid residues at one or more termini of the polypeptide (including fragments as described above) and/or one or more internal regions of the naturally-occurring polypeptide sequence, (ii) insertion or addition of one or more amino acids at one or more termini (typically an "addition" analog) of the polypeptide and/or one or more internal regions (typically an "insertion" analog) of the naturally-occurring polypeptide sequence or (iii) substitution of one or more amino acids for other amino acids in the naturally-occurring polypeptide sequence. Substitutions are conservative or non-conservative based on the physico-chemical or functional relatedness of the amino acid that is being replaced and the amino acid replacing it.

"Conservatively modified analogs" applies to both amino acid and nucleic acid sequences. With respect to particular nucleic acid sequences, conservatively modified nucleic acids refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified analogs. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, insertions, deletions, additions, or truncations to a nucleic acid, peptide, polypeptide, or protein sequence which alters, adds or deletes a single amino acid or a small percentage of amino acids in the encoded sequence is a "conservatively modified analog" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins (1984)).

As used herein, a "variant" refers to a polypeptide, protein or analog thereof that comprises at least one amino acid substitution, deletion, insertion, or modification, provided that the variant retains the biological activity of the native polypeptide. The term "variant," in some aspects, is interchangeably used with the term "mutant."

As used herein, an "allelic variant" refers to any of two or more polymorphic forms of a gene occupying the same genetic locus. Allelic variations arise naturally through mutation and, in some aspects, result in phenotypic polymorphism within populations. In certain aspects, gene mutations are silent (no change in the encoded polypeptide) or, in other aspects, encode polypeptides having altered amino acid sequences. "Allelic variants" also refer to cDNAs derived from mRNA transcripts of genetic allelic variants, as well as the proteins encoded by them.

The term "derivative" refers to polypeptides that are covalently modified by conjugation to therapeutic or diagnostic agents, labeling (e.g., with radionuclides or various enzymes), covalent polymer attachment such as pegylation (derivatization with polyethylene glycol) and insertion or substitution by chemical synthesis of non-natural amino acids. In some aspects, derivatives are modified to comprise additional chemical moieties not normally a part of the molecule. In certain aspects, these derivatives are called chemically-modified derivatives. Such moieties, in various aspects, modulate the molecule's solubility, absorption, and/or biological half-life. The moieties, in various other aspects, alternatively decrease the toxicity of the molecule and eliminate or attenuate any undesirable side effect of the molecule, etc. Moieties capable of mediating such effects are disclosed in Remington's Pharmaceutical Sciences (1980). Procedure for coupling such moieties to a molecule are well known in the art. For example, in some aspects, an ADAMTS13 derivative is an ADAMTS13 molecule having a chemical modification which confers a longer half-life in vivo to the protein. In one embodiment, the polypeptides are modified by addition of a water-soluble polymer known in the art. In a related embodiment, polypeptides are modified by glycosylation, PEGylation, and/or polysialylation.

As used herein, a "fragment" of a polypeptide refers to any portion of the polypeptide smaller than the full-length polypeptide or protein expression product. Fragments are typically deletion analogs of the full-length polypeptide, wherein one or more amino acid residues have been removed from the amino terminus and/or the carboxy terminus of the full-length polypeptide. Accordingly, "fragments" are a subset of deletion analogs described below.

The term "recombinant" or "recombinant expression system" when used with reference, e.g., to a cell, indicates that the cell has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, underexpressed or not expressed at all. This term also means host cells which have stably integrated a recombinant genetic element or elements having a regulatory role in gene expression, for example, promoters or enhancers. Recombinant expression systems as defined herein will express polypeptides or proteins endogenous to the cell upon induction of the regulatory elements linked to the endogenous DNA segment or gene to be expressed. The cells can be prokaryotic or eukaryotic.

The term "recombinant," when used herein to refer to a polypeptide or protein, means that a polypeptide or protein is derived from recombinant (e.g., microbial or mammalian) expression systems. "Microbial" refers to recombinant polypeptides or proteins made in bacterial or fungal (e.g., yeast) expression systems. The term "recombinant variant" refers to any polypeptide differing from naturally occurring polypeptides by amino acid insertions, deletions, and substitutions, created using recombinant DNA techniques. Guidance in determining which amino acid residues may be replaced, added or deleted without abolishing activities of interest may be found by comparing the sequence of the particular polypeptide with that of homologous peptides and minimizing the number of amino acid sequence changes made in regions of high homology.

The term "agent" or "compound" describes any molecule, e.g., protein or pharmaceutical, with the capability of affecting a biological parameter in the disclosure.

A "control," as used herein, can refer to an active, positive, negative or vehicle control. As will be understood by those of skill in the art, controls are used to establish the relevance of experimental results, and provide a comparison for the condition being tested. In certain aspects, a control is a subject that does not receive an active prophylactic or therapeutic composition. In certain aspects, a control is a subject not experiencing SCD, VOC, ALI, and/or ARDS, for example, but not limited to a healthy control or a subject without any symptoms.

The term "reduces the severity," when referring to a symptom of SCD, VOC in SCD, and/or ALI/ARDS, means that the symptom has delayed onset, reduced severity, reduced frequency, or causes less damage to the subject. Generally, severity of a symptom is compared to a control, e.g., a subject that does not receive an active prophylactic or therapeutic composition, or as compared to the severity of the symptom prior to administration of the therapeutic. In that case, a composition can be said to reduce the severity of a symptom of SCD, VOC in SCD, and/or ALI/ARDS if the symptom is reduced by about 10%, about 15%, about 20%, about 25%, about 30%, about 35%, about 40%, about 50%, about 60%, about 70%, about 80%, about 90%, or about 100% (i.e., essentially eliminated), as compared to the control level of the symptom. In certain aspects, a composition can be said to reduce the severity of a symptom of SCD, VOC in SCD, and/or ALI/ARDS if the symptom is reduced between about 10% to about 100%, about 20% to about 90%, about 30% to about 80%, about 40% to about 70% or about 50% to about 60%, as compared to the control level of the symptom. In certain aspects, a composition can be said to reduce the severity of a symptom of SCD, VOC in SCD, and/or ALI/ARDS if the symptom is reduced between about 10% to about 30%, about 20% to about 40%, about 30% to about 50%, about 40% to about 60%, about 50% to about 70%, about 60% to about 80%, about 70% to about 90% or about 80% to about 100%, as compared to the control level of the symptom. In some aspects, treatment by methods of the disclosure reduces the severity of the pain and/or other symptoms of VOC in SCD and/or ALI/ARDS.

The terms "reduces the expression," "reduces the level," and "reduces the activation" when referring to a biomarker of SCD, VOC in SCD, and/or ALI/ARDS (for example, but not limited to VCAM-1, ICAM-1, P-NF-kB/NF-kB ratio, ET-1, TXAS, HO-1, Hct, Hb, MCV, HDW, reticulocyte numbers, and neutrophil numbers), means that the expression, level, and/or activation of a biomarker has been reduced as compared to control. In that case, a composition can be said to reduce the expression, level, and/or activation of a biomarker of SCD, VOC in SCD, and/or ALI/ARDS if the biomarker is reduced by about 10%, about 15%, about 20%, about 25%, about 30%, about 35%, about 40%, about 50%, about 60%, about 70%, about 80%, about 90%, or about 100% (i.e., essentially eliminated), as compared to the control. In certain aspects, a composition can be said to reduce the expression, level, and/or activation of SCD, VOC in SCD, and/or ALI/ARDS if the expression, level, and/or activation is reduced between about 10% to about 100%, about 20% to about 90%, about 30% to about 80%, about 40% to about 70% or about 50% to about 60%, as compared to the control. In certain aspects, a composition can be said to reduce the expression, level, and/or activation of a biomarker of SCD, VOC in SCD, and/or ALI/ARDS if the biomarker is reduced between about 10% to about 30%, about 20% to about 40%, about 30% to about 50%, about 40% to about 60%, about 50% to about 70%, about 60% to about 80%, about 70% to about 90% or about 80% to about 100%, as compared to the control.

The terms "increases the expression," "increases the level," and "increases the activation" when referring to a biomarker of SCD, VOC in SCD, and/or ALI/ARDS, means that the expression, level, and/or activation of a biomarker has been increased as compared to control. In that case, a composition can be said to increase the expression, level, and/or activation of a biomarker of SCD, VOC in SCD, and/or ALI/ARDS if the biomarker is increased by about 10%, about 15%, about 20%, about 25%, about 30%, about 35%, about 40%, about 50%, about 60%, about 70%, about 80%, about 90%, or about 100% (i.e., essentially eliminated), as compared to the control. In certain aspects, a composition can be said to increase the expression, level, and/or activation of SCD, VOC in SCD, and/or ALI/ARDS if the expression, level, and/or activation is increased between about 10% to about 100%, about 20% to about 90%, about 30% to about 80%, about 40% to about 70% or about 50% to about 60%, as compared to the control. In certain aspects, a composition can be said to increase the expression, level, and/or activation of a biomarker of SCD, VOC in SCD, and/or ALI/ARDS if the biomarker is increased between about 10% to about 30%, about 20% to about 40%, about 30% to about 50%, about 40% to about 60%, about 50% to about 70%, about 60% to about 80%, about 70% to about 90% or about 80% to about 100%, as compared to the control.

The terms "effective amount" and "therapeutically effective amount" each refer to the amount of polypeptide, e.g., ADAMTS13 polypeptide, or composition used to support an observable level of one or more biological activities of the ADAMTS13 polypeptide, as set forth herein. For example, an effective amount, in some aspects of the disclosure, would be the amount necessary to treat or prevent symptoms of VOC in SCD and/or ALI/ARDS.

A "subject" is given its conventional meaning of a non-plant, non-protist living being. In most aspects, the subject is an animal. In particular aspects, the animal is a mammal. In more particular aspects, the mammal is a human. In other aspects, the mammal is a pet or companion animal, a domesticated farm animal, or a zoo animal. In certain aspects, the mammal is a mouse, rat, rabbit, guinea pig, pig, or non-human primate. In other aspects the mammal is a cat, dog, horse, or cow. In various other aspects, the mammal is a deer, mouse, chipmunk, squirrel, opossum, or raccoon.

It also is specifically understood that any numerical value recited herein includes all values from the lower value to the upper value, i.e., all possible combinations of numerical values between the lowest value and the highest value enumerated are to be considered to be expressly stated in this application. For example, if a concentration range is stated as about 1% to 50%, it is intended that values such as 2% to 40%, 10% to 30%, or 1% to 3%, etc., are expressly enumerated in this specification. The values listed above are only examples of what is specifically intended.

Ranges, in various aspects, are expressed herein as from "about" or "approximately" one particular value and/or to "about" or "approximately" another particular value. When values are expressed as approximations, by use of the antecedent "about," it will be understood that some amount of variation is included in the range. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

Sickle Cell Disease and Vaso-Occlusion in Sickle Cell Disease

In some aspects, the disclosure includes ADAMTS13 and compositions comprising ADAMTS13 in the treatment, amelioration, and/or prevention of VOC in SCD. SCD is a worldwide hereditary red blood cell disorder caused by a point mutation in the β-globin gene resulting in the synthesis of pathological HbS, and abnormal HbS polymerization in hypoxic conditions. The two main clinical manifestations of SCD are chronic hemolytic anemia and acute VOC, which are the principal causes of hospitalization of SCD patients. Recent studies have underscored the central role of sickle vasculopathy in the generation of sickle cell-related acute events and chronic organ complications (Sparkenbaugh et al., Br. J. Haematol. 162:3-14, 2013; De Franceschi et al., Semin. Thromb. Hemost. 226-36, 2011; and Hebbel et al., Cardiovasc. Hematol. Disord. Drug Targets, 9:271-92, 2009). The pathophysiology of these complications is based on intravascular sickling in capillaries and small vessels leading to VOC, impaired blood flow, vascular inflammation, and/or thrombosis with ischemic cell damage.

The most common clinical manifestation of SCD is VOC. A VOC occurs when the microcirculation is obstructed by sickled red blood cells, causing ischemic injury to the organ supplied and resultant pain. Pain crises constitute the most distinguishing clinical feature of SCD and are the leading cause of emergency department visits and/or hospitalizations for affected SCD subjects or patients.

Approximately half the SCD subjects or patients with homozygous HbS disease experience VOC. The frequency of crisis is extremely variable. Some SCD subjects or patients have as many as six or more episodes annually, whereas others may have episodes only at great intervals or none at all. Each subjects or patient typically has a consistent pattern for crisis frequency.

The disclosure includes methods for reducing at least one symptom of VOC including, but not limited to, ischemia and pain (e.g., dactylitis, priapism, abdominal, chest, and joint), jaundice, bone infarction, abnormal breathing (e.g., tachypnea and shortness of breath), hypoxia, acidosis, hypotension, and/or tachycardia associated with VOC. In certain aspects, VOC can be defined as a condition comprising one or more of these symptoms. Pain crises begin suddenly. The crisis may last several hours to several days and terminate as abruptly as it began. The pain can affect any body part and often involves the abdomen, appendages, chest, back, bones, joints, and soft tissue, and it may present as dactylitis (bilateral painful and swollen hands and/or feet in children), acute joint necrosis or avascular necrosis, or acute abdomen. With repeated episodes in the spleen, infarctions and autosplenectomy predisposing to life-threatening infection are usual. The liver also may infarct and progress to failure with time. Papillary necrosis is a common renal manifestation of VOC, leading to isosthenuria (i.e., inability to concentrate urine).

Severe deep pain is present in the extremities, involving long bones. Abdominal pain can be severe, resembling acute abdomen; it may result from referred pain from other sites or intra-abdominal solid organ or soft tissue infarction. Reactive ileus leads to intestinal distention and pain. The face also may be involved. Pain may be accompanied by fever, malaise, trouble breathing, painful erections, jaundice and leukocytosis. Bone pain is often due to bone marrow infarction. Certain patterns are predictable, as pain tends to involve bones with the most bone marrow activity and because marrow activity changes with age. During the first 18 months of life, the metatarsals and metacarpals can be involved, presenting as dactylitis or hand-foot syndrome. Although the above patterns describe commonly encountered presentations, any area of the body of the subject with blood supply and sensory nerves can be affected in VOC.

Often, no precipitating cause can be identified for what causes a VOC. However, because deoxygenated HbS becomes semi-solid, the most likely physiologic trigger of VOC is hypoxemia. This may be due to acute chest syndrome or accompany respiratory complications. Dehydration also can precipitate pain, since acidosis results in a shift of the oxygen dissociation curve (Bohr effect), causing hemoglobin to desaturate more readily. Hemoconcentration also is a common mechanism. Another common trigger of VOC are changes in body temperature, whether an increase due to fever or a decrease due to environmental temperature change. Lowered body temperature likely leads to crises as the result of peripheral vasoconstriction.

In certain embodiments, VOC can be defined as having an increase in peripheral neutrophils as compared to a control. In certain embodiments, VOC can be defined as an increase in pulmonary vascular leakage (e.g., increased number of leukocytes in a bronchoalveolar lavage (BAL) and/or protein content (BAL protein (mg/mL)) as compared to a control.

In certain embodiments, increased levels of vascular activation (e.g., as measured by increased expression, levels, and/or activity of VCAM-1 and/or ICAM-1) in an organ, as compared to control, is a marker for VOC. In certain embodiments, increased levels of inflammatory vasculopathy (e.g., as measured by increased expression, levels, and/or activity of VCAM-1 and/or ICAM-1) in an organ, as compared to control, is a marker for VOC. In certain embodiments, increased levels of vascular activation and inflammatory vasculopathy in a tissue, as compared to control, is a marker for VOC. In certain embodiments, the organ is lung and/or kidney. In certain embodiments, the organ is kidney.

In certain embodiments, VOC can be defined as the increased expression, levels, and/or activation of at least one of NF-kB (wherein activation of NF-kB is measured by P-NF-kB or the ratio of P-NF-kB/NF-kB), VCAM-1 and ICAM-1 as compared to control. In certain embodiments, VOC can be defined as increased expression or level of at least one of endothelin-1 (ET-1), thromboxane synthase (TXAS), and heme-oxygenase-1 (HO-1) as compared to control. In certain embodiments, these increases are seen in lung tissue. In certain embodiments, these increases are seen in kidney tissue. In certain embodiments, increased expression and/or levels of TXAS, ET-1, and VCAM-1, and activation of NF-kB in the kidney tissue are markers for VOC.

In certain embodiments, VOC can be defined by hematology parameters. In certain embodiments, VOC can be defined as a decrease in the levels of at least one of Hct, Hb, MCV, and MCH as compared to control. In certain embodiments, VOC can be defined as a decrease in the levels of at least two of Hct, Hb, MCV, and MCH as compared to control. In certain embodiments, VOC can be defined as a decrease in the levels of at least three of Hct, Hb, MCV, and MCH as compared to control. In certain embodiments, VOC can be defined as an increase in the levels of at least one of CHCM, HDW, neutrophil numbers, and LDH as compared to control. In certain embodiments, VOC can be defined as an increase in the levels of at least two of CHCM, HDW, neutrophil numbers, and LDH as compared to control. In certain embodiments, VOC can be defined as an increase in the levels of at least three of CHCM, HDW, neutrophil numbers, and LDH as compared to control. In certain embodiments, VOC can be defined as a decrease in Hct levels as compared to control. In certain embodiments, VOC can be defined as a decrease in Hb levels as compared to control. In certain embodiments, VOC can be defined as a decrease in MCV as compared to control. In certain embodiments, VOC can be defined as a decrease in MCH as compared to control. In certain embodiments, VOC can be defined as an increase in CHCM as compared to control. In certain embodiments, VOC can be defined as an increase in HDW as compared to control. In certain embodiments, VOC can be defined as an increase in neutrophil numbers as compared to control. In certain embodiments, VOC can be defined as an increase in LDH as compared to control. In certain embodiments, VOC can be defined as a decrease in the levels of at least one of Hct, Hb, MCV, and MCH as compared to control and/or an increase in the levels of at least one of CHCM, HDW, neutrophil numbers, and LDH as compared to control. In certain embodiments, VOC can be defined as a decrease in the levels of Hct, Hb, MCV, and MCH as compared to control and/or an increase in the levels of CHCM, HDW, neutrophil numbers, and LDH as compared to control.

Models of SCD and Methods of Testing Effectiveness of Prophylaxis or Treatment

In some embodiments, the disclosure includes study of the effects of a recombinant ADAMTS13 (i.e., BAX930/SHP655) in a mouse model of SCD (Tim Townes mouse) during acute SCD related events, mimicked by exposing SCD mice to hypoxia. Studies are carried out under normoxic and hypoxic conditions, wherein efficacy of the prophylaxis or treatment dose(s) in the mouse model (including measuring overall survival) and biological effects of the treatment(s) with BAX930/SHP655 on lung injury and vascular inflammation are studied after exposing sickle cell disease mice to hypoxia.

In some embodiments, a transgenic mouse model of SCD is used (Kalish et al., *Haematologica* 100:870-80, 2015). In some aspects, healthy control ($Hba^{tm1(HBA)Tow}$ $Hbb^{tm3(HBG1,HBB)Tow}$) and SCD ($Hba^{tm1(HBA)Tow}$ $Hbb^{tm2(HBG1,HBB^*)Tow}$) mice are exposed to hypoxia/re-oxygenation (H/R) stress (Kalish et al., infra). Such H/R stress has been shown to biologically recapitulate the acute VOC and organ damage observed in acute VOC in human SCD patients. In some aspects, healthy (AA) and SCD (SS) mice are subjected to hypoxia (e.g., about 7 or 8% oxygen) for certain time periods (e.g., about 10 hours) followed by certain time periods (e.g., 3 hours) of re-oxygenation (e.g., about 21% oxygen, room air condition) (Kalish et al., infra).

In various aspects, models of SCD and controls are subject to conditions of normoxia or hypoxia. In normoxia experiments, healthy control (AA) and SCD (SS) mice receive a single intravenous administration of either rAD-AMTS13 (e.g., 2,940 FRETS-U/kg (~3,200 IU/kg)) or buffer (vehicle) at a fixed volume (e.g., 10 mL/kg) and are subject to normoxic (e.g., about 21% oxygen, room air condition) conditions. Animals are studied for varied periods of time after treatment with ADAMTS13 or vehicle and exposure to normoxia or hypoxia. Blood is collected and complete blood count (CBC) is measured. A CBC is a blood test used to evaluate overall health and detect a wide range of disorders, including among other things, anemia. Various other endpoints, including but not limited to, hematology, coagulation parameters, biomarkers of inflammation, vasculopathy, and histopathology are measured.

In exemplary aspects, hypoxia experiments are carried out, wherein healthy control (AA) and SCD (SS) mice receive a single intravenous administration of ADAMTS13 (e.g., 500 IU/kg, 1,000 IU/kg or 3,200 IU/kg) or vehicle at an affixed volume (e.g., 10 mL/kg). In certain embodiments, the dose administered to a human subject is about 10% that administered to a rodent (e.g., mouse) subject. In certain embodiments, the dose administered to a human subject is about 9% that administered to a rodent (e.g., mouse) subject. In certain embodiments, the dose administered to a human subject is about 8% that administered to a rodent (e.g., mouse) subject. In certain embodiments, the dose administered to a human subject is about 7% that administered to a rodent (e.g., mouse) subject. In certain embodiments, the dose administered to a human subject is less than about 10%, e.g., about 7% to about 10%, that administered to a rodent (e.g., mouse) subject.

After injection (e.g., about 1-3 hours after injection), mice are exposed to hypoxia (e.g., about 7% or 8% oxygen) for a time period (e.g., about 10 hours) followed by a time period of re-oxygenation (e.g., about 3 hours) to mimic SCD related VOC events. In some aspects, the same parameters as detailed for normoxic studies are evaluated.

In additional exemplary aspects, hypoxia experiments are carried out, wherein healthy control (AA) and SCD (SS) mice are exposed to hypoxia (e.g., about 8% oxygen, or higher) for a time period (e.g., about 10 hours) followed by a time period of re-oxygenation (e.g., about 3 hours) to mimic SCD related VOC events. Then, at various time points thereafter including, but not limited to, immediately after, or about 1, 3, 6, 12, 24, 36, 48 or 72 hours after the experimentally-induced vaso-inclusive event, mice receive either a single intravenous administration of ADAMTS13 (e.g., 500 IU/kg, 1,000 IU/kg or 3,200 IU/kg) or vehicle at an affixed volume (e.g., 10 mL/kg), or multiple injections at 12 or 24 intervals. In some aspects, the same parameters as detailed for normoxic studies are evaluated.

In various aspects, any target tissue is examined for effectiveness of treatment with ADAMTS13 in in vitro or in vivo models and/or under conditions of VOC. In some aspects, organ tissue includes, but is not limited to, lung, liver, pancreas, skin, retina, prostate, ovary, lymph node, adrenal gland, kidney, heart, gallbladder or GI tract. In some aspects, organ tissue includes, but is not limited to, the lungs, liver, spleen, and/or kidneys.

For example, in some aspects, target tissues are collected to examine effects of ADAMTS13 under conditions of normoxia or hypoxia. Tissues are frozen and/or fixed in formalin. Frozen tissues are used for immunoblot analysis with specific antibodies against nuclear factor-kappa B (NF-kB), endothelin-1 (ET-1), heme-oxygenase 1 (HO-1), intercellular adhesion molecule-1 (ICAM-1), thromboxane synthase (TXAS), and vascular cell adhesion molecule-1 (VCAM-1). Fixed organs are used for standard pathology (H&E staining).

In some embodiments, markers of vaso-constriction, platelet aggregation, inflammation, oxidative stress, anti-oxidant response and/or tissue damage are measured to determine effectiveness of treatment. In some aspects, nuclear factor kappa B is measured in both its normal (NF-kB) and activated (P-NF-kB) forms. NF-kB is a transcriptional factor which has been described to coordinate the inflammatory and anti-oxidant response. The ratio between the activated and the normal forms is evaluated. In some aspects, ET-1 is measured. ET-1 is a potent vasoconstrictor that is produced by vascular endothelial cells. ET-1 plays a role in several pathophysiological processes, including cardiovascular hypertrophy, pulmonary hypertension and chronic renal failure. In some aspects, HO-1 is measured. HO-1 is the inducible, rate-limiting enzyme in the catabolism of heme and might attenuate the severity of outcomes from vaso-occlusive and hemolytic crises, acting as a vasoprotective anti-oxidant. In some aspects, ICAM-1 is measured. ICAM-1 is continuously present in low concentrations in the membranes of leukocytes and endothelial cells. Although ICAM-1 does not appear to be involved in sickle cell adhesion to vascular endothelium, ICAM-1 may exacerbate VOC by promoting leukocyte adhesion. In some aspects, TXAS is measured. TXAS is an endoplasmic reticulum membrane protein that catalyzes the conversion of prostaglandin H2 to thromboxane A2. TXAS is a potent vasoconstrictor and inducer of platelet aggregation. Thus, TXAS is a potent inducer of vaso-constriction and platelet aggregation. TXAS plays a role in several pathophysiological processes including hemostasis, cardiovascular disease, and stroke. In some aspects, VCAM-1 is measured. VCAM-1 mediates the adhesion of lymphocytes and other blood cells to the vascular endothelium and therefore may contribute to vaso-occlusive events. In some aspects, inflammatory cell infiltrates are measured in organ tissue.

In exemplary aspects, immunoblot analyses with specific antibodies against NF-kB, ET-1, HO-1, ICAM-1, TXAS, and VCAM-1 are carried out to measure the expression of these enzymes in the cells and tissues of models or subjects of the disclosure to determine effectiveness of treatment. In exemplary aspects, the expression of NF-kB, ET-1, HO-1, ICAM-1, TXAS, and/or VCAM-1 is measured in organ tissue from AA and SCD mice treated with either vehicle or ADAMTS13. In certain embodiments, organs include, but are not limited to, lung, liver, pancreas, skin, retina, prostate, ovary, lymph node, adrenal gland, kidney, heart, gallbladder or GI track. In certain embodiments, the organ is lung, liver, spleen, and/or kidney.

In certain embodiments, administration of ADAMTS13 results in reduced levels of vascular activation and/or inflammatory vasculopathy in an organ as compared to control. In certain embodiments, the organ is lung. In certain embodiments, the organ is kidney.

In certain embodiments, administration of ADAMTS13 results in reduced expression, level, and/or activation of at least one of VCAM-1, ICAM-1, NF-kB (wherein reduced activation of NF-kB is measured by P-NF-kB or the ratio of P-NF-kB/NF-kB), ET-1, TXAS, and HO-1 as compared to control. In certain embodiments, administration of ADAMTS13 results in reduced expression, level, and/or activation of at least two of VCAM-1, ICAM-1, NF-kB, ET-1, TXAS, and HO-1 as compared to control. In certain embodiments, administration of ADAMTS13 results in reduced expression, level, and/or activation of at least three of VCAM-1, ICAM-1, NF-kB, ET-1, TXAS, and HO-1 as compared to control. In certain embodiments, administration of ADAMTS13 results in reduced expression, level, and/or activation of at least four of VCAM-1, ICAM-1, NF-kB, ET-1, TXAS, and HO-1 as compared to control. In certain embodiments, administration of ADAMTS13 results in reduced expression, level, and/or activation of at least five of VCAM-1, ICAM-1, NF-kB, ET-1, TXAS, and HO-1 as compared to control. In certain embodiments, administration of ADAMTS13 results in reduced expression, level, and/or activation of VCAM-1, ICAM-1, NF-kB, ET-1, TXAS, and HO-1 as compared to control. In certain embodiments, administration of ADAMTS13 results in reduced expression, level, and/or activation of VCAM-1 as compared to control. In certain embodiments, administration of ADAMTS13 results in reduced expression, level, and/or activation of ICAM-1 as compared to control. In certain embodiments, administration of ADAMTS13 results in reduced expression, level, and/or activation of VCAM-1 and ICAM-1 as compared to control. In certain embodiments, administration of ADAMTS13 results in reduced expression and/or level of ET-1 as compared to control. In certain embodiments, administration of ADAMTS13 results in reduced expression and/or level of TXAS as compared to control. In certain embodiments, administration of ADAMTS13 results in reduced expression and/or level of HO-1 as compared to control. In certain embodiments, administration of ADAMTS13 results in reduced ratio of P-NF-kB/NF-kB as compared to control. In certain embodiments, administration of ADAMTS13 results in a reduction of at least one of P-NF-kB/NF-kB ratio, ET-1 expression and/or level, TXAS expression and/or level, and HO-1 expression and/or level as compared to control. In certain embodiments, administration of ADAMTS13 results in a reduction of P-NF-kB/NF-kB ratio, ET-1 expression and/or level, TXAS expression and/or level, and HO-1 expression and/or level as compared to control. In certain embodiments, the organ is lung. In certain embodiments, the organ is kidney.

In further exemplary aspects, the measurement of these markers is carried out after the animal models are subject to conditions of hypoxia and reoxygenation (H/R) as described herein. In further exemplary aspects, the measurement of these markers is carried out after the subjects experience VOC.

In some embodiments, blood flow is measured as an indicatory of treatment effectiveness. In some embodiments, blood flow is measured by, but not limited to, ultrasound, PET, fMRI, NMR, laser Doppler, electromagnetic blood flow meter, or a wearable device.

In some embodiments, reduction or prevention of thrombosis is a measurement of the effectiveness of the treatment. In some embodiments, the presence of thrombosis is measured by, but not limited to, histopathological examination, ultrasound, D-dimer test, venography, MRI, or CT/CAT scan. In some aspects, thrombus formation is determined in organ tissue.

In some embodiments, reduction or prevention of pulmonary vascular leakage (i.e., lung leakage and damage) is a measurement of the effectiveness of the treatment. In some embodiments, bronchoalveolar lavage (BAL) measurements or parameters (total protein and leukocyte content) are measured as markers of pulmonary vascular leakage (to determine the extent of lung damage and effectiveness of treatment (e.g., treatment with ADAMTS13)). Pulmonary leakage can result in an increase in protein and/or leukocyte content in the BAL. BAL fluids are collected and cellular contents are recovered by centrifugation and counted by microcytometry as previously reported (Kalish et al., *Haematologica* 100:870-80, 2015, incorporated herein by reference in its entirety and for all purposes). In some embodiments, reduction or prevention of an increase in peripheral neutrophils is a measurement of the effectiveness of the treatment. The percentage of neutrophils is determined on cytospin centrifugation and the supernatant fluids are used for determination of total protein content (Kalish et al., supra).

In some embodiments, improvement of lung function is measured as an indicatory of treatment effectiveness. Lung function can be measured by, but not limited to, a peak flow test, a spirometry and reversibility test, a lung volume test, a gas transfer test, a respiratory muscle test, exhaled carbon monoside test, or a exhaled nitric oxide test.

In some embodiments, hematology parameters are measured to determine effectiveness of treatment (e.g., treatment with ADAMTS13). The following hematology parameters are determined: lactate dehydrogenase (LDH) as a general marker of cell damage; hematocrit (Hct) and mean corpuscular volume (MCV), as a measure of erythrocyte viability; hemoglobin (Hb), mean corpuscular hemoglobin (MCH) and cell hemoglobin concentration (CHCM), as indicators of oxygen binding capacity; heterogeneity of red cell distribution (HDW), as an indicator of the presence of dense red cells; reticulocyte count, as an indicator of anemia status; and neutrophil count, as an indicator of systemic inflammatory status.

In certain embodiments, administration of ADAMTS13 ameliorates the reduction of the levels of at least one of Hct, Hb, MCV and MCH in the blood as compared to control. In certain embodiments, administration of ADAMTS13 ameliorates the reduction of the levels of at least two of Hct, Hb, MCV and MCH in the blood as compared to control. In certain embodiments, administration of ADAMTS13 ameliorates the reduction of the levels of at least three of Hct, Hb, MCV and MCH in the blood as compared to control. In certain embodiments, administration of ADAMTS13 ameliorates the reduction of the levels of Hct, Hb, MCV and MCH in the blood as compared to control. In certain embodiments, administration of ADAMTS13 ameliorates the increase of at least one of CHCM, HDW, LDH, and neutrophil number as compared to control. In certain embodiments, administration of ADAMTS13 ameliorates the increase of at least two of CHCM, HDW, LDH, and neutrophil number as compared to control. In certain embodiments, administration of ADAMTS13 ameliorates the increase of at least three of CHCM, HDW, LDH, and neutrophil number as compared to control. In certain embodiments, administration of ADAMTS13 ameliorates the increase of CHCM, HDW, LDH, and neutrophil number as compared to control. In certain embodiments, ADAMTS13 ameliorates the reduction of Hct, Hb, MCV, and MCH levels and ameliorates the increase in CHCM, HDW, LDH, and neutrophil levels as compared to control.

In certain embodiments, administration of ADAMTS13 results in an increase in the levels of at least one of Hct, Hb, MCV and MCH in the blood as compared to control. In certain embodiments, administration of ADAMTS13 results in an increase in the levels of at least two of Hct, Hb, MCV and MCH in the blood as compared to control. In certain embodiments, administration of ADAMTS13 results in an increase in the levels of at least three of Hct, Hb, MCV and MCH in the blood as compared to control. In certain embodiments, administration of ADAMTS13 results in an increase in the levels of Hct, Hb, MCV and MCH in the blood as compared to control. In certain embodiments, administration of ADAMTS13 results in a decrease in at least one of CHCM, HDW, LDH, and neutrophil number as compared to control. In certain embodiments, administration of ADAMTS13 results in a decrease in at least two of CHCM, HDW, LDH, and neutrophil number as compared to control. In certain embodiments, administration of ADAMTS13 results in a decrease in at least three of CHCM, HDW, LDH, and neutrophil number as compared to control. In certain embodiments, administration of ADAMTS13 results in a decrease in CHCM, HDW, LDH, and neutrophil number as compared to control. In certain embodiments, ADAMTS13 results in an increase of Hct, Hb, MCV, and MCH levels and a reduction in CHCM, HDW, LDH, and neutrophil levels as compared to control.

In some embodiments, methods of measuring the levels of VWF and of ultra-large VWF multimers are used. In SCD patients, increased levels of VWF and of ultra-large VWF multimers have been observed and are associated with acute vaso-occlusive events. The increased levels of circulating VWF multimers are dependent on the activity of ADAMTS13 that cleaves the hyperadhesive ultra-large VWF under conditions of high fluid shear stress, playing an important role in maintaining a proper balance of hemostatic activity and thrombotic risk. More specifically, ADAMTS13 cleaves VWF between amino acid residues $Tyr^{1605}$ and $Met^{1606}$, which corresponds to amino acid residues 842-843 after cleavage of the preprosequence. It is this ADAMTS13-mediated cleavage that is largely responsible for VWF multimer size, which correlates with primary hemostatic activity. Methods of measuring VWF and ultra-large VWF multimers, including various types of immunoblot analyses with specific antibodies against VWF, are carried out to measure the expression or level of VWF. Additionally, other known methods of measuring VWF are included in various aspects of the disclosure.

In some aspects, effectiveness is measured by decreased organ damage as compared to control or baseline measurements. In some embodiments, organ damage is measured by radiological imaging such as, but not limited to, CT/CAT scanning, ultrasound, X-ray, MRI, and nuclear medicine. In some embodiments, organ damage is measured by a change in various biomarkers including, but not limited to, blood urea nitrogen (BUN), creatinine, BUN/creatinine ratio, troponin, neuron-specific enolase (NSE). In some embodiments, tissue changes are measured by histopathological examination.

One of ordinary skill in the art is able to select an appropriate measure of any biomarker disclosed herein associated with the organ (defined above) and/or bodily fluid to be measured. Bodily fluids include, but are not limited to, blood (including blood plasma and blood serum), lymph, cerebrospinal fluid, lactation products (e.g., milk), amniotic fluids, urine, saliva, perspiration, tears, menses, feces, and including fractions thereof.

In some aspects, effectiveness is measured by assessing the Quality-of-Life of the subject (e.g., using the Adult Sickle Cell Quality-of-Life Measurement Information System (ASCQ-Me) as reported by Treadwell et al., Clin. J Pain 30(10):902-915 (2016)). The ASCQ-Me centers around seven topics: emotional impact (five question survey related to emotional distress (e.g., hopelessness, loneliness, depression, and worry); pain episode frequency and severity (number of episodes, time since last episode; severity of pain in last attack on a scale from 1-10); how long did the attack last, how much did the attack impact your life); pain impact (asking about the frequency and severity and how it impacted activities); sickle cell disease medical history checklist; sleep impact (how easy to fall asleep, how often cannot fall asleep); social functioning impact (reliance on others, how health impacted activities); and stiffness impact (stiff joints causing sleeplessness, movement during the day, movement upon wakefulness).

In various aspects, effectiveness of prophylaxis and/or treatment is determined by measuring pain severity (e.g., as measured by a pain rating scale), pain relief, perceived need for medication, treatment satisfaction, the frequency of VOC occurrence, the duration of VOC episode, the length and/or duration of hospitalization, costs associated with a hospital stay, and/or the duration of the requirement for pain medication (e.g., i.v. opiates).

In certain aspects, pain severity is measured using the McGill/Melzack Pain Questionnaire (Melzack et al., Pain 1975 September; 1(3):277-99), in which the subject selects one or more words that best describe their pain. In certain aspects, pain severity is measured using the Visual Analog Scale (VAS). The VAS is a 10 cm, non-hatched line anchored with one end as "no pain" and the other end as "worst pain possible." Patients are instructed to mark on the line their level of pain between the two anchors. VAS scores are calculated by measuring the distance, in centimeters, between the "no pain" anchor and the patient's mark indicating their level of pain resulting in a pain severity score ranging from 0 mm to 10 cm. In certain aspects, pain severity is measured using the Numeric Rating Scale (NRS). NRS is an 11-point scale anchored with "no pain" and "worst pain possible." Patients are instructed to report their current level of pain on a scale from 0 to 10 where 0 means no pain and 10 means the worst pain possible.

In certain aspects, pain relief can be measured as a global assessment of how a patient's pain may have changed since the last assessment (i.e., current assessment minus previous assessment) as used to anchor the changes noted on the NRS and VAS scales. Patients reported pain relief in response to the question: "Compared to the last time you marked your pain, tell us how much your pain has changed." Patients could respond that their pain was "a lot worse," "a little worse," "the same," "a little better," or "a lot better."

In certain aspects, the need for medication can be patient or healthcare worker reported.

In certain aspects, treatment satisfaction can be a patient-reported. Reporting can be on a scale from "not at all," "somewhat satisfied (happy)," "very satisfied (happy)," or "do not know."

Acute Lung Injury and Acute Respiratory Distress Syndrome

In some embodiments, the disclosure includes ADAMTS13, compositions comprising ADAMTS13, and methods of using ADAMTS13 in the treatment, amelioration, and/or prevention of acute lung injury (ALI) and acute respiratory distress syndrome (ARDS), including the resultant ventilator-associated lung injury. Pathogenesis of ALI/ARDS is explained by injury to both the vascular endothelium and alveolar epithelium. Phase III clinical trials by the NHLBI ARDS Network have resulted in improvement in survival and a reduction in the duration of mechanical ventilation with a lung-protective ventilation strategy and fluid conservative protocol. However, there is a strong unmet medical need for additional treatments because there are no existing specific pharmacologic therapies for ALI/ARDS. Therefore, the use of ADAMTS13 in the treatment of ALI/ARDS represents a breakthrough in the treatment of ALI/ARDS.

ALI, in some aspects, is a disorder of acute inflammation that causes disruption of the lung endothelial and epithelial barriers. Cellular characteristics of ALI include loss of alveolar-capillary membrane integrity, excessive transepithelial neutrophil migration, and release of pro-inflammatory, cytotoxic mediators. Several studies have documented increased release of VWF and upregulation of intracellular adhesion molecule-1 (ICAM-1) following endothelial injury (Johnson, supra). Transepithelial neutrophil migration is an important feature of ALI because neutrophils are the primary perpetrators of inflammation. Prolonged activation of neutrophils contributes to basement membrane destruction and increased permeability of the alveolar-capillary barrier. (Johnson, supra).

ARDS, in some aspects, includes acute onset tachypnea, hypoxemia, diffuse pulmonary infiltrates, and loss of lung compliance characterized by high short-term mortality in adults (Walkey, supra). Therapeutic strategies for ARDS focus upon treating the underlying etiology and providing supportive care that reduces the progression of lung injury. Most patients with ARDS develop respiratory failure severe enough to require mechanical ventilatory support. Mechanical ventilation can cause further injury to the lungs called ventilator-associated lung injury (VALI) from the combined mechanistic forces of overdistension and cyclic recruitment. VALI produces "biotrauma" from systemic release of inflammatory cytokines. Currently, the primary goal for management of ARDS is the reduction of VALI. (Walkey, supra).

ADAMTS13 significantly reduced the markers of lung injury and vascular dysfunction in normal mice. More specifically, the disclosure shows that dosing of normal (control) mice with recombinant ADAMTS13 under hypoxic conditions resulted in reduced lung expression of various protein markers of lung injury and vascular dysfunction, which indicates that ADAMTS13 can be used in treating or ameliorating lung damage resulting from acute lung injury characterized by the sudden onset of pulmonary edema (including inflammatory pulmonary edema) secondary to myriad local or systemic insults, including bilateral, inflammatory pulmonary infiltrates and impaired oxygenation or hypoxemia.

In certain embodiments, ALI and/or ARDS can be defined by one of more, but not limited to, ischemia, abnormal breathing (e.g., tachypnea and shortness of breath), non-cardiogenic pulmonary edema, pulmonary infiltrates, decreased oxygenation, and decreased ventilation associated with ALI/ARDS. The disclosure includes methods for reducing symptoms of ALI/ARDS including, but not limited to, at least one of ischemia, abnormal breathing (e.g., tachypnea and shortness of breath), non-cardiogenic pulmonary edema, pulmonary infiltrates, decreased oxygenation, decreased ventilation, and combinations thereof associated with ALI/ARDS.

In certain embodiments, ALI and/or ARDS can be defined as having an increase in peripheral neutrophils as compared to a control. In certain embodiments, ALI and/or ARDS can be defined as an increase in pulmonary vascular leakage (e.g., increased number of leukocytes in a bronchoalveolar lavage (BAL) and/or protein content (BAL protein (mg/mL)) as compared to a control.

In certain embodiments, increased levels of vascular activation in an organ, as compared to control, is a marker for ALI and/or ARDS. In certain embodiments, increased levels of inflammatory vasculopathy in an organ, as compared to control, is a marker for ALI and/or ARDS. In certain embodiments, increased levels of vascular activation and inflammatory vasculopathy in a tissue, as compared to control, is a marker for ALI and/or ARDS. In certain embodiments, the organ is lung and/or kidney.

In certain embodiments, ALI and/or ARDS can be defined as the increased expression, levels, and/or activation of at least one of NF-kB (wherein activation of NF-kB is measured by P-NF-kB or the ratio of P-NF-kB/NF-kB), VCAM-1, and/or ICAM-1 as compared to control. In certain embodiments, ALI and/or ARDS can be defined as increased expression or level of at least one of endothelin-1 (ET-1), thromboxane synthase (TXAS), and heme-oxygenase-1 (HO-1) as compared to control. In certain embodiments, these increases are seen in lung tissue. In certain embodiments, these increases are seen in kidney tissue. In certain embodiments, increased expression and/or levels of TXAS and ET-1 and activation of NF-kB in the kidney tissue are markers for ALI and/or ARDS.

In certain embodiments, ALI and/or ARDS can be defined by hematology parameters. In certain embodiments, ALI and/or ARDS can be defined as an increase in neutrophil numbers as compared to control. In certain embodiments, ALI and/or ARDS can be defined as an increase in neutrophil numbers as compared to control.

In certain embodiments, ALI and/or ARDS can also be defined by an increase of at least one of the following serum biomarkers: surfactant-associated protein (SP)-A, SP-B, SP-D, KL-6/MUC1, IL-1, IL-2, IL-3, IL-6, IL-8, IL-10, IL-15, TNFα, adhesion molecules (e.g., E, L-selectin), MMP-9, LTB4, and Ferritin. See e.g., Tzouvelekis et al., *Respiratory Research* 2005, 6:62), which his incorporated herein in its entirety.

Models of ALI/ARDS and Methods of Testing Effectiveness of Prophylaxis or Treatment Animal models for ALI are described in Matute-Bello et al., Am. J. Physiol. Lung Cell Mol. Physiol. 295(3):L379-99, 2008, which is incorporated by reference in their entireties for all purposes. In some instances, ALI in humans is characterized histopathologically by neutrophilic alveolitis, injury of the alveolar epithelium and endothelium, hyaline membrane formation, and microvascular thrombi. In some aspects, animal models of experimental lung injury can been used to investigate mechanisms of ALI. For example, you can reproduce risk factors for ARDS, such as sepsis, lipid embolism secondary to bone fracture, acid aspiration, ischemia-reperfusion of pulmonary or distal vascular beds, and other clinical risks. In certain aspects, animal models of ALI reproduce the mechanisms and consequences of ALI, including the physiological and pathological changes that occur. In humans, the intrapulmonary inflammatory response begins before the onset of clinically defined ALI and is most intense about 3 days after the onset of ALI and/or ARDS. The acute inflammatory phase is followed by a chronic fibroproliferative phase. For example, pulmonary function tests can show restriction, consistent with the parenchymal fibrosis seen in lung biopsies or autopsy specimens.

Animal models for ARDS are described in Bastarche et al., Dis. Model. Mech. 2(5-8):218-23, 2009, which is incorporated by reference in their entireties for all purposes. For example, in humans, pneumonia and sepsis are the two most common predisposing conditions for the development of ARDS. In some aspects, these conditions can be modeled in mice by using the Gram-negative bacterial endotoxin LPS, which can be administered either directly to the lungs through intratracheal injection or inhalation, or given intraperitoneally or intravenously to incite a systemic inflammatory response. Mice treated with intratracheal LPS have an acute and robust inflammatory cell influx to the lung with resolution by 48 hours. Intraperitoneal LPS activates systemic inflammation and is associated with a mild lung injury. This injury can be augmented with either repeated injections of LPS or the implantation of an LPS pump in the peritoneal cavity to continually release LPS for hours, or even days. Another commonly used model of lung injury is hyperoxia, where mice breathe a high partial pressure of oxygen that is highly toxic to the alveolar epithelium and causes extensive alveolar epithelial injury with only a modest amount of inflammation. An additional commonly studied model is ventilator-induced lung injury, which correlates excellently to human ventilator-induced lung injury; however, in the absence of an additional stimulus or extremely high tidal volumes, this model does not induce substantial lung injury in mice. One recent study showed a modest degree of lung inflammation, vascular leak and activation of alveolar coagulation with tidal volumes of 15 ml/kg compared with low tidal volumes of 7.5 ml/kg. To get a more severe injury, higher tidal volumes (as high as 35 ml/kg) are required. A recent, comprehensive review on animal models of ALI by Matute-Bello et al. (Am. J. Physiol. Lung Cell Mol. Physiol. 295:L379-L399, 2008), also incorporated herein by reference for all purposes discusses each model in great detail.

In certain aspects, the disclosed methods and composition can improve symptoms such as, but not limited to, ischemia, abnormal breathing (e.g., tachypnea and shortness of breath), non-cardiogenic pulmonary edema, pulmonary infiltrates (e.g., measured by chest radiography), decreased oxygenation (e.g., measured by pulse oximetry [$SpO_2$] or arterial blood gas [$PaO_2$]), and decreased ventilation (e.g., measured by end-tidal $CO_2$ or arterial blood gas [$PaCO_2$], a decrease in the days on a ventilator or an increase in ventilator free days) associated with ALI/ARDS.

In various aspects, effectiveness of prophylaxis and/or treatment is determined by measuring survival, length and/or frequency of hospitalization, length and/or duration of ICU admissions, and/or costs associated with a hospital stay.

In various aspects, effectiveness of prophylaxis and/or treatment is determined by measuring a decrease in the number of and/or severity of ALI and/or ARDS associated complications. Complications can include, but are not limited to, pulmonary complications (e.g., barotrauma, volutrauma, pulmonary embolism, pulmonary fibrosis, ventilator-associated pneumonia (CAP), and airway complications); gastrointestinal complications (e.g., bleeding (ulcer, lesions), dysmotility, pneumoperitoneum, and bacterial translocation); cardiac complications (e.g., abnormal heart rhythms, and myocardial dysfunction); kidney (acute kidney failure and positive fluid balance); mechanical complications (e.g., vascular injury, pneumothorax (by placing pulmonary artery catheter), tracheal injury/stenosis (result of intubation and/or irritation by endotracheal tube); nutritional complications (e.g., malnutrition (catabolic state), electrolyte deficiency); and general complications (e.g., muscle weakness and exercise tolerance).

In certain embodiments, measurement of the effectiveness of treatment, amelioration, and prevention is the same as those disclosed above for VOC.

In certain embodiments, organs include, but are not limited to, lung, liver, pancreas, skin, retina, prostate, ovary, lymph node, adrenal gland, kidney, heart, gallbladder or GI track. In certain embodiments, the organ is lungs, liver, spleen, and/or kidneys.

In certain embodiments, administration of ADAMTS13 results in reduced levels of vascular activation and/or inflammatory vasculopathy in an organ as compared to control. In certain embodiments, the organ is lung. In certain embodiments, the organ is kidney.

In certain embodiments, administration of ADAMTS13 results in reduced expression, level, and/or activation of at least one of ICAM-1, NF-kB (wherein reduced activation of NF-kB is measured by P-NF-kB or the ratio of P-NF-kB/NF-kB), ET-1, TXAS, and HO-1 as compared to control. In certain embodiments, administration of ADAMTS13 results in reduced expression, level, and/or activation of at least two of ICAM-1, NF-kB, ET-1, TXAS, and HO-1 as compared to control. In certain embodiments, administration of ADAMTS13 results in reduced expression, level, and/or activation of at least three of ICAM-1, NF-kB, ET-1, TXAS, and HO-1 as compared to control. In certain embodiments, administration of ADAMTS13 results in reduced expression, level, and/or activation of at least four of ICAM-1, NF-kB, ET-1, TXAS, and HO-1 as compared to control. In certain embodiments, administration of ADAMTS13 results in reduced expression, level, and/or activation of ICAM-1, NF-kB, ET-1, TXAS, and HO-1 as compared to control. In certain embodiments, administration of ADAMTS13 results in reduced expression, level, and of ICAM-1 as compared to control. In certain embodiments, administration of ADAMTS13 results in reduced expression and/or level of ET-1 as compared to control. In certain embodiments, administration of ADAMTS13 results in reduced expression and/or level of TXAS as compared to control. In certain embodiments, administration of ADAMTS13 results in reduced expression and/or level of HO-1 as compared to control. In certain embodiments, administration of ADAMTS13 results in reduced ratio of P-NF-kB/NF-kB as compared to control. In certain embodiments, administration of ADAMTS13 results in a reduction of at least one of P-NF-kB/NF-kB ratio, ET-1 expression and/or level, TXAS expression and/or level, and HO-1 expression and/or level as compared to control. In certain embodiments, administration of ADAMTS13 results in a reduction of P-NF-kB/NF-kB ratio, ET-1 expression and/or level, TXAS expression and/or level, and HO-1 expression and/or level as compared to control.

In certain embodiments, administration of ADAMTS13 results in the amelioration of the increase of neutrophil number in the blood as compared to control.

In certain embodiments, administration of ADAMTS13 results in a decrease in at least one of the following serum biomarkers as compared to control: surfactant-associated protein (SP)-A, SP-B, SP-D, KL-6/MUC1, IL-1, IL-2, IL-3, IL-6, IL-8, IL-10, IL-15, TNFα, adhesion molecules (e.g., E, L-selectin), MMP-9, LTB4, and Ferritin.

ADAMTS13

In some aspects, the disclosure includes ADAMTS13 (also known as "A13") and compositions comprising ADAMTS13 in the treatment and prevention of SCD. In particular aspects, the disclosure includes ADAMTS13 and compositions comprising ADAMTS13 in the treatment and prevention of VOC in SCD. The ADAMTS13 protease is about a 180 kDa to 200 kDa glycosylated protein produced predominantly by the liver. ADAMTS13 is a plasma metalloprotease which cleaves VWF multimers and down regulates their activity in platelet aggregation. To date, ADAMTS13 has been associated with clotting disorders, such as inherited thrombotic thrombocytopenic purpura (TTP), acquired TTP, cerebral infarction, myocardial infarction, ischemic/reperfusion injury, deep vein thrombosis, and disseminated intravascular coagulation (DIC), such as sepsis-related DIC.

All forms of ADAMTS13 known in the art are contemplated for use in the methods and uses of the disclosure. Mature ADAMTS13 has a calculated molecular mass of about 145 kDa whereas purified plasma-derived ADAMTS13 has an apparent molecular mass of about 180 kDa to 200 kDa, probably due to post-translational modifications consisting with present consensus sequences for 10 potential N-glycosylation sites, and several O-glycosylation sites and one C-mannosylation site in the TSP1 repeats.

As used herein, "ADAMTS13" refers to a metalloprotease of the ADAMTS (a disintegrin and metalloproteinase with thrombospondin type 1 motifs) family that cleaves VWF between residues $Tyr^{1605}$ and $Met^{1606}$. In the context of the disclosure, "ADAMTS13", "A13", or an "ADAMTS13 protein" embraces any ADAMTS13 protein, for example, ADAMTS13 from a mammal such as a primate, human (NP620594), monkey, rabbit, pig, bovine (XP610784), rodent, mouse (NP001001322), rat (XP342396), hamster, gerbil, canine, feline, frog (NP001083331), chicken (XP415435), and biologically active derivatives thereof. As used herein, "ADAMTS13", "A13", or "ADAMTS13 protein" refers to recombinant, natural, or plasma-derived ADAMTS13 protein. Mutant and variant ADAMTS13 proteins having activity are also embraced, as are functional fragments and fusion proteins of the ADAMTS13 proteins. In some aspects, an ADAMTS13 protein further comprises a tag that facilitates purification, detection, or both. The ADAMTS13 protein of the disclosure, in some aspects, is further modified with an additional therapeutic moiety or a moiety suitable imaging in vitro or in vivo.

ADAMTS13 protein includes any protein or polypeptide with ADAMTS13 activity, particularly the ability to cleave the peptide bond between residues Tyr-842 and Met-843 of VWF. Human ADAMTS13 proteins include, without limitation, polypeptides comprising the amino acid sequence of GenBank accession number NP 620594 (NM139025.3) or a processed polypeptide thereof, for example a polypeptide in which the signal peptide (amino acids 1 to 29) and/or propeptide (amino acids 30-74) have been removed. In certain aspects, an ADAMTS13 protein refers to a polypeptide comprising an amino acid sequence that is highly similar to that of NP 620596 (ADAMTS13 isoform 2, preproprotein) or amino acids 75 to 1371 of P_620594 (ADAMTS13 isoform 2, mature polypeptide). In yet another embodiment, ADAMTS13 proteins include polypeptides comprising an amino acid sequence highly similar to that of NP 620595 (ADAMTS13 isoform 3, preproprotein) or amino acids 75 to 1340 of NP_620595 (ADAMTS13 isoform 1, mature polypeptide). In certain aspects, an ADAMTS13 protein includes natural variants with VWF cleaving activity and artificial constructs with VWF cleaving activity. In certain aspects, ADAMTS13 encompasses any natural variants, alternative sequences, isoforms or mutant proteins that retain some basal activity. Many natural variants of human ADAMTS13 are known in the art, and are embraced by the formulations of the disclosure, some of which include mutations selected from R7W, V88M, H96D, R102C, R193W, T196I, H234Q, A250V, R268P, W390C, R398H, Q448E, Q456H, P457L, P475S, C508Y, R528G, P618A, R625H, I673F, R692C, A732V, E740K, A900V, S903L, C908Y, C951G, G982R, C1024G, A1033T, R1095W, R1095W, R1123C, C1213Y, T1226I, G1239V, and R1336W. Additionally, ADAMTS13 proteins include natural and recombinant proteins that have been mutated, for example, by one or more conservative mutations at a non-essential amino acid. Preferably, amino acids essential to the enzymatic activity of ADAMTS13 will not be mutated. These include, for example, residues known or presumed to be essential for metal binding such as residues 83, 173, 224, 228, 234, 281, and 284, and residues found in the active site of the enzyme, e.g., residue 225. Similarly, in the context of the disclosure, ADAMTS13 proteins include alternate isoforms, for example, isoforms lacking amino acids 275 to 305 and/or 1135 to 1190 of the full-length human protein.

In some aspects, ADAMTS13 proteins are further modified, for example, by post-translational modifications (e.g., glycosylation at one or more amino acids selected from human residues 142, 146, 552, 579, 614, 667, 707, 828, 1235, 1354, or any other natural or engineered modification site) or by ex vivo chemical or enzymatic modification, including without limitation, glycosylation, modification by water-soluble polymer (e.g., PEGylation, sialylation, HESylation, etc.), tagging, and the like.

In some aspects, the ADAMTS13 protein is human ADAMTS13 or a biologically active derivative or fragment thereof as described in U.S. Patent Application Publication No. 2011/0229455 and/or in U.S. Patent Application Publication No. 2014/0271611, each of which are incorporated herein by reference in their entirety and for all purposes.

In certain aspects, the recombinant ADAMTS13 can be BAX930/SHP655. In certain aspects, the ADAMTS13 protein includes any protein or polypeptide with ADAMTS13 activity, particularly the ability to cleave the peptide bond between residues Tyr-842 and Met-843 of VWF with at least 70%, at least 75%, at least 80%, at least 85%, at least 90%, at least 91%, at least 92%, at least 93%, at least 94%, at least 95%, at least 96%, at least 97%, at least 98%, or at least 99% sequence homology to BAX930/SHP655.

Proteolytically active recombinant ADAMTS13 may be prepared by expression in mammalian cell cultures, as described in Plaimauer et al, (2002, Blood. 15; 100(10): 3626-32) and US 2005/0266528, the disclosures of which are herein incorporated by reference in their entireties for all purposes. Methods for the expression of recombinant ADAMTS13 in cell culture are disclosed in Plaimauer B, Scheiflinger F. (Semin Hematol. 2004 January; 41(1):24-33 and US 2011/0086413, the disclosures of which are herein incorporated by reference in their entireties for all purposes. See also, WO2012/006594, incorporated by reference in their entireties for all purposes, for methods of producing recombinant ADAMTS13 in cell culture.

Methods for purifying ADAMTS13 protein from a sample are described in U.S. Pat. No. 8,945,895, which is incorporated herein by reference for all purposes. Such methods include, in some aspects, enriching for ADAMTS13 protein by chromatographically contacting the sample with hydroxyapatite under conditions that allow ADAMTS13 protein to appear in the eluate or supernatant from the hydroxyapatite. The methods may further comprise tandem chromatography with a mixed mode cation exchange/hydrophobic interaction resin that binds ADAMTS13 protein. Additional optional steps involve ultrafiltration/diafiltration, anion exchange chromatography, cation exchange chromatography, and viral inactivation. In some aspects, such methods include inactivating virus contaminants in protein samples, where the protein is immobilized on a support. Also provided herein, in some aspects, are compositions of ADAMTS13 prepared according to the methods described in U.S. Pat. No. 8,945,895.

ADAMTS13 Compositions and Administration

In aspects of the disclosure, ADAMTS13 is administered to a subject in need thereof. To administer ADAMTS13 described herein to a subject, ADAMTS13 is, in some aspects, formulated in a composition comprising one or more pharmaceutically acceptable carriers.

The term "pharmaceutically acceptable," as used in connection with compositions described herein, refers to molecular entities and other ingredients of such compositions that are physiologically tolerable and do not typically produce untoward reactions when administered to a mammal (e.g., a human). Preferably, the term "pharmaceutically acceptable" means approved by a regulatory agency of the Federal or a state government or listed in the U.S. Pharmacopeia or other generally recognized pharmacopeia for use in mammals, and more particularly in humans. "Pharmaceutically acceptable carriers" include any and all clinically useful solvents, dispersion media, coatings, antibacterial and antifungal agents, isotonic and absorption delaying agents and the like. In some aspects, the composition forms solvates with water or common organic solvents. Such solvates are included as well.

In some aspects, the disclosure provides stabilized formulations of plasma derived ADAMTS13 and recombinant ADAMTS13 (rADAMTS13) proteins as described in U.S. Patent Application Publication No. 2011/0229455 (now U.S. Pat. No. 8,623,352) and/or in U.S. Patent Application Publication No. 2014/0271611, both of which are incorporated herein by reference for all purposes. In some embodiments, the formulations provided herein retain significant ADAMTS13 activity when stored for extended periods of time. In some embodiments, the formulations of the disclosure reduce or retard dimerization, oligomerization, and/or aggregation of an ADAMTS13 protein.

In some aspects, the disclosure provides formulations of ADAMTS13 comprising a therapeutically effective amount or dose of an ADAMTS13 protein, a sub-physiological to physiological concentration of a pharmaceutically acceptable salt, a stabilizing concentration of one or more sugars and/or sugar alcohols, a non-ionic surfactant, a buffering agent providing a neutral pH to the formulation, and optionally a calcium and/or zinc salt. Generally, the stabilized ADAMTS13 formulations provided herein are suitable for pharmaceutical administration. In some aspects, the ADAMTS13 protein is human ADAMTS13 or a biologically active derivative or fragment thereof as described in U.S. Patent Application Publication No. 2011/0229455 and/or in U.S. Patent Application Publication No. 2014/0271611, each of which are incorporated herein by reference in their entirety and for all purposes.

In some aspects, the ADAMTS13 formulations are liquid or lyophilized formulations. In other embodiments, a lyophilized formulation is lyophilized from a liquid formulation as described in U.S. Patent Application Publication No. 2011/0229455 and/or in U.S. Patent Application Publication No. 2014/0271611, each of which are incorporated herein by reference in their entirety and for all purposes. In certain embodiments of the formulations provided herein, the ADAMTS13 protein is a human ADAMTS13 or recombinant human ADAMTS13, or a biologically active derivative or fragment thereof as described in U.S. Patent Application Publication No. 2011/0229455 and/or in U.S. Patent Application Publication No. 2014/0271611, each of which are incorporated herein by reference in their entirety and for all purposes.

The composition of the disclosure is, in various aspects, administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. In some embodiments, administration is subcutaneous. Administration by intravenous, intradermal, intramuscular, intramammary, intraperitoneal, intrathecal, retrobulbar, intrapulmonary injection and or surgical implantation at a particular site is contemplated as well. In some embodiments, administration is intravenous. Generally, compositions are essentially free of pyrogens, as well as other impurities that could be harmful to the recipient.

Formulation of the composition or pharmaceutical composition will vary according to the route of administration selected (e.g., solution or emulsion). An appropriate composition comprising the composition to be administered is prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles, in some aspects, include sodium chloride solution, Ringer's dextrose, dextrose and sodium chloride, lactated Ringer's or fixed oils. Intravenous vehicles, in certain aspects, include various additives, preservatives, or fluid, nutrient or electrolyte replenishers.

Compositions or pharmaceutical compositions useful in the compounds and methods of the disclosure containing ADAMTS13 as an active ingredient contain, in various aspects, pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form.

A variety of aqueous carriers, e.g., water, buffered water, 0.4% saline, 0.3% glycine, or aqueous suspensions contain, in various aspects, the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents, in some instances, are a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions, in some aspects, contain one or more preservatives, for example ethyl, or n-propyl, p-hydroxybenzoate.

In some aspects, ADAMTS13 or ADAMTS13 compositions are lyophilized for storage and reconstituted in a suitable carrier prior to use. Any suitable lyophilization and reconstitution techniques known in the art are employed. It is appreciated by those skilled in the art that lyophilization and reconstitution leads to varying degrees of protein activity loss and that use levels are often adjusted to compensate.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above.

In some embodiments, the ADAMTS13 formulations provided herein may further comprise one or more pharmaceutically acceptable excipients, carriers, and/or diluents as described in U.S. Patent Application Publication No. 2011/0229455 and/or in U.S. Patent Application Publication No. 2014/0271611, each of which are incorporated herein by reference in their entirety and for all purposes.

In some embodiments, the ADAMTS13 formulations provided herein will have a tonicity in a range described in as described in U.S. Patent Application Publication No. 2011/0229455 and/or in U.S. Patent Application Publication No. 2014/0271611, each of which are incorporated herein by reference in their entirety and for all purposes.

In some aspects, the disclosure provides formulations of ADAMTS13 comprising the exemplary formulations described in Section III ("ADAMTS13 Compositions and Formulations") of U.S. Patent Application Publication No. 2011/0229455. The methods of ADAMTS13 production and compositions thereof as described in U.S. Patent Application Publication No. 2011/0229455 and/or in U.S. Patent Application Publication No. 2014/0271611 are incorporated herein by reference in their entirety for all purposes. Additionally, actual methods for preparing parenterally administrable formulations and compositions are known or are apparent to those skilled in the art and are described in more detail in, for example, Remington's Pharmaceutical Science, 15th ed., Mack Publishing Company, Easton, Pa. (1980).

In various aspects, the pharmaceutical compositions are in the form of a sterile injectable aqueous, oleaginous suspension, dispersions or sterile powders for the extemporaneous preparation of sterile injectable solutions or dispersions. The suspension, in some aspects, is formulated according to the known art using those suitable dispersing or wetting agents and suspending agents which have been mentioned above. The sterile injectable preparation, in certain aspects, is a sterile injectable solution or suspension in a non-toxic parenterally-acceptable diluent or solvent, for example as a solution in 1,3-butane diol. In some embodiments, the carrier is a solvent or dispersion medium containing, for example, water, ethanol, polyol (for example, glycerol, propylene glycol, and liquid polyethylene glycol, and the like), suitable mixtures thereof, vegetable oils, Ringer's solution and isotonic sodium chloride solution. In addition, sterile, fixed oils are conventionally employed as a solvent or suspending medium. For this purpose any bland fixed oil is employed, in various aspects, including synthetic mono- or diglycerides. In addition, fatty acids such as oleic acid find use in the preparation of injectables.

In all cases the form must be sterile and must be fluid to the extent that easy syringability exists. The proper fluidity is maintained, for example, by the use of a coating, such as lecithin, by the maintenance of the required particle size in the case of dispersion and by the use of surfactants. It must be stable under the conditions of manufacture and storage and must be preserved against the contaminating action of microorganisms, such as bacteria and fungi. The prevention of the action of microorganisms is brought about by various antibacterial and antifungal agents, for example, parabens, chlorobutanol, phenol, sorbic acid, thimerosal, and the like. In many cases, it will be desirable to include isotonic agents, for example, sugars or sodium chloride. In certain aspects, prolonged absorption of the injectable compositions is brought about by the use in the compositions of agents delaying absorption, for example, aluminum monostearate and gelatin.

Compositions useful for administration, in certain aspects, are formulated with uptake or absorption enhancers to increase their efficacy. Such enhancers include, for example, salicylate, glycocholate/linoleate, glycholate, aprotinin, bacitracin, SDS, caprate and the like. See, e.g., Fix (J. Pharm. Sci., 85:1282-1285, 1996) and Oliyai et al. (Ann. Rev. Pharmacol. Toxicol., 32:521-544, 1993), each of which are incorporated herein by reference in their entirety and for all purposes.

In addition, the properties of hydrophilicity and hydrophobicity of the compositions used in the compositions and methods of the disclosure are well balanced, thereby enhancing their utility for both in vitro and especially in vivo uses, while other compositions lacking such balance are of substantially less utility. Specifically, compositions in the disclosure have an appropriate degree of solubility in aqueous media which permits absorption and bioavailability in the body, while also having a degree of solubility in lipids which permits the compounds to traverse the cell membrane to a putative site of action.

In particular aspects, ADAMTS13 is provided in a pharmaceutically acceptable (i.e., sterile and non-toxic) liquid, semisolid, or solid diluent that serves as a pharmaceutical vehicle, excipient, or medium. Any diluent known in the art is used. Exemplary diluents include, but are not limited to, polyoxyethylene sorbitan monolaurate, magnesium stearate, methyl- and propylhydroxybenzoate, talc, alginates, starches, lactose, sucrose, dextrose, sorbitol, mannitol, gum acacia, calcium phosphate, mineral oil, cocoa butter, and oil of theobroma.

The composition is packaged in forms convenient for delivery. The composition is enclosed within a capsule, caplet, sachet, cachet, gelatin, paper, or other container. These delivery forms are preferred when compatible with delivery of the composition into the recipient organism and, particularly, when the composition is being delivered in unit dose form. The dosage units are packaged, e.g., in vials, tablets, capsules, suppositories, or cachets.

The disclosure includes methods for treating, ameliorating, and/or preventing VOC in SCD in a subject, including administering an effective amount of ADAMTS13 or an ADAMTS13 composition as described herein. The composition is introduced into the subject to be treated by any conventional method as described herein in detail above. In certain aspects, the composition is administered in a single dose or a plurality of doses over a period of time (as described in more detail below).

In some embodiments, the composition comprising ADAMTS13 is administered to the subject within about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 60, 72, 84, 96, 108, or 120 hours after the onset of the VOC. In some embodiments, the composition comprising ADAMTS13 is administered to the subject within about 1-2 hours, about 1-5 hours, about 1-10 hours, about 1-12 hours, about 1-24 hours, about 1-36 hours, about 1-48 hour, about 1-60 hours, about 1-72 hours, about 1-84 hours, about 1-96 hours, about 1-108 hours, or about 1-120 hours after the onset of the VOC. In some embodiments, the composition comprising ADAMTS13 is administered to the subject within about 2-5 hours, about 5-10 hours, about 10-20 hours, about 20-40 hours, about 30-60 hours, about 40-80 hours, about 50-100 hours, or about 60-120 hours after the onset of the VOC. In some embodiments, the composition is administered within 1 week of the VOC. In some embodiments, the composition is administered daily after the VOC. In some embodiments, the composition is administered weekly after the VOC. In some embodiments, the composition is administered every day. In some embodiments, the composition is administered every other day. In some embodiments, the composition is administered every third day. In some embodiments, the composition is administered twice a week. In some embodiments, the composition is administered until the clinical manifestations (e.g., symptoms and/or biomarkers) resolve. In some embodiments, the composition is administered until a day after clinical manifestations resolve. In some embodiments, the composition is administered for at least two days after clinical manifestations resolve. In some embodiments, the composition is administered for at least three days after clinical manifestations resolve. In some embodiments, the composition is administered for at least a week after clinical manifestations resolve.

In some aspects, the composition comprising ADAMTS13 is administered to the subject to prevent the onset of VOC. In such preventative treatment, ADAMTS13 is administered in a singular bolus injection or in multiple doses to maintain a circulating level of ADAMTS13 effective to prevent the onset of the VOC. In such aspects, the composition comprising ADAMTS13 is administered monthly, every two weeks, weekly, twice a week, every other day, or daily. In particular aspects, the injection is administered subcutaneously. In other aspects, the injection is administered intravenously.

In some embodiments, the composition comprising ADAMTS13 is administered to the subject before the onset of the VOC to prevent the VOC. In such aspects of the disclosure, the composition is administered in a therapeutically effective amount or dose sufficient to maintain an effective level of ADAMTS13 activity in the subject or in the blood of the subject.

The disclosure includes methods for treating, ameliorating, or preventing ALI or ARDS in a subject, including administering an effective amount of ADAMTS13 or an ADAMTS13 composition as described herein. The composition is introduced into the subject to be treated by any conventional method as described herein in detail above. In certain aspects, the composition is administered in a single dose or a plurality of doses over a period of time (as described in more detail below).

In some embodiments, the composition comprising ADAMTS13 is administered to the subject within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 60, 72, 84, 96, 108, or 120 hours after the onset of the ALI or ARDS. In some embodiments, the composition comprising ADAMTS13 is administered to the subject within about 1-2 hours, about 1-5 hours, about 1-10 hours, about 1-12 hours, about 1-24 hours, about 1-36 hours, about 1-48 hour, about 1-60 hours, about 1-72 hours, about 1-84 hours, about 1-96 hours, about 1-108 hours, or about 1-120 hours after the onset of the ALI or ARDS. In some embodiments, the composition comprising ADAMTS13 is administered to the subject within about 2-5 hours, about 5-10 hours, about 10-20 hours, about 20-40 hours, about 30-60 hours, about 40-80 hours, about 50-100 hours, or about 60-120 hours after the onset of the ALI or ARDS. In some embodiments, the composition is administered within 4 hours, within 8 hours, within 12 hours, within 1 day, within 2 days, within 3 days, within 4 days, within 5 days, within 6 days after the onset or diagnosis of the ALI or ARDS. In some embodiments, the composition is administered within 1 week after the onset or diagnosis of the ALI or ARDS. In some embodiments, the composition is administered daily after the onset or diagnosis of ALI or ARDS. In some embodiments, the composition is administered weekly after the onset or diagnosis of ALI or ARDS. In some embodiments, the composition is administered every day. In some embodiments, the composition is administered every other day. In some embodiments, the composition is administered every third day. In some embodiments, the composition is administered twice a week. In some embodiments, the composition is administered until the clinical manifestations resolve. In some embodiments, the composition is administered until a day after clinical manifestations resolve. In some embodiments, the composition is administered for at least two days after clinical manifestations resolve. In some embodiments, the composition is administered for at least three days after clinical manifestations resolve. In some embodiments, the composition is administered for at least a week after clinical manifestations resolve.

In some aspects, the composition comprising ADAMTS13 is administered to the subject to prevent the onset of ALI or ARDS. In such preventative treatment, ADAMTS13 is administered in a singular bolus injection or in multiple doses to maintain a circulating level of ADAMTS13 effective to prevent the onset of the ALI or ARDS. In such aspects, the composition comprising ADAMTS13 is administered monthly, every two weeks, weekly, twice a week, every other day, or daily. In particular aspects, the injection is administered subcutaneously. In other aspects, the injection is administered intravenously.

In some embodiments, the composition comprising ADAMTS13 is administered to the subject before the onset of the ALI or ARDS to prevent the ALI or ARDS. In such aspects of the disclosure, the composition is administered in a therapeutically effective amount or dose sufficient to maintain an effective level of ADAMTS13 activity in the subject or in the blood of the subject.

Dosing of ADAMTS13 Compositions/Methods of Treating

In various aspects, the effective dosage of ADAMTS13 or an ADAMTS13 composition to be administered varies depending on multiple factors which modify the action of drugs, e.g. the age, condition, body weight, sex, and diet of the subject, the severity of any infection, time of administration, mode of administration, and other clinical factors, including the severity of the VOC of the SCD.

In some aspects, formulations or compositions of the disclosure are administered by an initial bolus followed by booster delivery after a period of time has elapsed. In certain aspects, formulations of the disclosure are administered by an initial bolus followed by a continuous infusion to maintain therapeutic circulating levels of ADAMTS13. In particular aspects, ADAMTS13 or an ADAMTS13 composition of the disclosure is administered over extended periods of time. In some aspects, the ADAMTS13 or ADAMTS13 composition is delivered in a rapid treatment regimen to relieve acute symptoms of VOC. In some aspects, the ADAMTS13 or ADAMTS13 composition is delivered in a prolonged and varied treatment regimen to prevent the occurrence of VOC. As another example, the composition or formulation of the disclosure is administered as a one-time dose. Those of ordinary skill in the art readily optimize effective dosages and administration regimens as determined by good medical practice and the clinical condition of the individual subject. The frequency of dosing depends on the pharmacokinetic parameters of the agents, the route of administration, and the condition of the subject.

The pharmaceutical formulation is determined by one skilled in the art depending upon the route of administration and desired dosage. See for example, Remington's Pharmaceutical Sciences, 18th Ed. (1990, Mack Publishing Co., Easton, Pa. 18042) pages 1435-1712, the disclosure of which is hereby incorporated by reference for all purposes. Such formulations, in some instances, influence the physical state, stability, rate of in vivo release, and rate of in vivo clearance of the administered composition. Depending on the route of administration, a suitable dose is calculated, in particular aspects, according to body weight, body surface area or organ size. In some aspects, appropriate dosages are ascertained through use of established assays for determining blood level dosages in conjunction with appropriate dose-response data. In certain aspects, the antibody titer of an individual is measured to determine optimal dosage and administration regimens. The final dosage regimen will be determined by the attending doctor or physician, considering various factors which modify the action of the pharmaceutical compositions, e.g. the composition's specific activity, the responsiveness of the subject, the age, condition, body weight, sex and diet of the subject, the severity of any infection or malignant condition, time of administration and other clinical factors, including the severity of the pain or the VOC.

In certain aspects, the ADAMTS13 or ADAMTS13 composition comprises any dose of ADAMTS13 sufficient to evoke a response in the subject. In some embodiments, the dose of ADAMTS13 is sufficient to treat VOC. In some embodiments, the dose of ADAMTS13 is sufficient to prevent VOC. In some embodiments, the dose of ADAMTS13 is sufficient to treat ALI. In some embodiments, the dose of ADAMTS13 is sufficient to prevent ALI. In some embodiments, the dose of ADAMTS13 is sufficient to treat ARDS. In some embodiments, the dose of ADAMTS13 is sufficient to prevent ARDS. The effective amount of ADAMTS13 or ADAMTS13 composition to be employed therapeutically will depend, for example, upon the therapeutic context and objectives. One skilled in the art will appreciate that the appropriate dosage levels for treatment or prevention will thus vary depending, in part, upon the molecule delivered, the indication for which the ADAMTS13 or ADAMTS13 composition is being used, the route of administration, and the size (body weight, body surface or organ size) and condition (the age and general health) of the patient. Accordingly, the clinician, in some instances, titers the dosage and modifies the route of administration to obtain the optimal therapeutic effect.

Dosage, unless otherwise specifically recited, is provided in international units. As discussed herein below, the use of international units (IU) is the new standard for measuring ADAMTS13 activity. Up until recently, FRETS units (or FRETS test units) were the standard for measuring ADAMTS13 activity. 20 FRETS units (FRETS U) is equivalent to approximately 21.78 IU. In other words, 20 IU of ADAMTS13 is equivalent to about 18.22 FRETS U of ADAMTS13.

A typical dosage, in various aspects, ranges from about 10 international units per kilogram body weight up to about 10,000 international units per kilogram body weight. In some aspects, a dosage or therapeutically effective amount of ADAMTS13 is up to about 10,000 international units per kilogram body weight or more, depending on the factors mentioned above. In other aspects, the dosage may range from about 20 to about 6,000 international units per kilogram body weight. In some aspects, the dosage or therapeutically effective amount of ADAMTS13 is from about 40 to about 4,000 international units per kilogram body weight. In some aspects, the dosage or therapeutically effective amount is from about 100 to about 3,000 international units per kilogram body weight.

In particular aspects, the dosage or therapeutically effective amount is from about 10 to about 500 international units per kilogram body weight. In some aspects, the dosage or therapeutically effective amount is from about 50 to about 450 international units per kilogram body weight. In some aspects, the therapeutically effective amount is from about 40 to about 100 international units per kilogram body weight. In some aspects, the therapeutically effective amount is from about 40 to about 150 international units per kilogram body weight. In some aspects, the dosage or therapeutically effective amount is from about 100 to about 500 international units per kilogram body weight. In some aspects, the dosage or therapeutically effective amount is from about 100 to about 400 international units per kilogram body weight. In some aspects, the dosage or therapeutically effective amount is from about 100 to about 300 international units per kilogram body weight. In some aspects, the dosage or therapeutically effective amount is from about 300 to about 500 international units per kilogram body weight. In some aspects, the dosage or therapeutically effective amount is from about 200 to about 300 international units per kilogram body weight. In some aspects, the dosage or therapeutically effective amount is about 100, about 150, about 200, about 250, about 300, about 350, about 400, about 450, or about 500 international units per kilogram body weight.

In further aspects, the dosage or therapeutically effective amount is from about 50 to about 1,000 international units per kilogram body weight. In some aspects, the dosage or therapeutically effective amount is from about 100 to about 900 international units per kilogram body weight. In some aspects, the dosage or therapeutically effective amount is from about 200 to about 800 international units per kilogram body weight. In some aspects, the dosage or therapeutically effective amount is from about 300 to about 700 international units per kilogram body weight. In some aspects, the dosage or therapeutically effective amount is from about 400 to about 600 international units per kilogram body weight. In some aspects, the dosage or therapeutically effective amount is about 500 international units per kilogram body weight.

In some aspects, the dosage or therapeutically effective amount is about 10 international units per kilogram body weight, about 20 international units per kilogram body weight, about 30 international units per kilogram body weight, about 40 international units per kilogram body weight, about 50 international units per kilogram body weight, about 60 international units per kilogram body weight, about 70 international units per kilogram body weight, about 80 international units per kilogram body weight, about 90 international units per kilogram body weight, about 100 international units per kilogram body weight, about 120 international units per kilogram body weight, about 140 international units per kilogram body weight, about 150 international units per kilogram body weight, about 160 international units per kilogram body weight, about 180 international units per kilogram body weight, about 200 international units per kilogram body weight, about 220 international units per kilogram body weight, about 240 international units per kilogram body weight, about 250 international units per kilogram body weight, about 260 international units per kilogram body weight, about 280 international units per kilogram body weight, about 300 international units per kilogram body weight, about 350 international units per kilogram body weight, about 400 international units per kilogram body weight, about 450 international units per kilogram body weight, about 500 international units per kilogram body weight, about 550 international units per kilogram body weight, about 600 international units per kilogram body weight, about 650 international units per kilogram body weight, about 700 international units per kilogram body weight, about 750 international units per kilogram body weight, about 800 international units per kilogram body weight, about 850 international units per kilogram body weight, about 900 international units per kilogram body weight, about 950 international units per kilogram body weight, about 1,000 international units per kilogram body weight, about 1,100 international units per kilogram body weight, about 1,100 international units per kilogram body weight, about 1,200 international units per kilogram body weight, about 1,300 international units per kilogram body weight, about 1,400 international units per kilogram body weight, about 1,500 international units per kilogram body weight, about 1,600 international units per kilogram body weight, about 1,800 international units per kilogram body weight, about 2,000 international units per kilogram body weight, about 2,500 international units per kilogram body weight, about 3,000 international units per kilogram body weight, about 3,500 international units per kilogram body weight, about 4,000 international units per kilogram body weight, about 4,500 international units per kilogram body weight, about 5,000 international units per kilogram body weight, about 5,500 international units per kilogram body weight, about 6,000 international units per kilogram body weight, about 6,500 international units per kilogram body weight, about 7,000 international units per kilogram body weight, about 7,500 international units per kilogram body weight, about 8,000 international units per kilogram body weight, about 8,500 international units per kilogram body weight, about 9,000 international units per kilogram body weight, about 9,500 international units per kilogram body weight, and about 10,000 international units per kilogram body weight.

As used herein, "one unit of ADAMTS13 activity" or "one activity unit" is defined as the amount of activity in 1 mL of pooled normal human plasma, regardless of the assay being used. As provided above, however, the new standard for measuring or dosing ADAMTS13 is international units (IU). 20 FRETS test units or 20 FRETS units (FRETS U) is equivalent to approximately 21.78 IU. In other words, 20 IU of ADAMTS13 is equivalent to about 18.22 FRETS U of ADAMTS13. Thus, the change to the new standard results in an approximate shift of 8.9% in the conversion of FRETS U to IU.

In some aspects, Fluorescence Resonance Energy Transfer (FRETS) assays are used to measure ADAMTS13 activity. FRETS requires two interacting partners of which one is labeled with a donor fluorophore and the other is labeled with an acceptor fluorophore. FRETS assays for ADAMTS13 involve a chemically modified fragment of the A2 domain of VWF which spans the ADAMTS13 cleavage site. This is readily cleaved by normal plasma but not by ADAMTS13 deficient plasma. This cleavage is blocked by EDTA and so samples for this assay must be collected into tubes that contain citrate as an anticoagulant and not EDTA. One unit of ADAMTS13 FRETS-VWF73 activity is the amount of activity needed to cleave the same amount of FRETS-VWF73 substrate (Kokame et al., Br J. Haematol. 2005 April; 129(1):93-100, incorporated herein by reference) as is cleaved by one mL of pooled normal human plasma.

In some aspects, additional activity assays are used for measuring the activity of ADAMTS13. For example, direct ADAMTS13 activity assays can be performed to detect the cleavage of either full-length VWF molecules or VWF fragments using SDS agarose gel electrophoresis and indirect detection of ADAMTS13 activity can be detected with collagen binding assays. Direct assays, including the FRETS assay, as described herein, involve the detection of cleavage of products either of a full-length VWF molecule or a VWF fragment that encompasses the ADAMTS13 cleavage site. With SDS Agarose Gel electrophoresis and Western Blotting, purified VWF is incubated with plasma for 24 hours. Cleavage of the VWF by ADAMTS13 takes place leading to a reduction in multimer sizes. This reduction is visualized by agarose gel electrophoresis followed by Western blotting with a peroxidase-conjugated anti-VWF antibody. The concentration of ADAMTS13 activity in the test sample can be established by reference to a series of diluted normal plasma samples. SDS-PAGE and Western Blotting can also be carried out, which involves the visualization of dimeric VWF fragments following SDS PAGE and Western Blotting. The assay is technically easier than SDS agarose gel electrophoresis and appears a very sensitive method for measuring ADAMTS13 activity levels.

In some aspects, indirect assays involve the detection of cleavage of products either of a full-length VWF molecule or a VWF fragment that encompasses the ADAMTS13 cleavage site in the A2 domain of VWF. Such assays include collagen binding assays, where normal plasma or purified VWF is incubated with the test plasma sample in the presence of BaCl2 and 1.5M urea which denatures the VWF. VWF is cleaved by ADAMTS13 and residual VWF is measured by its binding to collagen Type III. The bound VWF is quantitated using an ELISA assay with a conjugated anti-VWF antibody. Another indirect assay is the ristocetin-induced aggregation assay. This is similar to the collagen-binding assay above but residual VWF is measured by ristocetin-induced platelet aggregation using a platelet aggregometer. Another indirect assay is a functional ELISA. In this assay, a recombinant VWF fragment is immobilized onto an ELISA plate using an antibody to a tag on the VWF. The VWF fragment encodes the A2 domain and the ADAMTS13 cleavage site at Tyr1605-Met1606 and is tagged with S-transferase [GST]-histidine [GST-VWF73-His]. Plasma is added to the immobilized GST-VWF73-His fragment and cleavage of the immobilized fragment occurs at the ADAMTS13 cleavage site. The residual, cleaved VWF fragment is measured by using a second monoclonal antibody that recognizes only the cleaved VWF fragment and NOT the interact fragment. ADAMTS13 activity is, therefore, inversely proportional to the residual substrate concentration.

In certain embodiments, ADAMTS13 is provided or administered in a therapeutically effective concentration between about 0.05 mg/mL and about 10 mg/mL in the final formulation. In other embodiments, ADAMTS13 is present at a concentration of between about 0.1 mg/mL and about 10 mg/mL. In yet other embodiments, ADAMTS13 is present at a concentration of between about 0.1 mg/mL and about 5 mg/mL. In another embodiment, ADAMTS13 is present at a concentration of between about 0.1 mg/mL and about 2 mg/mL. In yet other embodiments, ADAMTS13 may be present at about 0.01 mg/mL, or at about 0.02 mg/mL, 0.03 mg/mL, 0.04 mg/mL, 0.05 mg/mL, 0.06 mg/mL, 0.07 mg/mL, 0.08 mg/mL, 0.09 mg/mL, 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 1.1 mg/mL, 1.2 mg/mL, 1.3 mg/mL, 1.4 mg/mL, 1.5 mg/mL, 1.6 mg/mL, 1.7 mg/mL, 1.8 mg/mL, 1.9 mg/mL, 2.0 mg/mL, 2.5 mg/mL, 3.0 mg/mL, 3.5 mg/mL, 4.0 mg/mL, 4.5 mg/mL, 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10.0 mg/mL, or a higher concentration.

In some embodiments, the concentration of a relatively pure ADAMTS13 formulation may be determined by spectroscopy (i.e., total protein measured at A280) or other bulk determination (e.g., Bradford assay, silver stain, weight of a lyophilized powder, etc.). In other embodiments, the concentration of ADAMTS13 may be determined by an ADAMTS13 ELISA assay (e.g., mg/mL antigen).

In some aspects, the concentration of ADAMTS13 in a formulation of the disclosure is expressed as a level of enzymatic activity. For example, in some embodiments, an ADAMTS13 formulation contains between about 10 units of FRETS-VWF73 activity and about 10,000 units of FRETS-VWF73 activity or other suitable ADAMTS13 enzymatic unit (IU). In other embodiments, the formulation may contain between about 20 units of FRETS-VWF73 ($U_{FV73}$) activity and about 8,000 units of FRETS-VWF73 activity, or between about 30 $U_{FV73}$ and about 6,000 $U_{FV73}$, or between about 40 $U_{FV73}$ and about 4,000 $U_{FV73}$, or between about 50 $U_{FV73}$ and about 3,000 $U_{FV73}$, or between about 75 $U_{FV73}$ and about 2,500 $U_{FV73}$, or between about 100 $U_{FV73}$ and about 2,000 $U_{FV73}$, or between about 200 $U_{FV73}$ and about 1,500 $U_{FV73}$, or between about other ranges therein.

In some embodiments, ADAMTS13 is provided or administered at a dose of from about 10 $U_{FV73}$/kg body weight to 10,000 $U_{FV73}$/kg body weight. In one embodiment, ADAMTS13 is administered at a dose of from about 20 $U_{FV73}$/kg body weight to about 8,000 $U_{FV73}$/kg body weight. In one embodiment, ADAMTS13 is administered at a dose of from about 30 $U_{FV73}$/kg body weight to about 6,000 $U_{FV73}$/kg body weight. In one embodiment, ADAMTS13 is administered at a dose of from about 40 $U_{FV73}$/kg body weight to about 4,000 $U_{FV73}$/kg body weight. In one embodiment, ADAMTS13 is administered at a dose of from about 100 $U_{FV73}$/kg body weight to about 3,000 $U_{FV73}$/kg body weight. In one embodiment, ADAMTS13 is administered at a dose of from about 200 $U_{FV73}$/kg body weight to about 2,000 $U_{FV73}$/kg body weight. In other embodiments, ADAMTS13 is administered at about 10 $U_{FV73}$/kg body weight, about 20, 30, 40, 50, 60, 70, 80, 90, 100, 150, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,500, 5,000, 5,500, 6,000, 6,500, 7,000, 7,500, 8,000, 8,500, 9,000, 9,500, or 10,000 $U_{FV73}$/kg body weight, or at an intermediate dose or dose range thereof.

In some aspects, an ADAMTS13 formulation provided herein contains between about 20 and about 10,000 $U_{FV73}$. In some embodiments, a formulation contains about 10 units of FRETS-VWF73 activity, or about 20, 30, 40, 50, 60, 70, 80, 90, 100, 150, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 6,100, 6,200, 6,300, 6,400, 6,500, 6,600, 6,700, 6,800, 6,900, 7,000, 7,100, 7,200, 7,300, 7,400, 7,500, 7,600, 7,700, 7,800, 7,900, 8,000, 8,100, 8,200, 8,300, 8,400, 8,500, 8,600, 8,700, 8,800, 8,900, 9,000, 9,100, 9,200, 9,300, 9,400, 9,500, 9,600, 9,700, 9,800, 9,900, 10,000 or more units of FRETS-VWF73 activity.

In some aspects, the concentration of ADAMTS13 may be expressed as an enzymatic activity per unit volume, for example, ADAMTS13 enzymatic units per mL (IU/mL). For example, in some embodiments, an ADAMTS13 formulation contains between about 10 IU/mL and about 10,000 IU/mL. In some other embodiments, the formulation contains between about 20 IU/mL and about 10,000 IU/mL, or between about 20 IU/mL and about 8,000 IU/mL, or between about 30 IU/mL and about 6,000 IU/mL, or between about 40 IU/mL and about 4,000 IU/mL, or between about 50 IU/mL and about 3,000 IU/mL, or between about 75 IU/mL and about 2,500 IU/mL, or between about 100 IU/mL and about 2,000 IU/mL, or between about 200 IU/mL and about 1,500 IU/mL, or between about other ranges therein. In some embodiments, an ADAMTS13 formulation provided herein contains between about 150 IU/mL and about 600 IU/mL. In another embodiment, an ADAMTS13 formulation provided herein contains between about 100 IU/mL and about 1,000 IU/mL. In some embodiments, an ADAMTS13 formulation provided herein contains between about 100 IU/mL and about 800 IU/mL. In some embodiments, an ADAMTS13 formulation provided herein contains between about 100 IU/mL and about 600 IU/mL. In some embodiments, an ADAMTS13 formulation provided herein contains between about 100 IU/mL and about 500 IU/mL. In some embodiments, an ADAMTS13 formulation provided herein contains between about 100 IU/mL and about 400 IU/mL. In some embodiments, an ADAMTS13 formulation provided herein contains between about 100 IU/mL and about 300 IU/mL. In some embodiments, an ADAMTS13 formulation provided herein contains between about 100 IU/mL and about 200 IU/mL. In some embodiments, an ADAMTS13 formulation provided herein contains between about 300 IU/mL and about 500 IU/mL. In some embodiments, an ADAMTS13 formulation provided herein contains about 100 IU/mL. In some embodiments, an ADAMTS13 formulation provided herein contains about 300 IU/mL. In various embodiments, a formulation contains about 10 IU/mL, or about 20, 30, 40, 50, 60, 70, 80, 90, 100, 150, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 6,100, 6,200, 6,300, 6,400, 6,500, 6,600, 6,700, 6,800, 6,900, 7,000, 7,100, 7,200, 7,300, 7,400, 7,500, 7,600, 7,700, 7,800, 7,900, 8,000, 8,100, 8,200, 8,300, 8,400, 8,500, 8,600, 8,700, 8,800, 8,900, 9,000, 9,100, 9,200, 9,300, 9,400, 9,500, 9,600, 9,700, 9,800, 9,900, 10,000 or more IU/mL.

In some embodiments, the ADAMTS13 formulations provided herein may further comprise one or more pharmaceutically acceptable excipients, carriers, and/or diluents as described in U.S. Patent Application Publication No. 2011/0229455 and/or in U.S. Patent Application Publication No. 2014/0271611, each of which incorporated by reference in their entirety for all purposes. Furthermore, in one embodiment, the ADAMTS13 formulations provided herein will have a tonicity in a range described in as described in U.S. Patent Application Publication No. 2011/0229455 and/or in U.S. Patent Application Publication No. 2014/0271611, each of which incorporated by reference in their entirety for all purposes.

The frequency of dosing will depend upon the pharmacokinetic parameters of the ADAMTS13 molecule in the formulation used. Typically, a clinician will administer the composition until a dosage is reached that achieves the desired effect. The composition, in various aspects, is therefore administered as a single dose, or as two or more doses (which may or may not contain the same amount of the desired molecule) over time, or as a continuous infusion via an implantation device or catheter. In some aspects, the composition comprising ADAMTS13 is administered in a single bolus injection, monthly, every two weeks, weekly, twice a week, every other day, daily, every 12 hours, every eight hours, every six hours, every four hours, or every two hours. In the prophylactic or preventative treatment aspects of the disclosure, ADAMTS13 is administered in multiple doses to maintain a circulating level of ADAMTS13 effective to prevent the onset of the VOC, ALI, or ARDS. In such aspects, the composition comprising ADAMTS13 is administered monthly, every two weeks, weekly, twice a week, every other day, or daily. In particular aspects, the injection is administered subcutaneously (e.g., WO2014151968, incorporated herein by reference in its entirety for all purposes). In other aspects, the injection is administered intravenously. Further refinement of the appropriate dosage administered and the timing of administration is routinely made by those of ordinary skill in the art and is within the ambit of tasks routinely performed by them. Appropriate dosages are often ascertained through use of appropriate dose-response data which is routinely obtained.

Kits Comprising ADAMTS13

As an additional aspect, the disclosure includes kits which comprise one or more pharmaceutical formulations for administration of ADAMTS13 or an ADAMTS13 composition to a subject packaged in a manner which facilitates their use for administration to the subject.

In a specific embodiment, the disclosure includes kits for producing a single dose administration unit. In another embodiment, the disclosure includes kits for providing multiple dose administration units. The kits, in various aspects, each contain both a first container having a dried protein and a second container having an aqueous formulation. Also included within the scope of this disclosure are kits containing single and multi-chambered pre-filled syringes (e.g., liquid syringes and lyosyringes).

In another embodiment, such a kit includes a pharmaceutical formulation described herein (e.g., a composition comprising a therapeutic protein, e.g., ADAMTS13), packaged in a container such as a sealed bottle or vessel, with a label affixed to the container or included in the package that describes use of the compound or composition in practicing the method. In one embodiment, the pharmaceutical formulation is packaged in the container such that the amount of headspace in the container (e.g., the amount of air between the liquid formulation and the top of the container) is very small. Preferably, the amount of headspace is negligible (i.e., almost none).

In some aspects, the pharmaceutical formulation or composition comprises a stabilizer. The term "stabilizer" refers to a substance or excipient which protects the composition from adverse conditions, such as those which occur during heating or freezing, and/or prolongs the stability or shelf-life of the composition or pharmaceutical composition in a stable state. Examples of stabilizers include, but are not limited to, sugars, such as sucrose, lactose and mannose; sugar alcohols, such as mannitol; amino acids, such as glycine or glutamic acid; and proteins, such as human serum albumin or gelatin.

In some aspects, the pharmaceutical formulation or composition comprises an antimicrobial preservative. The term "antimicrobial preservative" refers to any substance which is added to the composition that inhibits the growth of microorganisms that may be introduced upon repeated puncture of multidose vials, should such containers be used. Examples of antimicrobial preservatives include, but are not limited to, substances such as thimerosal, 2-phenoxyethanol, benzethonium chloride, and phenol.

In one aspect, the kit contains a first container having a therapeutic protein or protein composition and a second container having a physiologically acceptable reconstitution solution for the composition. In one aspect, the pharmaceutical formulation is packaged in a unit dosage form. The kit optionally further includes a device suitable for administering the pharmaceutical formulation according to a specific route of administration. In some aspects, the kit contains a label that describes use of the pharmaceutical formulations.

This entire document is intended to be related as a unified disclosure, and it should be understood that all combinations of features described herein are contemplated, even if the combination of features are not found together in the same sentence, or paragraph, or section of this document. The disclosure also includes, for instance, all embodiments of the disclosure narrower in scope in any way than the variations specifically mentioned above.

All publications, patents and patent applications cited in this specification are herein incorporated by reference as if each individual publication or patent application were specifically and individually indicated to be incorporated by reference in its entirety to the extent that it is not inconsistent with the disclosure.

Additional Embodiments

In certain embodiments, provided is a method for treating or preventing a vaso-occlusive crisis (VOC) in a subject suffering from sickle cell disease (SCD). A therapeutically effective amount of a composition comprising ADAMTS13 is administered to the subject. The subject may be a human patient with SCD, or an animal with SCD. The ADAMTS13 may be in a recombinant form. ADAMTS13 may be part of a formulation suitable for intravenous injection. ADAMTS13 may be part of a formulation suitable for subcutaneous injection. The dosage of ADAMTS13 may be from 2,500 IU/kg to 4,000 IU/kg, from 2,800 IU/kg to 3,800 IU/kg, from 3,000 IU/kg to 3,400 IU/kg, about 3,200 IU/kg, or 3,200 IU/kg in a rodent. The dosage of ADAMTS13 may be from 40 IU/kg to 100 IU/kg, from 100 IU/kg to 300 IU/kg, from 120 IU/kg to 240 IU/kg, from 150 IU/kg to 200 IU/kg, or from 300 IU/kg to 500 IU/kg in a human patient. The ADAMTS13 may be administered intravenously at a time before, during or after an acute VOC in a human patient, or an animal patient, having SCD. The ADAMTS13 may be administered subcutaneously at a time before, during or after an acute VOC in a human patient, or an animal patient, having SCD. The treatment may be effective to protect the subject, e.g., a human patient or animal with SCD, from morbidity and mortality associated with VOC or hypoxia.

In certain embodiments, provided is a method for treating or preventing acute lung injury (ALI) or acute respiratory distress syndrome (ARDS). A therapeutically effective amount of a composition comprising ADAMTS13 is administered to the subject. The ADAMTS13 may be in a recombinant form. ADAMTS13 may be part of a formulation suitable for intravenous injection. ADAMTS13 may be part of a formulation suitable for subcutaneous injection. The dosage of ADAMTS13 may be from 2,500 IU/kg to 4,000 IU/kg, from 2,800 IU/kg to 3,800 IU/kg, from 3,000 IU/kg to 3,400 IU/kg, about 3,200 IU/kg, or 3,200 IU/kg in a rodent. The dosage of ADAMTS13 may be from 40 IU/kg to 100 IU/kg, from 100 IU/kg to 300 IU/kg, from 120 IU/kg to 240 IU/kg, from 150 IU/kg to 200 IU/kg, or from 300 IU/kg to 500 IU/kg in a human patient. The ADAMTS13 may be administered intravenously at a time before, during or after an ALI or ARDS in a human patient, or an animal patient. The ADAMTS13 may be administered subcutaneously at a time before, during or after an ALI or ARDS in a human patient, or an animal patient. The treatment may be effective to protect the subject, e.g., a human patient or ALI and/or ARDS, from morbidity and mortality.

In another embodiment, provided is a method for treating, ameliorating, or preventing (a) a VOC in a subject suffering from SCD or (b) a lung injury in a subject suffering from or at risk of suffering from acute lung injury (ALI) and/or acute respiratory distress syndrome (ARDS). A therapeutically effective amount of ADAMTS13 is administered to the subject. The lung injury or vascular inflammation may be secondary to, or induced by, hypoxia. The lung injury or vascular inflammation may be secondary to, or induced by, reoxygenation stress. During hypoxia or reoxygenation stress, the level of oxygen may be about 7%, about 8%, about 9%, about 10%, 7-10%, or 7-9%. The subject may be a human patient with SCD, a human patient experiencing a VOC, a human patient with an ALI, a human patient with ARDS, an animal with SCD, an animal experiencing VOC, an animal with ALI, an animal with ARDS, or an animal homozygous for HbA. ADAMTS13 may be part of a formulation suitable for intravenous injection. ADAMTS13 may be part of a formulation suitable for subcutaneous injection. The dosage of ADAMTS13 may be from 2,500 IU/kg to 4,000 IU/kg, from 2,800 IU/kg to 3,800 IU/kg, from 3,000 IU/kg to 3,400 IU/kg, about 3,200 IU/kg, or 3,200 IU/kg in a rodent. The dosage of ADAMTS13 may be from 40 IU/kg to 100 IU/kg, 100 IU/kg to 300 IU/kg, from 120 IU/kg to 240 IU/kg, from 150 IU/kg to 200 IU/kg, or from 300 IU/kg to 500 IU/kg in a human patient. The subject may be monitored for one or more of BAL protein content and BAL leukocyte count at one or more times before, during, and after treatment. Administration of ADAMTS13 may be effective to decrease BAL protein content by at least 35%, at least 36%, at least 37%, at least 38%, at least 39%, at least 40%, 30-45%, 33-43%, 34-42%, 35-41%, or 36-40%, in comparison with a control (e.g., untreated subject). Administration of ADAMTS13 may be effective to decrease BAL leukocyte count by at least 35%, at least 36%, at least 37%, at least 38%, at least 39%, at least 40%, 30-45%, 33-43%, 34-42%, 35-41%, or 36-40%, in comparison with control (e.g., untreated subject).

In at least the above embodiments, administration of ADAMTS13 may be effective to prevent activation or increased expression or level of at least one of VCAM-1 and ICAM-1 and/or to reduce the expression of at least one of ET-1, TXAS and HO-1. See, FIGS. 2B, 2C, and 3B. Administration of ADAMTS13 may be effective to decrease the expression or level of TXAS or ET-1, as measured by densitometry for example, by at least 65%, at least 68%, at least 71%, at least 74%, at least 77%, at least 80%, 65-80%, 70-80%, or 70-75%, in comparison with a control (e.g., untreated subject). Administration of ADAMTS13 may be effective to decrease the expression or level or activity of ICAM-1, as measured by densitometry for example, by at least 53%, at least 56%, at least 59%, at least 62%, at least 65%, 53-65%, 55-62%, or 57-60%, in comparison with a control (e.g., untreated subject). Administration of ADAMTS13 may be effective to decrease the expression or level of HO-1, as measured by densitometry for example, by at least 46%, at least 47%, at least 48%, at least 49%, 46-49%, 47-49%, or 46-48%, in comparison with a control (e.g., untreated subject). Administration of ADAMTS13 may be effective to decrease the ratio of P-NF-kB/NF-kB, as measured by densitometry for example, by at least 63%, at least 67%, at least 71%, at least 75%, at least 79%, at least 83%, 63-83%, 67-79%, or 71-75%, in comparison with a control (e.g., untreated subject). In a subject with SCD or experiencing VOC, administration of ADAMTS13 may be effective to decrease the expression, level or activity of VCAM-1, as measured by densitometry for example, by at least 40%, at least 42%, at least 44%, at least 46%, at least 48%, at least 50%, 40-50%, 42-48%, or 44-46%, in comparison with a control (e.g., untreated subject). In certain embodiments, the biomarker (e.g., VCAM-1, ICAM-1, P-NF-kB, NF-kB, ET-1, TXAS and HO-1) is measured in the lung. In certain embodiments, the biomarker (e.g., VCAM-1, ICAM-1, P-NF-kB, NF-kB, ET-1, TXAS and HO-1) is measured in the kidney.

In at least the above embodiments, with respect to treating lung injury or vascular inflammation associated with SCD, VOC, ALI, and/or ARDS, administration of ADAMTS13 may be effective to prevent activation or increased expression or level of at least one of VCAM-1 and ICAM-1 and/or to reduce the expression or level of at least one of ET-1, TXAS, and HO-1. See, FIGS. 2B and 2C. Administration of ADAMTS13 may be effective to decrease the expression or level of TXAS or ET-1, as measured by densitometry for example, by at least 65%, at least 68%, at least 71%, at least 74%, at least 77%, at least 80%, 65-80%, 70-80%, or 70-75%, in comparison with a control (e.g., untreated subject). Administration of ADAMTS13 may be effective to decrease the expression or level or activity of ICAM-1, as measured by densitometry for example, by at least 53%, at least 56%, at least 59%, at least 62%, at least 65%, 53-65%, 55-62%, or 57-60%, in comparison with a control (e.g., untreated subject). Administration of ADAMTS13 may be effective to decrease the expression or level of HO-1, as measured by densitometry for example, by at least 46%, at least 47%, at least 48%, at least 49%, 46-49%, 47-49%, or 46-48%, in comparison with a control (e.g., untreated subject). Administration of ADAMTS13 may be effective to decrease the ratio of P-NF-kB/NF-kB, as measured by densitometry for example, by at least 63%, at least 67%, at least 71%, at least 75%, at least 79%, at least 83%, 63-83%, 67-79%, or 71-75%, in comparison with a control (e.g., untreated subject). In a subject with SCD and/or experiencing a VOC, administration of ADAMTS13 may be effective to decrease the expression nor level or activity of VCAM-1, as measured by densitometry for example, by at least 40%, at least 42%, at least 44%, at least 46%, at least 48%, at least 50%, 40-50%, 42-48%, or 44-46%, in comparison with a control (e.g., untreated subject). In certain embodiments, the biomarker (e.g., VCAM-1, ICAM-1, P-NF-kB, NF-kB, ET-1, TXAS and HO-1) is measured in the lung.

In at least the above embodiments, with respect to treating kidney injury or vascular inflammation associated with SCD, VOC, ALI, and/or ARDS, administration of ADAMTS13 may be effective to prevent activation and/or increased expression levels of VCAM-1, decrease the ratio of P-NF-kB/NF-kB and/or to reduce the expression or level of at least one of ET-1 or TXAS. See FIGS. 3A and 3B. Administration of ADAMTS13 may be effective to decrease the expression nor level of TXAS, as measured by densitometry for example, by at least 70%, at least 73%, at least 76%, at least 78%, at least 80%, at least 82%, 70-82%, 73-80%, or 76-78%, in comparison with a control (e.g., untreated subject). Administration of ADAMTS13 may be effective to decrease the ratio of P-NF-kB/NF-kB, as measured by densitometry for example, by at least 68%, at least 70%, at least 72%, at least 75%, at least 78%, 68-78%, 70-75%, or 72-75%, in comparison with a control (e.g., untreated subject). Administration of ADAMTS13 may be effective to decrease the expression or level or activity of VCAM-1 in a subject with SCD or experiencing VOC, as measured by densitometry for example, by at least 58%, at least 60%, at least 62%, at least 64%, at least 67%, 58-67%, 60-64%, or 60-62%, in comparison with a control (e.g., untreated subject). In certain embodiments, the biomarker (e.g., VCAM-1, P-NF-kB, NF-kB, ET-1, TXAS and HO-1) is measured in the kidney.

In at least the above embodiments, a sample of blood from the subject may be taken, for example to monitor the treatment of SCD, VOC, ALI, and/or ARDS, with one or more of the following hematocrit values measured: % hematocrit (Hct) and mean corpuscular volume (MCV), as indicators of erythrocyte viability; hemoglobin (Hb), mean corpuscular hemoglobin (MCH), and cell hemoglobin concentration mean (CHCM), as indicators of oxygen binding capacity; heterogeneity of red cell distribution (HDW), as an indicator of presence of dense red cells; reticulocyte count (Retics), as an indicator of anemia status; neutrophil count, as an indicator of the systemic inflammatory status; and/or lactate dehydrogenase (LDH) as a general marker of cell damage. Administration of ADAMTS13 may be effective to decrease CHCM by at least 5%, at least 5.5%, at least 6%, at least 6.5%, or at least 7%, in comparison with a control (e.g., untreated subject). Administration of ADAMTS13 may be effective to increase retics by at least 5%, at least 7%, at least 9%, at least 11%, or at least 13%, in comparison with a control (e.g., untreated subject). Administration of ADAMTS13 may be effective to decrease neutrophils (cells/microliter) by at least 30%, at least 35%, at least 40%, at least 45%, or at least 50%, in comparison with a control (e.g., untreated subject). Administration of ADAMTS13 may be effective to decrease LDH (cells/microliter) by at least 5%, at least 10%, at least 15%, at least 20%, at least 25%, or at least 30%, in comparison with a control (e.g., untreated subject).

In at least the above embodiments, administration of ADAMTS13 in subjects with SCD or experiencing VOC administration of ADAMTS13 may be effective to change levels of Hct %, Hb, MCV, MCH, and/or HDW. Administration of ADAMTS13 may be effective to increase Hct % in subjects with SCD or experiencing VOC by at least 60%, at least 65%, at least 70%, at least 75%, at least 80%, or at least 85%, in comparison with a control (e.g., untreated subject). Administration of ADAMTS13 may be effective to increase Hb in subjects with SCD or experiencing VOC by at least 18%, at least 20%, at least 22%, at least 24%, or at least 26%, in comparison with a control (e.g., untreated subject). Administration of ADAMTS13 may be effective to increase MCV in subjects with SCD or experiencing VOC by at least 18%, at least 20%, at least 22%, at least 24%, or at least 26%, in comparison with a control (e.g., untreated subject). Administration of ADAMTS13 may be effective to increase MCH in subjects with SCD or experiencing VOC by at least 5%, at least 5.5%, at least 6%, at least 6.5%, or at least 7%, in comparison with a control (e.g., untreated subject). Administration of ADAMTS13 may be effective to decrease HDW in subjects with SCD or experiencing VOC by at least 12%, at least 14%, at least 16%, at least 18%, or at least 20%, in comparison with a control (e.g., untreated subject).

In at least the above embodiments, administration of ADAMTS13 in subjects with SCD experiencing VOC can reduce or prevent SCD related tissue injury. In certain embodiments, the tissue injury is cause by hypoxia. In certain embodiments, the tissue injury is caused by re-oxygenation. In certain embodiments, the tissue is lung tissue. In certain embodiments, the tissue is kidney tissue. In certain embodiments, administration of ADAMTS13 reduced inflammatory cell infiltrates and/or thrombi formation in the tissue as compared to control. In certain embodiments, administration of ADAMTS13 reduced inflammatory cell infiltrates in the lung tissue as compared to control. In certain embodiments, ADAMTS13 administration decreases the lung inflammatory cell infiltrates by at least 20%, at least 30%, at least 40%, at least 50%, or at least 60%. In certain embodiments, administration of ADAMTS13 reduced thrombi formation in the lung tissue as compared to control. In certain embodiments, ADAMTS13 administration decreases the lung thrombi formation by at least 20%, at least 30%, at least 40%, at least 50%, at least 60%%, at least 70%, at least 75%, at least 80%, or at least 85%. In certain embodiments, administration of ADAMTS13 reduced inflammatory cell infiltrates in the kidney tissue as compared to control. In certain embodiments, ADAMTS13 administration decreases the kidney inflammatory cell infiltrates by at least 20%, at least 30%, at least 40%, at least 50%, at least 60%, at least 70%, at least 75%, at least 80%, at least 85%, at least 90%, at least 95%, at least 97%, at least 98%, at least 99%, or at least 100%. In certain embodiments, administration of ADAMTS13 reduced thrombi formation in the lung tissue as compared to control. In certain embodiments, ADAMTS13 administration decreases the lung thrombi formation by at least 20%, at least 30%, at least 40%, at least 50%, or at least 60%.

In at least the above embodiments, administration of ADAMTS13 in subjects with ALI and/or ARDS can reduce or prevent ALR and/or ARDS related tissue injury. In certain embodiments, the tissue injury is cause by hypoxia. In certain embodiments, the tissue injury is caused by re-oxygenation. In certain embodiments, the tissue is lung tissue. In certain embodiments, the tissue is kidney tissue. In certain embodiments, administration of ADAMTS13 reduced inflammatory cell infiltrates and/or thrombi formation in the tissue as compared to control. In certain embodiments, administration of ADAMTS13 reduced inflammatory cell infiltrates in the lung tissue as compared to control. In certain embodiments, ADAMTS13 administration decreases the lung inflammatory cell infiltrates by at least 20%, at least 30%, at least 40%, at least 50%, or at least 60%. In certain embodiments, administration of ADAMTS13 reduced thrombi formation in the lung tissue as compared to control. In certain embodiments, ADAMTS13 administration decreases the lung thrombi formation by at least 20%, at least 30%, at least 40%, or at least 50%. In certain embodiments, administration of ADAMTS13 reduced inflammatory cell infiltrates in the kidney tissue as compared to control. In certain embodiments, ADAMTS13 administration decreases the kidney inflammatory cell infiltrates by at least 20%, at least 30%, at least 40%, at least 50%, or at least 60%. In certain embodiments, administration of ADAMTS13 reduced thrombi formation in the lung tissue as compared to control. In certain embodiments, ADAMTS13 administration decreases the lung thrombi formation by at least 20%, at least 30%, or at least 40%.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Additional aspects and details of the disclosure will be apparent from the following examples, which are intended to be illustrative rather than limiting.

Example 1

ADAMTS13 Prevented the Death of SCD Mice Exposed to Lethal Hypoxia-Induced VOC

Because acute sickle cell events are triggered by low oxygen (hypoxia), this example was conducted to evaluate the impact of ADAMTS13 on survival in a model of SCD subject to hypoxia. The objective of this example was to determine if recombinant ADAMTS13 (rADAMTS13 (BAX930/SHP655)) could protect humanized SCD mice exposed to lethal hypoxia-induced VOC. It has been shown previously that the exposition of SCD mice to very severe, life-threatening hypoxia/reoxygenation stress can be useful in evaluating the effectiveness of novel therapeutic treatments on the survival of SCD mice (Sabaa et al., JCI 118:1924, 2008).

Experiments were performed on 4-6 week-old healthy control (Hba$^{tm1(HBA)Tow}$ Hbb$^{tm3(HBG1,HBB)Tow}$) mice (i.e., AA) and SCD (Hba$^{tm1(HBA)Tow}$ Hbb$^{tm2(HBG1,HBB*)Tow}$) mice (humanized mouse model for sickle cell disease (i.e., SCD or SS mice)). Healthy (AA) and sickle cell disease mice (SCD or SS) were treated with either vehicle or rADAMTS13 at a dosage of 2,940 FRETS-U/kg (~3,200 IU/kg) intravenously (iv), 1 hour before severe hypoxia/re-oxygenation stress (at about 7% oxygen for 10 hours), followed by 3 hours of re-oxygenation with about 21% oxygen), which previously has been shown to biologically recapitulate the organ damage observed in acute VOC in human SCD patients. See similar protocol as reported by Kalish et al. (supra). More specifically, four groups (n=6) of AA and SCD mice were treated with either vehicle or ADAMTS13 (BAX930/SHP655) (2,940 FRETS-U/kg (~3,200 IU/kg)) and were exposed to conditions of hypoxic stress.

Recombinant ADAMTS13 treatment completely protected SCD mice from death as compared to SCD mice treated with vehicle (0% mortality in rADAMTS13 treated SCD vs. 83.3% mortality in vehicle-treated SCD mice at 10 hours hypoxia; 0% mortality in rADAMTS13-treated SCD vs. 100% mortality in vehicle-treated SCD mice at 10 hours hypoxia followed by 3 hours re-oxygenation; p<0.001) (FIG. 1). No differences in mouse survival were observed in healthy mice treated with either vehicle or rADAMTS13.

The data demonstrated that ADAMTS13 had a protective effect, including increased survival, in a model of SCD after exposure to hypoxic stress.

Example 2

ADAMTS13 Reduces Hypoxia/Reoxygenation Stress-Induced Abnormalities in the Lung

The objective of this example was to evaluate the impact of ADAMTS13 on lung injury and vascular inflammation induced by hypoxia/reoxygenation (H/R) stress.

Healthy control (Hba$^{tm1(HBA)Tow}$ Hbb$^{tm3(HBG1,HBB)Tow}$) and SCD (Hba$^{tm1(HBA)Tow}$ Hbb$^{tm2(HBG1,HBB*)Tow}$) mice were exposed to hypoxia/re-oxygenation (H/R) stress, which previously were shown to biologically recapitulate the acute VOC and the organ damage observed in acute VOC in human SCD patients. In particular, six experimental groups were used—(1) AA untreated normoxia; (2) SS untreated normoxia; (3) AA vehicle plus H/R; (4) AA ADAMTS13 (BAX930/SHP655) plus H/R; (5) SS vehicle plus H/R; and (6) SS ADAMTS13 (BAX930/SHP655) plus H/R. In this experiment, H/R conditions were 8% oxygen for 10 h followed by 3 h recovery at about 21% oxygen, an experimental scheme usually not fatal for SCD mice (Kalish et al., *Haematologica* 100:870-80, 2015).

Under both normoxic and H/R conditions, pulmonary vascular leakage was evaluated in mice by measuring protein content and leukocyte counts (total leukocytes measured in cells/microliter) in bronchoalveolar lavage fluid (BAL).

Pulmonary vascular leakage was examined by measuring protein content and leukocyte counts (i.e., cell number) in bronchoalveolar lavage fluid (BAL). As shown in Table 1, under normoxic conditions, increased BAL protein level and leukocyte cell numbers were detected in SCD mice compared to healthy mice, indicating the accumulation of proteins and inflammatory cells in the alveolar space. Interestingly, in response to H/R, both BAL protein and leukocyte counts were significantly increased in both SCD and AA mice.

TABLE 1

Results of pulmonary leakage experiments carried out in AA and SCD mice under both normoxic and hypoxic conditions.

| | Normoxic conditions | | Hypoxic condition (8% oxygen) | | | |
|---|---|---|---|---|---|---|
| | AA mice untreated (n = 6) | SCD mice untreated (n = 6) | AA mice Vehicle (n = 6) | AA mice BAX930 (n = 6) | SCD mice Vehicle (n = 6) | SCD mice BAX930 (n = 6) |
| BAL protein content (mg/mL) | 0.9 ± 0.03 | 2.5 ± 0.05° | 3.1 ± 0.04 | 1.8 ± 0.05* | 5.33 ± 0.4° | 3.4 ± 0.07* |
| BAL leukocytes (cells/µL) | 200 ± 40 | 832 ± 36° | 567 ± 20 | 328 ± 12* | 1977 ± 54° | 1198 ± 22* |

AA: Hb A homozygous control mice or healthy mice; SCD: HbS homozygous mice or sickle cell mice; and BAL: Bronchoalveolar lavage;
*P < 0.05 compared to vehicle-treated mice;
°P < 0.05 compared to AA mice.

Figure 2A:
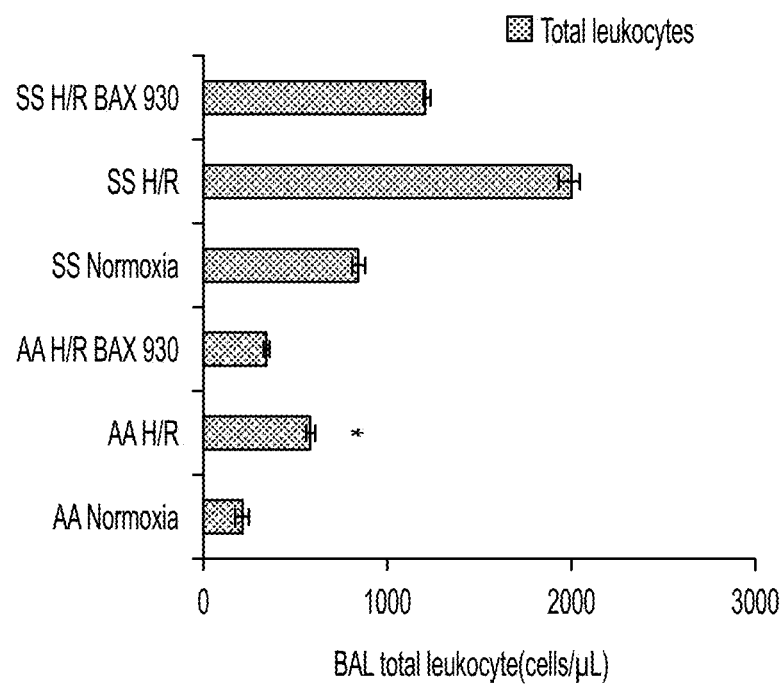
FIG. 2A-2C.
Figure 2A:
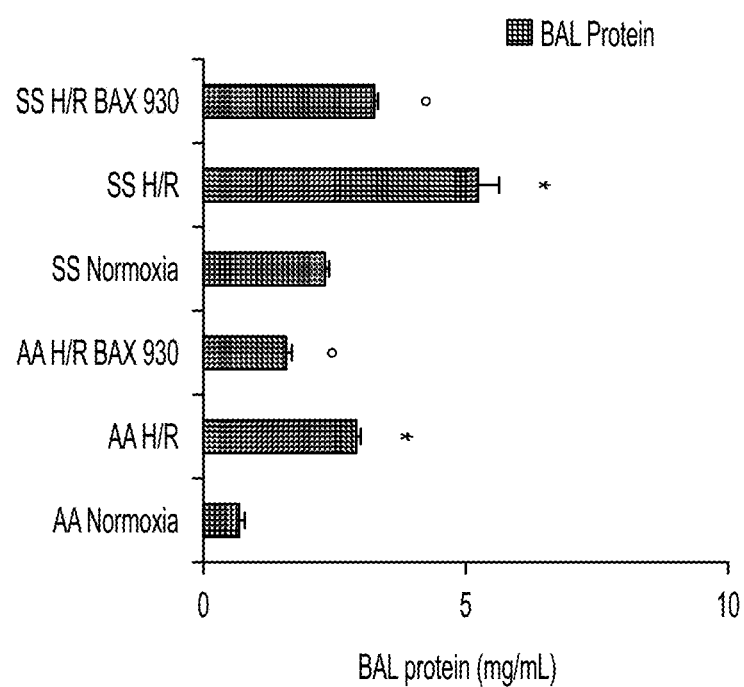

The data showed that SCD mice had a significant increase in peripheral neutrophils (cells/microliter) compared to AA mice; however, treatment with ADAMTS13 significantly reduced the neutrophil count. The data also showed that SCD mice had a greater number of leukocytes (bronchoalveolar lavage (BAL) total leukocytes (cells/microliter)) and greater leukocyte protein content (BAL protein (mg/mL) in bronchoalveolar lavage) compared to controls, indicating that the SCD mice suffered vascular leakage. Treatment with ADAMTS13 markedly reduced this effect (FIG. 2A and Table 1), indicating that ADAMTS13 reduced systemic inflammation and reduced abnormalities in pulmonary vascular dysfunction.

These data indicate that ADAMTS13 prevented the hypoxia-induced inflammatory vasculopathy and abnormalities of pulmonary vascular leakage in lungs from SCD mice during acute vaso-occlusive crisis. Moreover, ADAMTS13 significantly decreased both BAL protein content and leukocyte cell number in both SCD and AA mice compared to vehicle-treated controls, indicating that ADAMTS13 had a protective effect on the lung under hypoxic conditions.

Example 3

ADAMTS13 Reduced Hypoxia/Reoxygenation Stress-Induced Lung Vascular Activation

In order to study the effects of ADAMTS13 on injury and vascular inflammation in the lung, additional experiments were conducted with the same six experimental groups, as described in Example 2 (i.e., (1) AA untreated normoxia; (2) SS untreated normoxia; (3) AA vehicle plus H/R; (4) AA ADAMTS13 (BAX930/SHP655) plus H/R; (5) SS vehicle plus H/R; and (6) SS ADAMTS13 (BAX930/SHP655) plus H/R). In this example, like that reported in Example 2, animals were administered vehicle or ADAMTS13 and then exposed to 8% oxygen for 10 h followed by 3 h recovery at 21% oxygen. Additional controls (AA and SCD) were also subjected to conditions of normoxia without vehicle or ADAMTS13.

Immunoblot analyses with specific antibodies against various markers of inflammation, vaso-constriction and platelet aggregation (i.e., nuclear factor kappa B (NF-kB), endothelin-1 (ET-1), heme-oxygenase 1 (HO-1), intercellular adhesion molecule 1 (ICAM-1), thromboxane synthase (TXAS), and vascular cell adhesion molecule 1 (VCAM-1)) were carried out to measure the expression of these proteins in the lungs of healthy control (AA) and SCD mice treated with either vehicle or rADAMTS13 after exposure to hypoxic (e.g., H/R) or normoxic conditions.

Figure 2B:
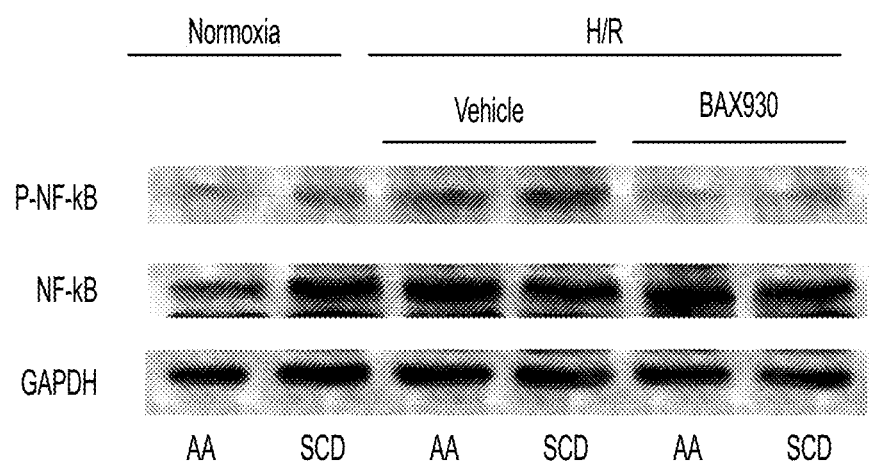
Figure 2C:
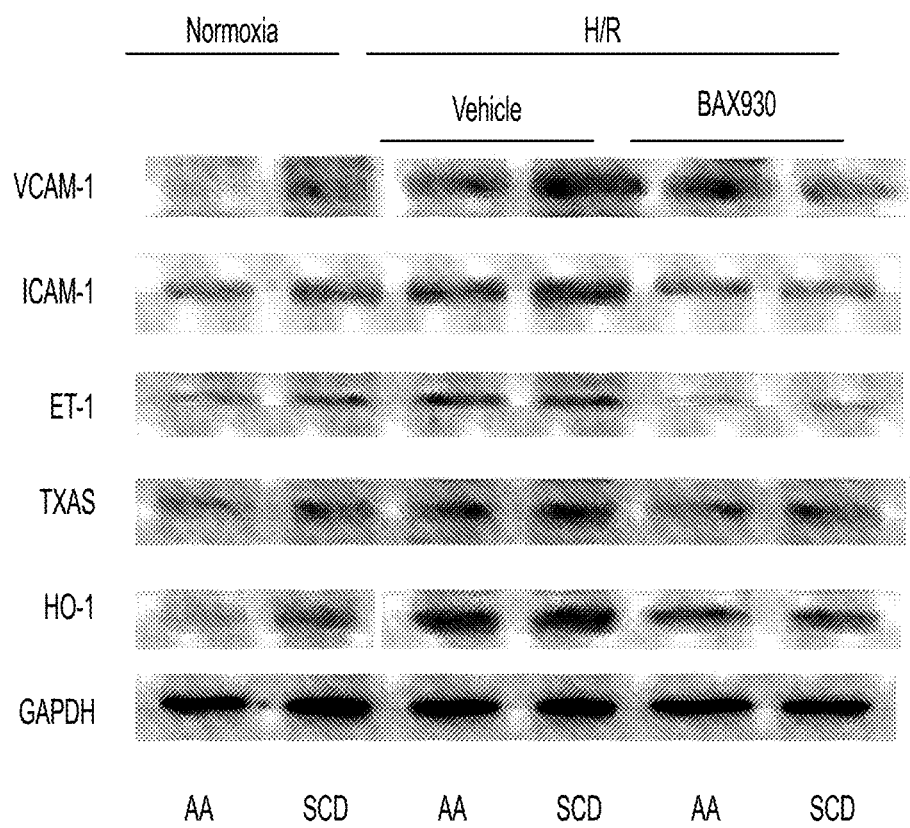

The data from this example showed that ADAMTS13 prevented the hypoxia-induced activation of NF-kB in lung tissues from AA and SCD mice, indicating that ADAMTS13 decreases the pulmonary inflammation process triggered by hypoxia (FIG. 2B). In lungs from SCD mice under hypoxia, ADAMTS13 prevented activation of VCAM-1 and ICAM-1, markers of vascular activation and inflammatory vasculopathy, and reduced the expression of endothelin-1 (ET-1), thromboxane synthase (TXAS), and heme-oxygenase-1 (HO-1) (FIG. 2C).

Table 2 reports the densitometric values obtained through immunoblot analyses with specific antibodies against nuclear factor kappa B (NF-kB) and its activated form (P-NF-kB), endothelin 1 (ET-1), heme-oxygenase 1 (HO-1), intercellular adhesion molecule 1 (ICAM-1), thromboxane synthase (TXAS), and vascular cell adhesion molecule 1 (VCAM-1) in the lungs from healthy control (AA) and sickle cell (SCD) mice treated with either vehicle or rADAMTS13 and exposed to normoxic or hypoxia/reoxygenation stress.

As set out in Table 2, under normoxic conditions, all of the measured protein markers (except for ICAM-1) showed increased protein expression in SCD mice compared to AA mice. Under hypoxic conditions, there was further increased expression of all the measured markers in both healthy controls and SCD mice. However, treatment with ADAMTS13 (i.e., BAX930/SHP655) had a protective effect in both AA and SCD mice, as demonstrated by lower levels of all markers of inflammation, vaso-constriction and platelet aggregation tested.

TABLE 2

|  | Normoxic conditions | | Hypoxic condition (8% oxygen) | | | |
| --- | --- | --- | --- | --- | --- | --- |
|  | AA mice untreated (n = 6) | SCD mice untreated (n = 6) | AA mice Vehicle (n = 6) | AA mice BAX930 (n = 6) | SCD mice Vehicle (n = 6) | SCD mice BAX930 (n = 6) |
| TXAS (DU) | 0.9 ± 0.09 | 2 ± 0.025° | 2.4 ± 0.05 | 0.7 ± 0.04* | 3.7 ± 0.05° | 0.8 ± 0.034* |
| ET-1 (DU) | 0.55 ± 0.06 | 1.65 ± 0.07° | 1.7 ± 0.025 | 0.4 ± 0.042* | 2 ± 0.06° | 0.6 ± 0.03* |
| VCAM-1 (DU) | 0.5 ± 0.03 | 1.4 ± 0.07° | 2.1 ± 0.04 | 2.0 ± 0.02 | 3.2 ± 0.09° | 1.8 ± 0.03* |
| ICAM-1 (DU) | 0.8 ± 0.03 | 0.9 ± 0.07 | 1.7 ± 0.045 | 0.75 ± 0.04* | 2.3 ± 0.081° | 0.85 ± 0.07* |
| HO-1 (DU) | 0.4 ± 0.06 | 1.1 ± 0.03° | 2.8 ± 0.02 | 1.5 ± 0.07* | 3.0 ± 0.04 | 1.44 ± 0.09* |
| P-NF-kB/ NF-kB ratio (DU) | 0.8 ± 0.03 | 1.6 ± 0.08° | 2 ± 0.6 | 0.7 ± 0.05* | 3.8 ± 0.34° | 0.6 ± 0.03* |

AA: HbA homozygous control mice or healthy mice; SCD: HbS homozygous mice or sickle cell mice; TXAS: Thromboxane synthase; ET-1: Endothelin 1; VCAM-1: Vascular Cell Adhesion Molecule 1; ICAM-1: Intercellular Adhesion Molecule 1; HO-1: Hemeoxygenase 1; P-NF-kB: Phospho-Nuclear Factor kappa B; and NF-kB: Nuclear Factor kappa B.
*$P < 0.05$ compared to vehicle-treated mice;
°$P < 0.05$ compared to AA mice.

Recombinant ADAMTS13 markedly reduced the expression levels of each of the protein markers tested in SCD mice (i.e., compared to vehicle-treated SCD mice) (Table 2). Furthermore, recombinant ADAMTS13 reduced lung expression of all the protein markers tested, with the exception of VCAM-1, in healthy control (AA) mice (i.e., compared to vehicle-treated control mice).

These data indicate that ADAMTS13 prevented the hypoxia-induced inflammatory vasculopathy and abnormalities of pulmonary vascular leakage in lungs from SCD mice during acute vaso-occlusive crisis. In addition, ADAMTS13 prevented the hypoxia induced increased expression of potent modulators of vascular tone, such as ET-1 and TXAS, both indicated as factors contributing to vascular dysfunction described in SCD during acute events. Moreover, the data also showed that ADAMTS13 had a protective effect on lung tissue in healthy animals subject to hypoxic conditions. Thus, the data indicate that ADAMTS13 reduces vascular activation and inflammatory responses related to hypoxic stress in the lungs of SCD and healthy mice.

Example 4

ADAMTS13 Reduces Hypoxia/Reoxygenation Stress-Induced Kidney Vascular Activation In order to study the effects of ADAMTS13 on injury and vascular inflammation in the kidney, additional experiments were conducted with the same six experimental groups, as described in Example 2 (i.e., (1) AA untreated normoxia; (2) SS untreated normoxia; (3) AA vehicle plus H/R; (4) AA ADAMTS13 (BAX930/SHP655) plus H/R; (5) SS vehicle plus H/R; and (6) SS ADAMTS13 (BAX930/SHP655) plus H/R). In this example, like those reported in Examples 2 and 3, animals were administered vehicle or ADAMTS13 and then exposed to 8% oxygen for 10 h followed by 3 h recovery at about 21% oxygen, which was previously shown to biologically recapitulate the acute VOC and the organ damage observed in acute VOC in human SCD patients. Additional controls (AA and SCD) were also subjected to conditions of normoxia without vehicle or ADAMTS13.

Immunoblot analyses with specific antibodies against NF-kB and its activated form, P-NF-kB, as well as ET-1, TXAS, and VCAM-1 were carried out to measure the expression of these proteins in the kidneys from AA and SCD mice treated with either vehicle or rADAMTS13.

Table 3 reports the densitometric values obtained through immunoblot analyses with specific antibodies against nuclear actor kappa B (NF-kB) and its activated form (P-NF-kB), endothelin 1 (ET-1), thromboxane synthase (TXAS), and vascular cell adhesion molecule 1 (VCAM-1) in the kidneys from healthy control (AA) and sickle cell (SCD) mice treated with either vehicle or rADAMTS13 and exposed to normoxic or hypoxic (hypoxia/reoxygenation stress) conditions. As can be observed in Table 3, under normoxic conditions, all protein marker levels were greater in SCD mice than in AA mice. Under hypoxic conditions, the expression levels of all protein markers, except VCAM-1, were further increased in both SCD and AA mice.

TABLE 3

|  | Normoxic conditions | | Hypoxic condition (8% oxygen) | | | |
| --- | --- | --- | --- | --- | --- | --- |
|  | AA mice untreated (n = 6) | SCD mice untreated (n = 6) | AA mice Vehicle (n = 6) | AA mice BAX930 (n = 6) | SCD mice Vehicle (n = 6) | SCD mice BAX930 (n = 6) |
| TXAS (DU) | 0.6 ± 0.05 | 0.97 ± 0.03° | 1.8 ± 0.07 | 0.4 ± 0.022* | 2.5 ± 0.041° | 0.6 ± 0.02* |
| ET-1 (DU) | 0.5 ± 0.051 | 0.98 ± 0.05° | 1.1 ± 0.012 | 0.99 ± 0.02 | 1.5 ± 0.03° | 1.4 ± 0.02 |
| VCAM-1 (DU) | 1.1 ± 0.02 | 1.9 ± 0.06° | 1.05 ± 0.08 | 0.9 ± 0.05 | 2.1 ± 0.08° | 0.8 ± 0.03* |

TABLE 3-continued

|  | Normoxic conditions | | Hypoxic condition (8% oxygen) | | | |
| --- | --- | --- | --- | --- | --- | --- |
|  | AA mice untreated (n = 6) | SCD mice untreated (n = 6) | AA mice Vehicle (n = 6) | AA mice BAX930 (n = 6) | SCD mice Vehicle (n = 6) | SCD mice BAX930 (n = 6) |
| P-NF-kB/ NF-kB ratio (DU) | 0.4 ± 0.02 | 1.5 ± 0.045° | 2.4 ± 0.08 | 0.6 ± 0.055* | 2.3 ± 0.023 | 0.7 ± 0.08* |

AA: Hb A homozygous control mice or healthy mice; SCD: HbS homozygous mice or sickle cell mice; TXAS: Thromboxane synthase; ET-1: Endothelin 1; VCAM-1: Vascular Cell Adhesion Molecule 1; P-NF-kB: Phospho-Nuclear Factor kappa B; and NF-kB: Nuclear Factor kappa B.
*$P < 0.05$ compared to vehicle-treated mice;
°$P < 0.05$ compared to AA mice.

Figure 3A:
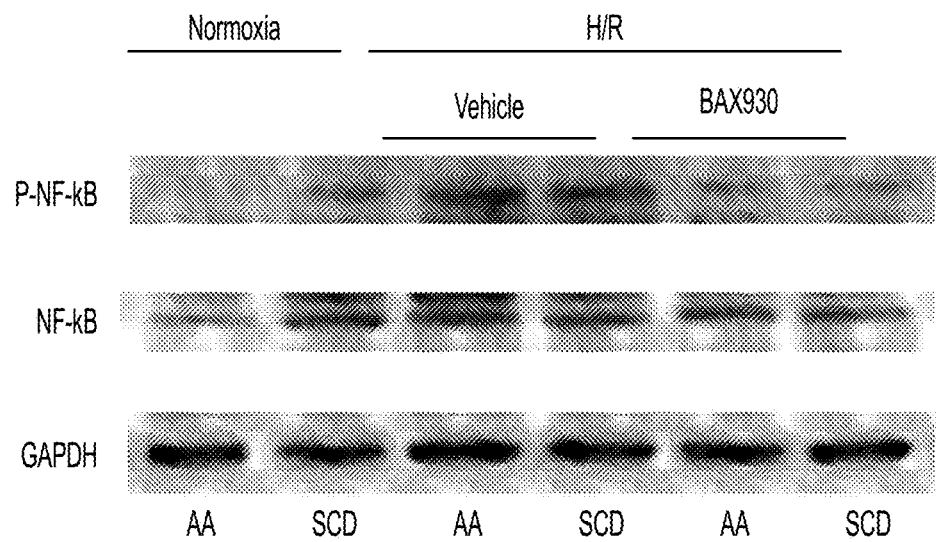
FIG. 3A-B.
Figure 3B:
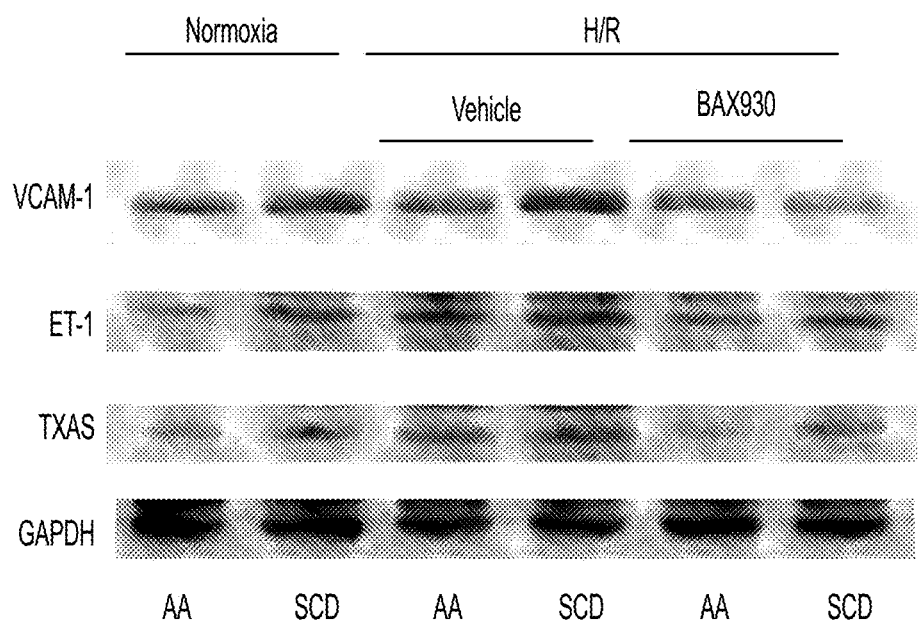

The data from this example showed that ADAMTS13 prevented the hypoxia-induced activation of NF-kB in the kidneys from AA and SCD mice, as well as of SCD mice under normoxic conditions (Table 3 and FIG. 3A). In hypoxia-exposed SCD mice, there was increased expression of VCAM-1, ET-1, and TXAS. ADAMTS13 prevented the hypoxia-induced increased expression of VCAM-1 and TXAS in kidneys of both mouse strains and of ET-1 levels in kidneys from AA mice (Table 3 and FIG. 3B).

These data indicate that ADAMTS13 prevented the hypoxia-induced increased expression of potent modulators of vascular tone, and/or factors contributing to vascular dysfunction described in SCD during acute events. The data indicate that ADAMTS13 reduces vascular activation and inflammatory responses related to hypoxic stress in the kidneys of SCD and healthy mice. The example showed that rADAMTS13 could reduce acute sickle cell related events, like vaso-constriction and inflammatory vasculopathy in the kidney.

Example 5

ADAMTS13 Ameliorates Hypoxia/Reoxygenation Stress-Induced Abnormalities in Various Hematology Parameters In order to study the effects of ADAMTS13 on various hematology parameters, additional experiments were conducted with the same six experimental groups, as described in Example 2 (i.e., (1) AA untreated normoxia; (2) SS untreated normoxia; (3) AA vehicle plus H/R; (4) AA ADAMTS13 (BAX930/SHP655) plus H/R; (5) SS vehicle plus H/R; and (6) SS ADAMTS13 (BAX930/SHP655) plus H/R). In this example, like those reported in Examples 2-4, animals were administered vehicle or ADAMTS13 and then exposed to conditions of normoxia or H/R (8% oxygen for 10 h followed by 3 h recovery at about 21% oxygen).

The following hematology parameters were determined: % hematocrit (Hct) and mean corpuscular volume (MCV), as indicators of erythrocyte viability; hemoglobin (Hb), mean corpuscular hemoglobin (MCH), and cell hemoglobin concentration mean (CHCM), as indicators of oxygen binding capacity; heterogeneity of red cell distribution (HDW), as an indicator of presence of dense red cells; reticulocyte count, as an indicator of anemia status; neutrophil count, as an indicator of the systemic inflammatory status; and lactate dehydrogenase (LDH) as a general marker of cell damage.

Hematocrit is the ratio of the volume of red blood cells to the total volume of blood. MCV is the average volume of RBCs. Hemoglobin is the protein responsible for transporting oxygen in the blood, and MCH is the average amount of hemoglobin per RBC in a blood sample; CHCM reflects the hemoglobin content within intact RBCs. Hemoglobin distribution width (HDW) is a measurement of the heterogeneity of the red cell hemoglobin concentration. Reticulocytes are newly produced, relatively immature red blood cells; reticulocyte count indicates whether enough red blood cells are being produced in the bone marrow. Neutrophils are recruited to the site of injury within minutes following a trauma; thus, neutrophils are the hallmark of acute inflammation and neutrophil count indicates inflammatory status.

Table 4 shows the hematological parameters in healthy control (AA) and sickle cell (SCD) mice in normoxic conditions and after treatment with ADAMTS13 (i.e., BAX930/SHP655) or vehicle and exposure to hypoxia/reoxygenation stress. As shown in Table 4, under normoxic conditions, Hct and Hb levels were lower, while MCV and HDW levels were higher, as were reticulocyte number and neutrophil number, in SCD mice compared to control (AA) mice. In healthy control mice, hypoxic conditions increased the number of reticulocytes and neutrophils. The administration of ADAMTS13 to control mice ameliorated the large increase in neutrophil number, indicating a reduction in inflammation. In SCD mice, hypoxic conditions reduced Hct, Hb, MCV and MCH, and increased CHCM, HDW, and neutrophil number. The administration of ADAMTS13 to SCD mice ameliorated the decrease in Hct, Hb, MCV, and MCH, and ameliorated the increase in CHCM, HDW, and neutrophil number.

TABLE 4

|  | Normoxic conditions | | Hypoxic condition (8% oxygen) | | | |
| --- | --- | --- | --- | --- | --- | --- |
|  | AA mice untreated (n = 6) | SCD mice untreated (n = 6) | AA mice Vehicle (n = 6) | AA mice BAX930 (n = 5) | SCD mice Vehicle (n = 6) | SCD mice BAX930 (n = 5) |
| Hct (%) | 46.3 ± 0.95 | 35.6 ± 1.6° | 45.3 ± 0.8 | 44.3 ± 0.4 | 15.8 ± 2.3° | 27.9 ± 0.8* |
| Hb (g/dL) | 13.8 ± 1.3 | 8.7 ± 0.51° | 13.4 ± 0.1 | 13.1 ± 0.5 | 5.99 ± 0.5° | 7.4 ± 0.5* |

TABLE 4-continued

|  | Normoxic conditions | | Hypoxic condition (8% oxygen) | | | |
| --- | --- | --- | --- | --- | --- | --- |
|  | AA mice untreated (n = 6) | SCD mice untreated (n = 6) | AA mice Vehicle (n = 6) | AA mice BAX930 (n = 5) | SCD mice Vehicle (n = 6) | SCD mice BAX930 (n = 5) |
| MCV (fL) | 37.9 ± 0.2 | 50.9 ± 1.8° | 38.3 ± 0.3 | 38.5 ± 0.3 | 41.3 ± 1.7° | 51.2 ± 1.8* |
| MCH (g/dL) | 12.0 ± 0.5 | 11.8 ± 1.2 | 12.0 ± 0.4 | 11.2 ± 0.2 | 9.1 ± 0.2° | 9.7 ± 0.4 |
| CHCM (g/dL) | 25.2 ± 0.1 | 25.1 ± 0.4 | 25.1 ± 0.6 | 23.3 ± 0.9 | 26.8 ± 0.3° | 24.8 ± 0.2* |
| HDW (g/dL) | 2.88. ± 0.03 | 4.72 ± 0.08° | 2.86 ± 0.03 | 2.9 ± 0.04 | 5.63 ± 0.06° | 4.78 ± 0.04* |
| Retics (%) | 7.22 ± 0.5 | 43.1 ± 11° | 8.59 ± 0.7 | 9.6 ± 0.21 | 42.1 ± 12° | 45 ± 2.9 |
| Neutrophils (cells/μL) | 841 ± 135 | 3251 ± 488° | 3600 ± 120 | 1768 ± 299* | 6800 ± 250° | 4399 ± 133* |
| LDH (U/L) | 288 ± 12 | 573 ± 30° | 293 ± 15 | 277 ± 26 | 1234 ± 81° | 852 ± 19* |

AA: Hb A homozygous control mice or healthy mice; SCD: HbS homozygous mice or sickle cell mice; Hct: hematocrit; Hb: hemoglobin; MCV: mean corpuscular volume; MCH: mean corpuscular hemoglobin; CHCM: cell hemoglobin concentration; HDW: heterogeneity of red cell distribution; Retics: reticulocytes; and LDH: lactate dehydrogenase.
*P < 0.002 compared to vehicle-treated mice;
°P < 0.005 compared to AA mice.

Example 6

ADAMTS13 Ameliorates Hypoxia/Reoxygenation Stress-Induced Abnormalities in Various Histopathology Parameters In order to study the effects of ADAMTS13 on various histopathology parameters, additional experiments were conducted with four experimental groups—(1) AA vehicle plus H/R; (2) AA ADAMTS13 (BAX930/SHP655) plus H/R; (3) SS vehicle plus H/R; and (4) SS ADAMTS13 (BAX930/SHP655) plus H/R. In this example, animals were administered vehicle or ADAMTS13 and then exposed to conditions of H/R (8% oxygen for 10 h followed by 3 h recovery at about 21% oxygen).

Lungs and kidneys were collected following the 3 h re-oxygenation. The lung and kidney pathology was analyzed and the inflammatory cell infiltrate and presence of thrombi were determined.

The histologic analysis revealed that H/R stress induced a severe SCD related tissue injury in both lung and kidney of SCD mice. In the lung, H/R induced inflammatory cell infiltration and thrombi formation in all SCD mice (Table 5). In AA mice, H/R induced modest inflammatory cell infiltration and some thrombi formation in few mice. In SCD mice, ADAMTS13 (BAX930/SHP655) reduced inflammatory cell infiltrate and thrombi formation compared to vehicle treated SCD mice. In AA mice, ADAMTS13 (BAX930/SHP655) reduced the cell inflammatory infiltrate in the lung.

In the kidney, H/R induced inflammatory cell infiltration and thrombi in all SCD mice. In AA mice, H/R induced limited inflammatory cell infiltration with few thrombi formation in a small number of mice. ADAMTS13 (BAX930/SHP655) reduced inflammatory cell infiltrates in kidney from H/R exposed SCD mice, impacting also the thrombi formation. In AA mice, ADAMTS13 (BAX930/SHP655) reduced cell inflammatory infiltrates with no effects on thrombi formation (Table 5).

TABLE 5

|  | AA mice | | SCD mice | |
| --- | --- | --- | --- | --- |
|  | H/R vehicle | H/R BAX930 | H/R vehicle | H/R BAX930 |
| Lung | (n = 5) | (n = 5) | (n = 5) | (n = 4) |
| Inflammatory cell infiltrates | +(4/5) | +(2/5) | +(2/5) ++(3/5) | +(1/4) |
| Thrombi | +(2/5) 2.5 per field of observation | +(5/5) 2.2 field of observation | +(5/5) 3 per field of observation | +(1/4) 3 per field of observation |
| Kidney | (n = 5) | (n = 5) | (n = 5) | (n = 4) |
| Inflammatory cell infiltrates | +(2/5) | +(1/5) | +(2/5) ++(1/5) | 0 |
| Thrombi | +(4/5) 3.8 per field of observation | +(5/5) 3.2 per field of observation | +(5/5) 5 per field of observation | +(4/4) 2.5 per field of observation |

H/R: hypoxia/re-oxygenation stress; presence of thrombi per field of 250× magnification given in numbers; presence of inflammatory cell infiltrates per field of magnification (250× for lung tissue, 400× for kidneys): + 1-10 cells per field of magnification; ++ 10-50 cells per field of magnification; number of animals with findings stated in parentheses Example 7

ADAMTS13 Reduces Organ Damage in Subjects Suffering from Hypoxemia and in Subjects at Risk of Developing ARDS ADAMTS13 has been demonstrated to reduce end organ injury in a mouse model of severe hypoxemia (8% oxygen for 10 h followed by 3 h recovery at about 21% oxygen). Because severe hypoxemia injury is a contributing factor to the pathophysiology observed in patients suffering from acute lung injury (ALI) and acute respiratory distress syndrome (ARDS) (ALI/ARDS), it was hypothesized that the administration of ADAMTS13 to patients either at risk for or who have developed ALI and/or ARDS (ALI/ARDS) could prevent, treat or ameliorate the disease process and result in improved outcomes such as survival, long term lung function, and avoidance of other end organ injury.

Mice are administered LPS, either directly to the lungs through intratracheal injection or inhalation, or intraperitoneally or intravenously to incite a systemic inflammatory response. Mice treated with intratracheal LPS have an acute and robust inflammatory cell influx to the lung with resolution by 48 hours. Intraperitoneal LPS activates systemic inflammation and is associated with a mild lung injury. This injury can be augmented with either repeated injections of LPS or the implantation of an LPS pump in the peritoneal cavity to continually release LPS for hours, or even days.

ADAMTS13 is administered in doses of about 50, 100, 200, 500, 1,000, 2,000, and 3,000 international units per kilogram body weight prior to treatment with LPS and within 12, 24, 48, 72, and 96 hours after treatment with LPS. Doses of ADAMTS13 are administered daily or every 12 hours subcutaneously or intravenously until subjects are sacrificed to examine inflammatory response in the lung and organ damage.

ADAMTS13 treatment reduces the inflammatory response, including inflammatory cell influx to the lungs, as measured by the reduced number of neutrophils, macrophages, monocytes, mast cells, eosinophils, and/or basophils, present in the lungs of mice treated with ADAMTS13. ADAMTS13 treatment also reduces organ damage, as measured by blood urea nitrogen (BUN), creatinine, BUN/creatinine ratio, troponin, neuron-specific enolase (NSE).

The invention has been described in terms of particular embodiments found or proposed to comprise specific modes for the practice of the invention. Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A method for treating or preventing a vaso-occlusive crisis in a subject suffering from sickle cell disease (SCD), the method comprising administering to the SCD subject in need thereof a therapeutically effective amount of a composition comprising A Disintegrin And Metalloproteinase with Thrombospondin type 1 motif, member-13 (ADAMTS13).

2. The method of claim 1, wherein the SCD subject is administered the composition comprising ADAMTS13 after symptoms of a vaso-occlusive crisis are present.

3. The method of claim 1, wherein the SCD subject is administered the composition comprising ADAMTS13 before symptoms of a vaso-occlusive crisis are present.

4. The method of claim 1, wherein administering the composition comprising ADAMTS13 to the SCD subject reduces at least one of inflammation, vasoconstriction, platelet aggregation, or a combination of any thereof as compared to a control subject or to observation of the SCD subject without the administration of said ADAMTS13 composition.

5. The method of claim 1, wherein administering the composition comprising ADAMTS13 to the SCD subject results in at least one of improved survival, improved lung function, reduced organ damage, reduced pulmonary vascular leakage, or a combination of any thereof as compared to a control subject or to observation of the SCD subject without the administration of said ADAMTS13 composition.

6. The method of claim 1, wherein administering the composition comprising ADAMTS13 to the SCD subject reduces and/or prevents at least one of impaired blood flow, blood coagulation, vascular inflammation, thrombosis, ischemic cell damage, or organ damage, or a combination of any thereof as compared to a control subject or to observation of the SCD subject without the administration of said ADAMTS13 composition.

7. The method of claim 1, wherein administering the ADAMTS13 composition to the SCD subject reduces and/or prevents pain or severity of the pain as compared to a control subject or to observation of the SCD subject without the administration of said ADAMTS13 composition.

8. The method of claim 1, wherein administering the ADAMTS13 composition to the SCD subject reduces the frequency of occurrence and/or duration of vaso-occlusive crisis (VOC) episodes as compared to a control subject or to observation of the SCD subject without the administration of said ADAMTS13 composition.

9. The method of claim 1, wherein administering the ADAMTS13 composition to the SCD subject reduces expression, level, and/or activation of at least one of Vascular Cell Adhesion Molecule-1 (VCAM-1), Intercellular Adhesion Molecule 1 (ICAM-1), Phospho-Nuclear Factor-kappa B (P-NF-kB), Nuclear Factor-kappa B (NF-kB), Endothelin 1 (ET-1), Thromboxane synthase (TXAS), and Heme-oxygenase-1 (HO-1) in an organ of the SCD subject as compared to a control subject or to observation of the SCD subject without the administration of said ADAMTS13 composition.

10. The method of claim 1, wherein administering the ADAMTS13 composition to the SCD subject increases the level of at least one of Hematocrit (Hct), Hemoglobin (Hb), mean corpuscular volume (MCV), and mean corpuscular hemoglobin (MCH) in the blood as compared to a control subject or to observation of the SCD subject without the administration of said ADAMTS13 composition.

11. The method of claim 1, wherein administering the ADAMTS13 composition to the SCD subject reduces the level of at least one of cell hemoglobin concentration mean (CHCM), heterogeneity of red cell distribution (HDW), lactate dehydrogenase (LDH), and neutrophil numbers in the blood as compared to a control subject or to observation of the SCD subject without the administration of said ADAMTS13 composition.

12. The method of claim 1, wherein the therapeutically effective amount of ADAMTS13 is from about 20 to about 6,000 international units per kilogram body weight, about 40 to about 4,000 international units per kilogram body weight, about 50 to about 3,000 international units per kilogram body weight, or 50 to about 500 international units per kilogram body weight.

13. The method of claim 1, wherein the composition comprising ADAMTS13 is administered in a single bolus injection, monthly, every two weeks, weekly, twice a week, daily, every 12 hours, every eight hours, every six hours, every four hours, or every two hours.

14. The method of claim 1, wherein the composition comprising ADAMTS13 is administered intravenously or subcutaneously.

15. The method of claim 1, wherein the ADAMTS13 is recombinant ADAMTS13.

16. The method of claim 1, wherein the ADAMTS13 is plasma derived.

17. The method of claim 1, wherein the subject is a mammal.

18. The method of claim 1, wherein the subject is a human.

19. The method of claim 1, wherein the composition is in a stable aqueous solution ready for administration.

20. The method of claim 1, wherein the therapeutically effective amount of the composition comprising ADAMTS13 is administered to the subject within 48 hours after the onset of the vaso-occlusive crisis.

21. The method of claim 15, wherein (a) the therapeutic amount is from about 10 to about 500 international units (IU) of ADAMTS13 activity per kilogram of the subject's body weight, and (b) the composition comprises a stable aqueous solution that is administered in a single bolus injection, monthly, every two weeks, weekly, twice a week, daily, or every 12 hours.

22. The method of claim 21, wherein the therapeutic amount of ADAMTS13 is from about 35 to about 320 international units per kilogram.

23. The method of claim 15, wherein (a) the therapeutic amount of ADAMTS13 is from about 10 to about 500 international units per kilogram and (b) the composition comprises a stable aqueous solution that is administered in a single bolus injection, daily, every 12 hours, every eight hours, every six hours, every four hours, or every two hours.

24. The method of claim 23, wherein the therapeutic amount of ADAMTS13 is from about 35 to about 320 international units per kilogram.

25. The method of claim 23, wherein the composition is administered within 48 hours, 24 hours, 12 hours, or 6 hours of the onset of the vaso-occlusive crisis (VOC).

26. The method of claim 21, wherein administering the ADAMTS13 composition to the SCD subject reduces the duration or frequency of occurrence of vaso-occlusive crisis (VOC) compared to a control subject.

27. The method of claim 25, wherein administering the ADAMTS13 composition to the SCD subject reduces the severity of a vaso-occlusive crisis (VOC) compared to a control subject.

28. The method of claim 26, wherein the composition provides the subject with a protective effect against a vaso-occlusive crisis (VOC) comprising an improved lower level of each of a plurality of markers of inflammation, vasoconstriction, or platelet aggregation, wherein said markers are selected from Thromboxane synthase (TXAS), Endothelin 1 (ET-1), Vascular Cell Adhesion Molecule-1 (VCAM-1), Intercellular Adhesion Molecule 1 (ICAM-1), Heme-oxygenase-1 (HO-1), and the ratio of Phospho-Nuclear Factor-kappa B (P-NF-kB) to Nuclear Factor-kappa B (NF-kB).

29. The method of claim 27, wherein the composition provides the subject with a protective effect against a vaso-occlusive crisis (VOC) comprising an improved lower level of each of a plurality of markers of inflammation, vasoconstriction, or platelet aggregation, wherein said markers are selected from Thromboxane synthase (TXAS), Endothelin 1 (ET-1), Vascular Cell Adhesion Molecule-1 (VCAM-1), Intercellular Adhesion Molecule 1 (ICAM-1), Heme-oxygenase-1 (HO-1), and the ratio of Phospho-Nuclear Factor-kappa B (P-NF-kB) to Nuclear Factor-kappa B (NF-kB).

30. The method of claim 28, wherein the composition provides a lower level of all of said markers.

31. The method of claim 29, wherein the composition provides a lower level of all of said markers.

32. The method of claim 26, wherein the composition provides the subject with improved hematology parameters comprising a lower level of each of a plurality of said parameters selected from cell hemoglobin concentration mean (CHCM), heterogeneity of red cell distribution (HDW), lactate dehydrogenase (LDH), and neutrophil numbers.

33. The method of claim 27, wherein the composition provides the subject with improved hematology parameters comprising a lower level of each of a plurality of said parameters selected from cell hemoglobin concentration mean (CHCM), heterogeneity of red cell distribution (HDW), lactate dehydrogenase (LDH), and neutrophil numbers.

34. The method of claim 28, wherein the composition provides a lower level of all of said hematology parameters.

35. The method of claim 29, wherein the composition provides a lower level of all of said hematology parameters.

36. The method of claim 26, wherein the composition provides the subject with improved hematology parameters comprising a higher level of each of a plurality of said parameters selected from Hematocrit (Hct), Hemoglobin (Hb), mean corpuscular volume (MCV), and mean corpuscular hemoglobin (MCH).

37. The method of claim 27, wherein the composition provides the subject with improved hematology parameters comprising a higher level of each of a plurality of said parameters selected from Hematocrit (Hct), Hemoglobin (Hb), mean corpuscular volume (MCV), and mean corpuscular hemoglobin (MCH).

38. The method of claim 36, wherein the composition provides a higher level of all of said hematology parameters.

39. The method of claim 37, wherein the composition provides a higher level of all of said hematology parameters.

40. The method of claim 28, wherein said markers indicate an improvement associated with one or both of the lungs and kidneys of the SCD subject.

41. The method of claim 29, wherein said markers indicate an improvement associated with one or both of the lungs and kidneys of the SCD subject.

42. The method of claim 32, wherein said markers indicate an improvement associated with one or both of the lungs and kidneys of the SCD subject.

43. The method of claim 33, wherein said markers indicate an improvement associated with one or both of the lungs and kidneys of the SCD subject.

44. The method of claim 35, wherein said markers indicate an improvement associated with one or both of the lungs and kidneys of the SCD subject.

45. The method of claim 36, wherein said markers indicate an improvement associated with one or both of the lungs and kidneys of the SCD subject.

* * * * *